(12) United States Patent
He et al.

(10) Patent No.: US 11,241,436 B2
(45) Date of Patent: Feb. 8, 2022

(54) AUTOPHAGY INDUCERS FOR TREATMENT OF CNS CONDITIONS

(71) Applicants: Northwestern University, Evanston, IL (US); The United States of America, as represented by the Secretary, Department of Health and Human Services, Bethesda, MD (US); University of Kansas, Lawrence, KS (US)

(72) Inventors: Congcong He, Chicago, IL (US); Sui Huang, Chicago, IL (US); Chen Wang, Chicago, IL (US); Altea Rocchi, Evanston, IL (US); Juan Jose Marugan, Gaithersburg, MD (US); Marc Ferrer, Potomac, MD (US); Samarjit Patnaik, Gaithersburg, MD (US); Yuchi Chen, Rockville, MD (US); Kevin Frankowski, Pittsboro, NC (US); Frank J. Schoenen, Lawrence, KS (US)

(73) Assignees: Northwestern University, Evanston, IL (US); The United States of Americans represented by the Secretary, Department of Health and Human Services, Bethesda, MD (US); University of Kansas, Lawrence, KS (US)

( * ) Notice: Subject to any disclaimer, the term of this patent is extended or adjusted under 35 U.S.C. 154(b) by 102 days.

(21) Appl. No.: 16/480,885

(22) PCT Filed: Jan. 25, 2018

(86) PCT No.: PCT/US2018/015293
§ 371 (c)(1),
(2) Date: Jul. 25, 2019

(87) PCT Pub. No.: WO2018/140630
PCT Pub. Date: Aug. 2, 2018

(65) Prior Publication Data
US 2020/0009146 A1 Jan. 9, 2020

Related U.S. Application Data

(60) Provisional application No. 62/450,336, filed on Jan. 25, 2017, provisional application No. 62/537,260, filed on Jul. 26, 2017.

(51) Int. Cl.
*A61K 31/519* (2006.01)
*A61P 25/30* (2006.01)
*A61K 31/704* (2006.01)

(52) U.S. Cl.
CPC .......... *A61K 31/519* (2013.01); *A61K 31/704* (2013.01); *A61P 25/30* (2018.01)

(58) Field of Classification Search
CPC ...... A61K 31/519; A61K 31/704; A61P 25/30
See application file for complete search history.

(56) References Cited

U.S. PATENT DOCUMENTS

| 4,235,871 A | 11/1980 | Papahadjopoulos et al. |
| 4,501,728 A | 2/1985 | Geho et al. |

(Continued)

FOREIGN PATENT DOCUMENTS

| WO | WO 97/30731 A2 | 8/1997 |
| WO | WO 99/02685 A1 | 1/1999 |

(Continued)

OTHER PUBLICATIONS

Kavirajan et al., Lancet Neurol 2007, 6, 782-92.*
Vattakatuchery et al., World Journal of Psychiatry; 2013, 3(3), 62-64.*
Adlard et al., "Voluntary Exercise Decreases Amyloid Load in a Transgenic Model of Alzheimer's Disease," *The Journal of Neuroscience*, 25(17):4217-4221 (2005).

(Continued)

*Primary Examiner* — Pancham Bakshi
(74) *Attorney, Agent, or Firm* — Leydig, Voit & Mayer, Ltd.

(57) ABSTRACT

The invention provides a compound of formula (I): wherein $R^1$, $R^2$, $R^3$, and $R^4$ are as defined herein, ginsenoside Rg2 of structure (II): or a combination thereof, for use in treating or preventing a condition responsive to the induction of autophagy in a brain of a mammal in need thereof.

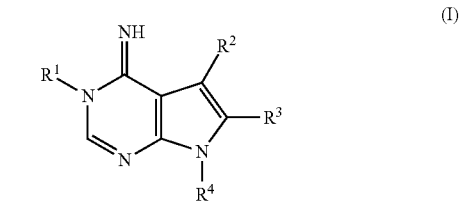

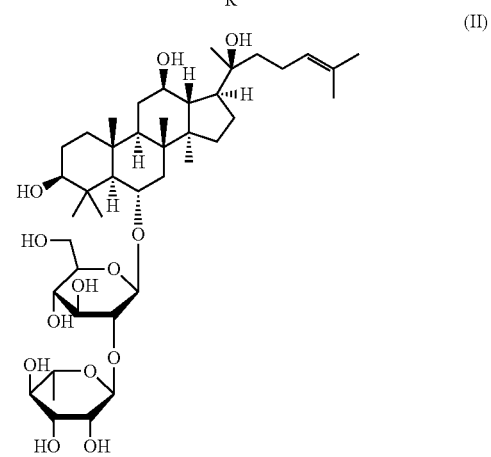

9 Claims, 29 Drawing Sheets

(56) References Cited

U.S. PATENT DOCUMENTS

| | | | |
|---|---|---|---|
| 4,837,028 A | 6/1989 | Allen | |
| 5,019,369 A | 5/1991 | Presant et al. | |
| 5,565,332 A | 10/1996 | Hoogenboom et al. | |
| 5,585,089 A | 12/1996 | Queen et al. | |
| 5,705,188 A | 1/1998 | Junichi et al. | |
| 5,824,544 A | 10/1998 | Armentano et al. | |
| 5,830,730 A | 11/1998 | German et al. | |
| 5,872,154 A | 2/1999 | Wilson et al. | |
| 5,885,808 A | 3/1999 | Spooner et al. | |
| 5,981,225 A | 11/1999 | Kochanek et al. | |
| 5,994,106 A | 11/1999 | Kovesdi et al. | |
| 5,994,128 A | 11/1999 | Fallaux et al. | |
| 5,994,132 A | 11/1999 | Chamberlain et al. | |
| 6,001,557 A | 12/1999 | Wilson et al. | |
| 6,019,978 A | 2/2000 | Ertl et al. | |
| 6,033,908 A | 3/2000 | Bout et al. | |
| 6,054,297 A | 4/2000 | Carter et al. | |
| 6,180,370 B1 | 1/2001 | Queen et al. | |
| 8,084,599 B2 | 12/2011 | Rossi et al. | |
| 2014/0323438 A1* | 10/2014 | Frankowski | C07F 7/1804 514/63 |

FOREIGN PATENT DOCUMENTS

| | | |
|---|---|---|
| WO | WO 00/09675 A1 | 2/2000 |
| WO | WO 00/12738 A1 | 3/2000 |
| WO | WO 2013/090912 A1 | 6/2013 |

OTHER PUBLICATIONS

Alirezaei et al., "Short-term fasting induces profound neuronal autophagy," *Autophagy*, 6(6):702-710 (2010).

Bartlett et al., "Dopamine responsiveness is regulated by targeted sorting of D2 receptors," *PNAS*, 102(32):11521-11526 (2005).

Berge et al., "Pharmaceutical Salts," *Journal of Pharmaceutical Sciences*, 66(1):1-19 (1977).

Boland et al., "Macroautophagy Is Not Directly Involved in the Metabolism of Amyloid Precursor Protein," *The Journal of Biological Chemistry*, 285(48):37415-37426 (2010).

Boyce-Rustay et al., "Animal Models of Acute and Chronic Inflammatory and Nociceptive Pain," *Methods in Molecular Biology*, 617:41-55 (2010).

Caccamo et al., "Molecular Interplay between Mammalian Target of Rapamycin (mTOR), Amyloid-β, and Tau: Effects on Cognitive Impairments," *The Journal of Biological Chemistry*, 285(17):13107-13120 (2010).

Cai et al., "BACE1 is the major β-secretase for generation of Aβ peptides by neurons," *Nature Neuroscience*, 4(3):233-234 (2001).

Chen et al., "Fasting activates macroautophagy in neurons of Alzheimer's disease mouse model but is insufficient to degrade amyloid-beta," *Scientific Reports*, 5:12115 (2015).

Cho et al., "SUMO1 promotes Aβ production via the modulation of autophagy," *Autophagy*, 11(1):100-112 (2015).

De Duve et al., "Functions of Lysosomes," *Annu. Rev. Physiol.*, 28:435-492 (1966).

England et al., "Cannabinoids in experimental stroke: a systematic review and meta-analysis," *Journal of Cerebral Blood Flow & Metabolism*, 35:348-358 (2015).

Erickson et al., "Exercise training increases size of hippocampus and improves memory," *PNAS*, 108(7):3017-3022 (2011).

European Patent Office, International Search Report in International Patent Application No. PCT/US2018/015293, dated Jun. 6, 2018.

European Patent Office, Written Opinion in International Patent Application No. PCT/US2018/015293, dated Jun. 6, 2018.

Finn et al., "Endocytosis of the Mu Opiod Receptor Reduces Tolerance and a Cellular Hallmark of Opiate Withdrawal," *Neuron*, 32:829-839 (2001).

Flores-Otero et al., "Ligand-specific endocytic dwell times control functional selectivity of the cannabinoid receptor 1," *Nature Communications*, 5:4589 (2014).

Frake et al., "Autophagy and neurodegeneration," *The Journal of Clinical Investigation*, 125(1):65-74 (2015).

Frankowski et al., "Discovery and Development of Small Molecules That Reduce PNC Prevalanence," *Probe Reports from the NIH Molecular Libraries Program*; Bethesda (MD): National Center for Biotechnology Information (US) (2010).

Fratta et al., "Molecular mechanisms of cannabinoid addiction," *Current Opinion in Neurobiology*, 23:487-492 (2013).

Furuya et al., "The Evolutionarily Conserved Domain of Beclin 1 is Required for Vps34 Binding, Autophagy and Tumor Suppressor Function," *Autophagy*, 1(1):46-52 (2005).

Games et al., "Alzheimer-type neuropathology in transgenic mice overexpressing V717F β-amyloid precursor protein," *Nature*, 373:523-527 (1995).

Gao et al., "Biochemical Isolation and Characterization of the Tubulovesicular LC3-postiive Autophagosomal Compartment," *The Journal of Biological Chemistry*, 285(2):1371-1383 (2010).

García-Mesa et al., "Physical Exercise Protects Against Alzheimer's Disease in 3xTg-AD Mice," *Journal of Alzheimer's Disease*, 24:421-454 (2011).

Gerich et al., "Medical Marijuana for Digestive Disorders: High Time to Prescribe?" *The American Journal for Gastroenterology*, 110:208-214 (2015).

Goedert et al., "A Century of Alzheimer's Disease," *Science*, 314:777-781 (2006).

Grumati et al., "Physical exercise stimulates autophagy in normal skeletal muscles but is detrimental for collagen VI-deficient muscles," *Autophagy*, 7(12):1415-1423 (2011).

Gui et al., "Simultaneous enantiomer determination of 20 (R)- and 20 (S)-ginsenoside-$Rg_2$ in rat plasma after intravenous administration using HPLC method," *Journal of Chromatography B*, 850:1-6 (2007).

Haass et al., "Trafficking and Proteolytic Processing of APP," *Cold Spring Harb. Perspect. Med.*, 2:a006270 (2012).

Hall et al., "Adverse health effects of non-medical cannabis use," *Lancet*, 374:1383-1391 (2009).

Hanyaloglu et al., "Regulation of GPCRs by Endocytic Membrane Trafficking and Its Potential Implications," *Annu. Rev. Pharmacol. Toxicol.*, 48:537-568 (2008).

Hara et al., "Suppression of basal autography in neural cells causes neurodegenerative disease in mice," *Nature*, 441:885-889 (2006).

He et al., "Regulation Mechanisms and Signaling Pathways of Autophagy," *Annu. Rev. Genet.*, 43:67-93 (2009).

He et al., "Exercise induces autophagy in peripheral tissues and in the brain," *Autophagy*, 8(10):1548-1551 (2012).

He et al., "Beclin 2 Functions in Autophagy, Degradation of G Protein-Coupled Receptors, and Metabolism," *Cell*, 154(5):1085-1099 (2013).

He et al. "The Beclin 1 interactome," *Curr. Opin. Cell Biol.*, 22(2):140-149 (2010).

He et al., "Exercise-induced BCL2-regulated autophagy is required for muscle glucose homeostasis," *Nature*, 481(7382):511-515 (2012).

Hill et al., "Medical Marijuana for Treatment of Chronic Pain and Other Medical and Psychiatric Problems: A Clinical Review," *JAMA*, 313(24):2474-2483 (2015).

Holtzman et al., "Alzheimer's Disease: The Challenge of the Second Century," *Sci. Transl. Med.*, 3(77):77sr1 (2011).

Howlett et al., "$CB_1$ Cannabinoid Receptors and their Associated Proteins," *Curr. Med. Chem.*, 17(14):1382-1393 (2010).

Huang et al., "Alzheimer Mechanisms and Therapeutic Strategies," *Cell*, 148(6):1204-1222 (2012).

Hurtado et al., "Aβ Accelerates the Spatiotemporal Progression of Tau Pathology and Augments Tau Amyloidosis in an Alzheimer Mouse Model," *The American Journal of Pathology*, 177(4):1977-1988 (2010).

Hurtado et al., "Selectively Silencing GSK-3 Isoforms Reduces Plaques and Tangles in Mouse Models of Alzheimer's Disease," *The Journal of Neuroscience*, 32(21):7392-7402 (2012).

Jaeger et al., "Regulation of Amyloid Precursor Protein Processing by the Beclin 1 Complex," *PLoS One*, 5(6):e11102 (2010).

Kim et al., "Synthetic dsRNA Dicer substrates enhance RNAi potency and efficacy," *Nature Biotechnology*, 23(2):222-226 (2005).

(56) References Cited

OTHER PUBLICATIONS

Komatsu et al., "Loss of autophagy in the central nervous system causes neurodegeneration in mice," *Nature*, 441:880-884 (2006).
Kuma et al., "Physiological role of autophagy as an intracellular recycling system: With an emphasis on nutrient metabolism," *Seminars in Cell & Developmental Biology*, 21:683-690 (2010).
Kuramoto et al., "Autophagy activation by novel inducers prevents BECN2-mediated drug tolerance to cannabinoids," *Autophagy*, 12(9):1460-1471 (2016).
LaFerla et al., "Intracellular amyloid-β in Alzheimer's disease," *Nature Reviews: Neuroscience*, 8:499-509 (2007).
Larson et al., "Exercise Is Associated with Reduced Risk for Incident Dementia among Persons 65 Years of Age and Older," *Annals of Internatl Medicine*, 144:73-81 (2006).
Le Bars et al., "Animal Models of Nociception," *Pharmacological Reviews*, 53(4):597-652 (2001).
Levine et al., "Development by Self-Digestion: Molecular Mechanisms and Biological Functions of Autophagy," *Development Cell*, 6:463-477 (2004).
Lucin et al., "Microglial beclin 1 regulates retromer trafficking and phagocytosis and is impaired in Alzheimer's disease," *Neuron*, 79(5):873-886 (2013).
Majumder et al., "Inducing Autophagy by Rapamycin Before, but Not After, the Formation of Plaques and Tangles Ameliorates Cognitive Deficits," *PLoS One*, 6(9):e25416 (2011).
Marchese et al., "G Protein-Coupled Receptor Sorting to Endosomes and Lysosomes," *Annu. Rev. Pharmacol. Toxicol.*, 48:601-629 (2008).
Martini et al., "Ligand-induced down-regulation of the cannabinoid 1 receptor is mediated by the G-protein-coupled receptor-associated sorting protein GASP1," *The FASEB Journal*, 21:802-811 (2007).
Mizushima et al., "Autophagy: Renovation of Cells and Tissues," *Cell*, 147:728-741 (2011).
Mizushima et al., "In Vivo Analysis of Autophagy in Response to Nutrient Starvation Using Transgenic Mice Expressing a Fluorescent Autoophagosome Marker," *Molecular Biology of the Cell*, 15:1101-1111 (2004).
Mizushima et al., "Autophagy in mammalian development and differentiation," *Nat. Cell. Biol.*, 12(9):823-830 (2010).
Moon et al., "Autophagy flux induced by ginsenoside-Rg3 attenuates human prion protein-mediated neurotoxicity and mitochondrial dysfunction," *Oncotarget*, 7(52):85697-85708 (2016).
Nilsson et al., "Aβ Secretion and Plaque Formation Depend on Autophagy," *Cell Reports*, 5:61-69 (2013).
Nixon et al., "The role of autophagy in neurodegenerative disease," *Nature Medicine*, 19(8):983-997 (2013).
Oakley et al., "Intraneuronal β-Amyloid Aggregates, Neurodegeneration, and Neuron Loss in Transgenic Mice with Five Familial Alzheimer's Disease Mutations: Potential Factors in Amyloid Plaque Formation," *The Journal of Neuroscience*, 26(40):10129-10140 (2006).
Panlilio et al., "Cannabinoid abuse and addiction: Clinical and preclinical findings," *Clin. Pharmacol. Ther.*, 97(6):616-627 (2015).
Pattingre et al., "Bcl-12 Antiapoptic Proteins Inhibit Beclin 1-Dependent Autophagy," *Cell*, 122:927-939 (2005).
Rocchi et al., "A *Becn1* mutation mediates hyperactive autophagic sequestration of amyloid oligomers and improved cognition in Alzheimer's disease," *PLOS Genetics*, 13(8):e1006962 (2017).
Rocchi et al., "Activating Autophagy by Aerobic Exercise in Mice," *Journal of Visualized Experiments*, 120:e55099 (2017).
Qu et al., "Promotion of tumorigenesis by heterozygous disruption of the *beclin 1* autophagy gene," *The Journal of Clinical Investigation*, 112(12):1809-1820 (2003).
Pickford et al., "The autophagy-related protein beclin 1 shows reduced expression in early Alzheimer disease and regulates amyloid β accumulation in mice," *The Journal of Clinical Investigation*, 118(6):2190-2199 (2008).
Rose et al., "Functional polarity is introduced by Dicer processing of short substrate RNAs," *Nucleic Acids Research*, 33(13):4140-4156 (2005).

Rusheweyh et al., "Physical activity and memory functions: An interventional study," *Neurobiology of Aging*, 32:1304-1319 (2011).
Sadleir et al., "Aβ reduction in BACE1 heterozygous null 5XFAD mice is associated with transgenic APP level," *Molecular Neurodegeneration*, 10:1 (2015).
Scarmeas et al., "Physical Activity, Diet, and Risk of Alzheimer Disease," *JAMA*, 302(6):627-637 (2009).
Shibuya et al., "Inhibiting ACAT1/SOAT1 in Microglia Stimulates Autophagy-Mediated Lysosomal Proteolysis and Increases Aβ1-42 Clearance," *The Journal of Neuroscience*, 34(43):14484-14501 (2014).
Sperling et al., "Toward defining the preclinical stages of Alzheimer's disease: Recommendations from the National Institute on Aging-Alzheimer's Association workgroups on diagnostic guidelines for Alzheimer's disease," *Alzheimers Dement.*, 7(3):280-292 (2011).
Sperling et al., "Preclinical Alzheimer disease—the challenges ahead," *Nat. Rev. Neurol.*, 9(1):54-58 (2013).
Spilman et al., "Inhibition of mTOR by Rapamycin Abolishes Cognitive Deficits and Reduces Amyloid-β Levels in a Mouse Model of Alzheimer's Disease," *PLoS One*, 5(4):e9979 (2010).
Swaminathan et al., "BECN1/Beclin 1 sorts cell-surface APP/amyloid β precursor protein for lysosomal degradation," *Autophagy*, 12(12):2404-2419 (2016).
Szoka et al., "Comparative Properties and Methods of Preparation of Lipid Vesicles (Liposomes)," *Ann. Rev. Biophys. Bioeng.*, 9:467-508 (1980).
Takahashi et al., "Intraneuronal Alzheimer Aβ42 Accumulates in Multivesicular Bodies and Is Associated with Synaptic Pathology," *American Journal of Pathology*, 161(5):1869-1879 (2002).
Tapia-Rojas et al., "Voluntary Running Attenuates Memory Loss, Decreases Neuropathological Changes and Induces Neurogenesis in a Mouse Model of Alzheimer's Disease," *Brain Pathology*, 26:62-74 (2016).
Tappe-Theodor et al., "A Molecular Basis of Analgesic Tolerance to Cannabinoids," *The Journal of Neuroscience*, 27(15):4165-4177 (2007).
Tian et al., "Adaptor complex AP2/PICALM, through interaction with LC3, targets Alzheimer's APP-CTF for terminal degradation via autophagy," *PNAS*, 110(42):17071-17076 (2013).
Tracy et al., "*BNIP2* Is an RB/E2F Target Gene Required for Hypoxia-Induced Autophagy," *Molecular and Cellular Biology*, 27(17):6229-6242 (2007).
Tsukada et al., "Isolation and characterization of autophagy-defective mutants of *Saccharomyces cerevisiae*," *FEBS Letters*, 333(1,2):169-174 (1993).
Wang et al., "Animal and cellular models of chronic pain," *Advanced Drug Delivery Reviews*, 55:949-965 (2003).
Wei et al., "JNK1-Mediated Phosphorylation of Bcl-2 Regulates Starvation-Induced Autophagy," *Mol. Cell.*, 30(6):678-688 (2008).
Whistler et al., "Modulation of Postendocytic Sorting of G Protein-Coupled Receptors," *Science*, 297(5581):615-620 (2002).
Whiting et al., "Cannabinoids for Medical Use: A Systematic Review and Meta-analysis," *JAMA*, 313(24):2456-2473 (2015).
Winblad et al., "Defeating Alzheimer's disease and other dementias: a priority for European science and society," *Lancet Neurol.*, 15:455-532 (2016).
Xie et al., "Autophagosome formation: core machinery and adaptations," *Nature Cell Biology*, 9(10):1102-1109 (2007).
Yamamato et al., "Autophagy-mediated clearance of huntingtin aggregates triggered by the insulin-signaling pathway," *The Journal of Cell Biology*, 172(5):719-731 (2006).
Yang et al., "Reversal of autophagy dysfunction in the TgCRND8 mouse model of Alzheimer's disease ameliorates amyloid pathologies and memory deficits," *Brain*, 134:258-277 (2011).
Yuede et al., "Effects of voluntary and forced exercise on plaque deposition, hippocampal vol. and behavior in the Tg2576 mouse model of Alzheimer's disease," *Neurobiol. Dis.*, 35(3):426-432 (2009).

\* cited by examiner

AUTOPHAGY INDUCERS FOR TREATMENT OF CNS CONDITIONS

CROSS-REFERENCE TO RELATED APPLICATIONS

This patent application is the U.S. national phase of International Patent Application No. PCT/US2018/015293, filed Jan. 25, 2018, which claims the benefit of U.S. Provisional Patent Applications No. 62/450,336, filed Jan. 25, 2017, and 62/537,260, filed Jul. 26, 2017, which are incorporated by reference in their entirety for all purposes.

STATEMENT REGARDING FEDERALLY SPONSORED RESEARCH AND DEVELOPMENT

This invention was made with Government support under Grant Number R00 DK094980 awarded by the National Institutes of Health and Grant Number R01 GM078555-05 awarded by the National Institute of General Medical Sciences. The Government has certain rights in this invention.

BACKGROUND OF THE INVENTION

Cannabinoids and related drugs, such as the marijuana-derived ingredients, generate profound behavioral effects (such as analgesic effects) that are therapeutic in many pathological conditions, including neurodegeneration, digestive disorders, spasticity, and chronic and cancer-related pain. However, long-term administration of cannabinoids for either medical or recreational purposes induces rapid development of tolerance (a demonstration of physical dependence), which is a limitation and concern of its medical use and may lead to addiction and withdrawal symptoms. Clinical data showed that 9% of adult cannabis users, and 17% of adolescent users, develop dependence and addiction after repeated dosage, which is not trivial given the widespread usage of illicit cannabinoids in many countries. Yet the pathogenic mechanisms of cannabinoid tolerance are not fully understood, and little is known about its prevention methods. Consequently, only a very small number of cannabinoid therapeutics have been approved and used clinically on market in limited regions; for example, the cannabis medication for spasticity, SATIVEX™, is prescribed as an oromucosal spray to ensure slow blood delivery and is carefully administered at low doses.

Neurodegenerative disorders such as Alzheimer's disease (AD) are characterized by protein aggregation and deposition, leading to progressive neuronal loss and cognitive decline among elderly populations. Amyloid plaques and neurofibrillary tangles are the two primary hallmarks of AD pathology, and aging is a major known risk factor of the disease. Amyloid plaques are formed by amyloid-β (Aβ) peptides, generated by sequential enzymatic cleavages of amyloid precursor protein (APP) at the plasma membrane. Besides the well-recognized extracellular deposition of Aβ, recent studies also revealed the accumulation of intracellular pools of Aβ in AD brain. Intracellular Aβ can be generated at the trans-Golgi network and endoplasmic reticulum as part of the secretory pathway, or be re-uptaken by neurons and glial cells from the secreted extracellular pools. Although many therapeutic efforts have been made to eliminate Aβ aggregation and deposition at either the synthesis or the degradation stage, no effective therapies are available so far to cure AD, and the mechanism driving the neurodegenerative progression remains unclear.

Thus, there remains an unmet need in the art for new therapies for treating neurodegenerative diseases and cannabinoid tolerance.

BRIEF SUMMARY OF THE INVENTION

The invention provides a compound of formula (I):

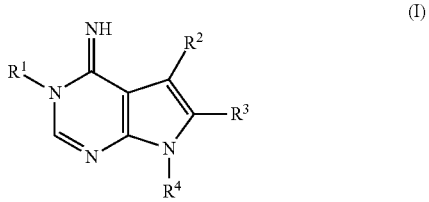

wherein $R^1$ is selected from the group consisting of alkyl, hydroxyalkyl, dialkoxyalkyl, trialkylsiloxyalkyl, thioalkyl, alkoxyalkyl, alkylthioalkyl, cycloalkyl, hydroxycycloalkyl, hydroxycycloalkylalkyl, thiocycloalkyl, alkoxycycloalkyl, alkylthiocycloalkyl, dialkylaminoalkyl, heterocyclyl, heterocyclylalkyl, heteroaryl, arylalkyl, arylalkylpiperidin-4-yl, arylpiperazinylalkyl, and heteroarylalkyl, $R^2$ is aryl or heteroaryl, $R^3$ is selected from the group consisting of H, alkyl, cycloalkyl, aryl, heteroaryl, arylalkyl, and heteroarylalkyl, $R^4$ is selected from the group consisting of alkyl, cycloalkyl, cycloalkylalkyl, aryl, heteroaryl, arylalkyl, and heteroarylalkyl, or a pharmaceutically acceptable salt thereof, wherein $R^1$, $R^2$, $R^3$, and $R^4$, other than H, are optionally substituted on the aryl and/or alkyl portion with one or more substituents selected from the group consisting of halo, alkyl, hydroxyalkyl, thioalkyl, alkoxy, alkylthioalkyl, alkoxycarbonyl, alkylthiocarbonyl, amino, alkylamino, dialkylamino, aminosulfonyl, hydroxyl, perfluoroalkoxy, alkylenedioxy, and alkylcarbonyl, ginsenoside Rg2 of structure (II):

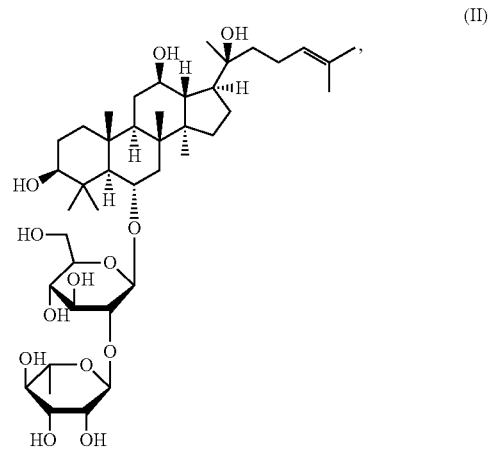

ginsenosides Re, Rf, or Rg1 of formula (III):

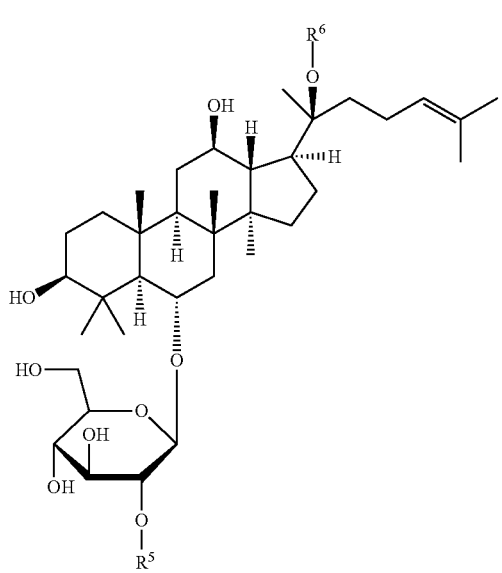

wherein $R^5$ is α-L-rhamnopyranosyl and $R^6$ is β-D-glucopyranosyl (ginsenoside Rc), $R^5$ is β-D-glucopyranosyl and $R^6$ is H (ginsenoside Rf), or $R^5$ is H and $R^6$ is β-D-glucopyranosyl (ginsenoside Rg1), ginsenosides Rb1, Rb2, or Rc of formula (IV):

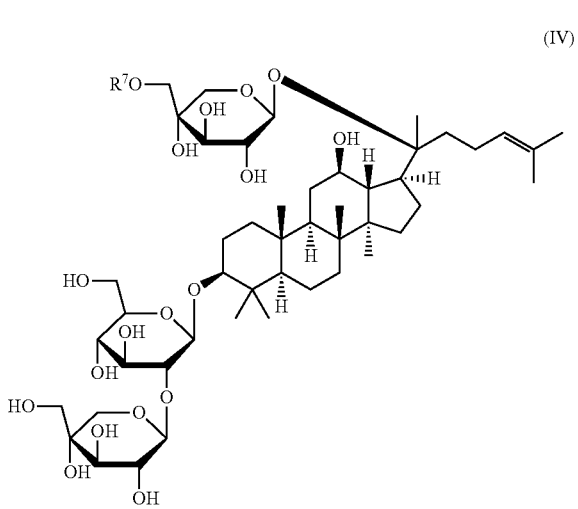

wherein $R^7$ is β-D-glucopyranosyl (ginsenoside Rb1), α-L-arabinopyranosyl (ginsenoside Rb2), or α-L-arabinofuranosyl (ginsenoside Rc), a compound of formula (V):

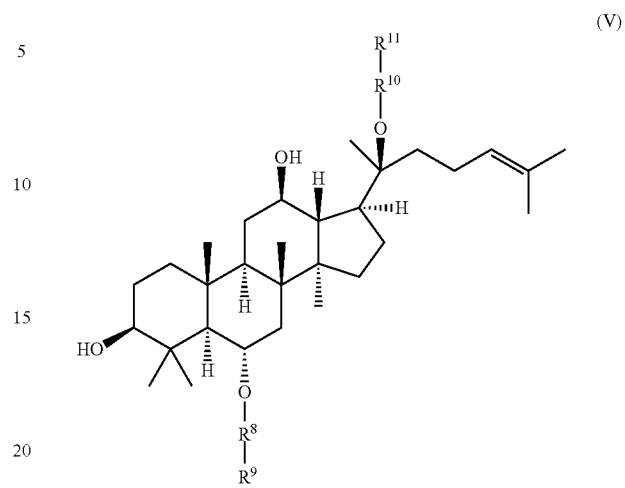

wherein $R^8$-$R^{11}$ are independently selected from the group consisting of β-D-glucopyranosyl, α-L-arabinopyranosyl, α-L-rhamnopyranosyl, and α-L-arabinofuranosyl, a compound of formula (VI):

(VI)

wherein $R^{12}$-$R^{15}$ are independently selected from the group consisting of β-D-glucopyranosyl, α-L-arabinopyranosyl, α-L-rhamnopyranosyl, and α-L-arabinofuranosyl, a compound of formula (VII):

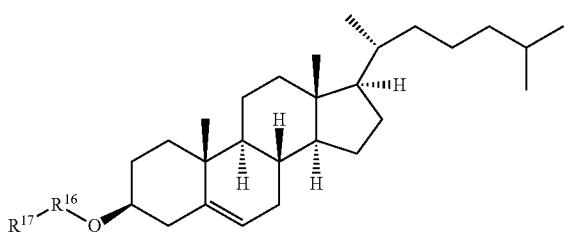

wherein $R^{16}$ and $R^{17}$ are independently selected from the group consisting of β-D-glucopyranosyl, α-L-arabinopyranosyl, α-L-rhamnopyranosyl, and α-L-arabinofuranosyl, a compound of formula (VIII):

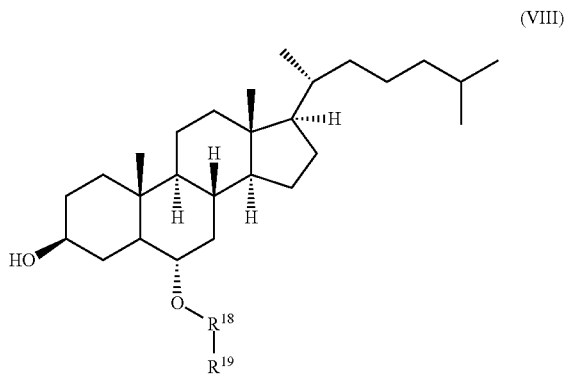

(VIII)

wherein $R^{18}$ and $R^{19}$ are independently selected from the group consisting of β-D-glucopyranosyl, α-L-arabinopyranosyl, α-L-rhamnopyranosyl, and α-L-arabinofuranosyl, a compound of formula (IX):

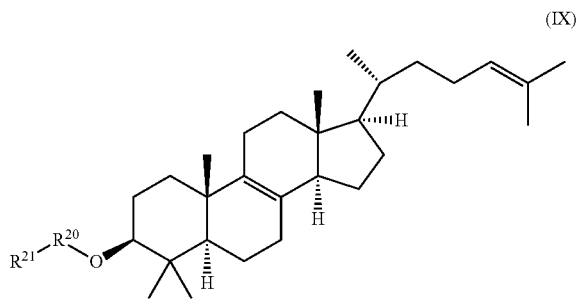

(IX)

wherein $R^{20}$ and $R^{21}$ are independently selected from the group consisting of β-D-glucopyranosyl, α-L-arabinopyranosyl, α-L-rhamnopyranosyl, and α-L-arabinofuranosyl, or a compound of formula (X):

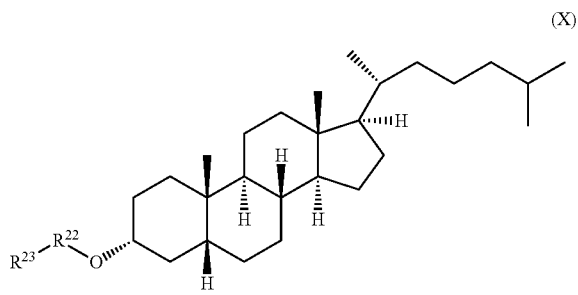

(X)

wherein $R^{22}$ and $R^{23}$ are independently selected from the group consisting of 3-D-glucopyranosyl, α-L-arabinopyranosyl, α-L-rhamnopyranosyl, and α-L-arabinofuranosyl, or any combination thereof, for use in of treating or preventing a condition responsive to the induction of autophagy in a brain of a mammal in need thereof.

The invention further provides a method of treating or preventing a condition responsive to the induction of autophagy in a brain of a mammal in need thereof comprising administering to the mammal a compound of the invention or pharmaceutically acceptable salt thereof as disclosed herein.

BRIEF DESCRIPTION OF THE SEVERAL VIEWS OF THE DRAWING(S)

Figure 2A:
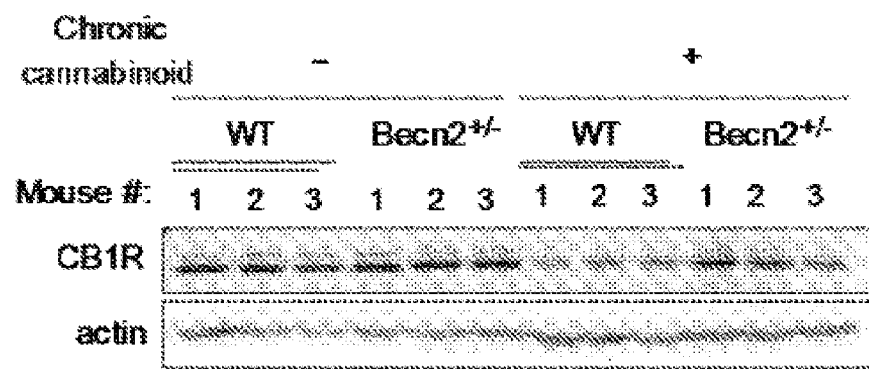
FIG. 2A shows Western blots for CB levels of brain lysates from Becn2+/− knockout (KO) and WT mice collected after 14 d of prolonged treatment of vehicle or the synthetic cannabinoid drug WIN55,212-2 (WIN). Representative images of 3 mice in each group are shown.
Figure 2B:
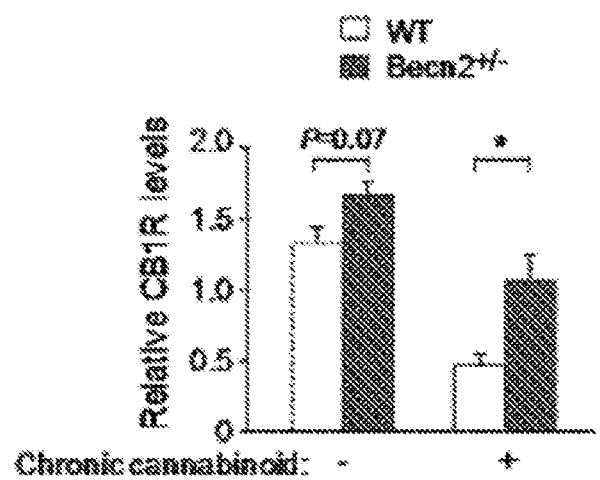
FIG. 2B shows the quantitation of relative CB1R levels depicted in FIG. 2A.
Figure 2C:
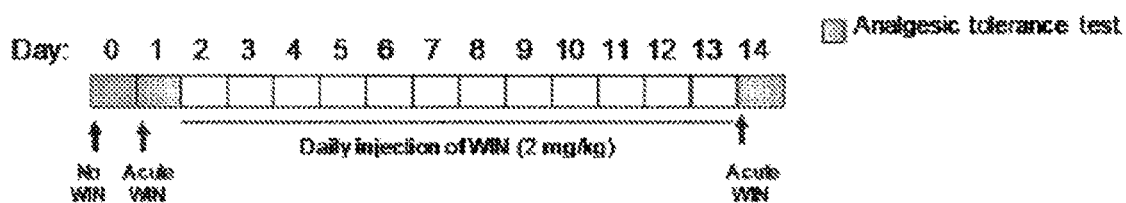

FIG. 2C shows the chronic cannabinoid treatment scheme, described in Methods. Briefly, mice were injected with WIN for 14 d, and analgesic tolerance was measured without WIN treatment on day 0, and after 1-h WIN treatment on day 1 and day 14.

Figure 2D:
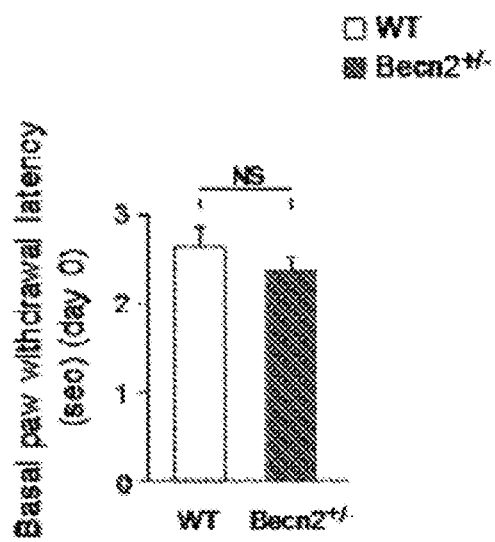

FIG. 2D shows baseline pain sensitivity of WT and Becn2+/− mice before chronic WIN treatment (day 0, agonist-free). N≥16 mice/group.

Figure 2E:
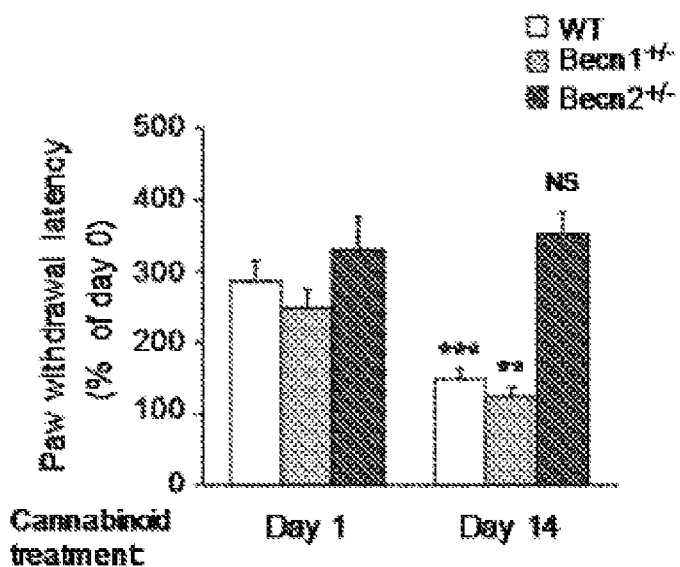

FIG. 2E shows that Becn2+/− mice show resistance to analgesic tolerance to chronic WIN treatment. Becn2+/−, Becn1+/− and WT mice were treated with daily WIN for 14 d, and the analgesic effect of WIN was analyzed as shown in FIG. 2B. Statistics are comparing the same genotype on day 1 and day 14. N=9-13 mice/group. Results represent mean±s.e.m. *P<0.05; P<0.01; *P<0.001; NS, not significant (t-test). The results show that loss of Beclin 2 confers resistance to analgesic tolerance induced by chronic usage of cannabinoid drugs.

Figure 3:
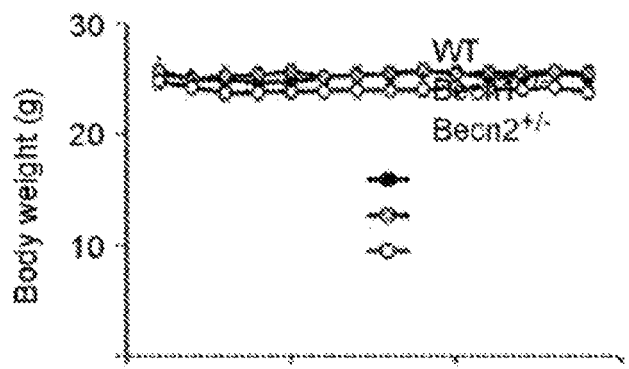

FIG. 3 shows the body weight of WT, Becn1+/− and Becn2+/− mice during chronic WIN treatment. N=9-13 mice/group. Results represent mean±s.e.m.

Figure 4A:
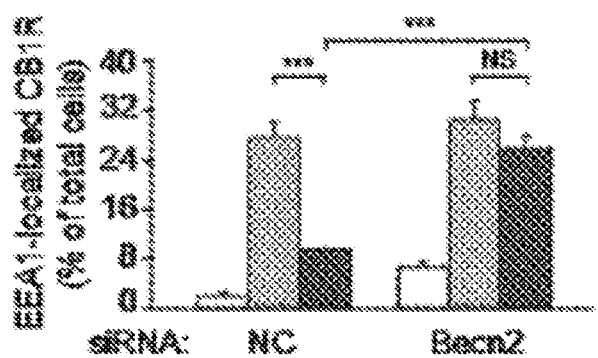
Figure 4B:
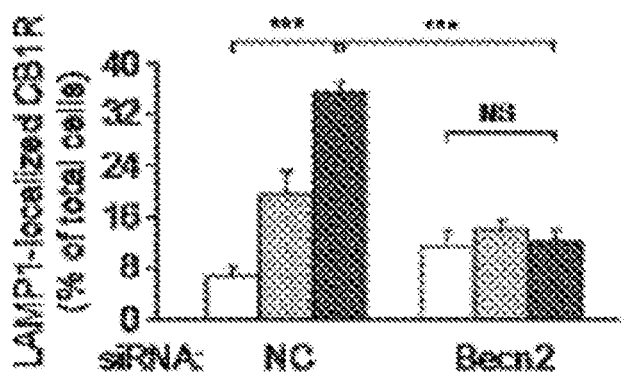

FIGS. 4A and 4B show quantification of immunofluorescence imaging of the effects of non-targeting control (NC) or Becn2 siRNA on the fate of endocytosed CB1R. HEK293 cells stably expressing Flag-CB 1R were fed with anti-Flag antibody, treated with the agonist WIN for 30 or 60 min and immunostained as described in Methods. Percentages of cells with CB1R-EEA1 (FIG. 4A) or CB1R-LAMP (FIG. 4B) colocalization in >200 cells per experiment were quantified from 4 independent experiments.

Figure 4C:
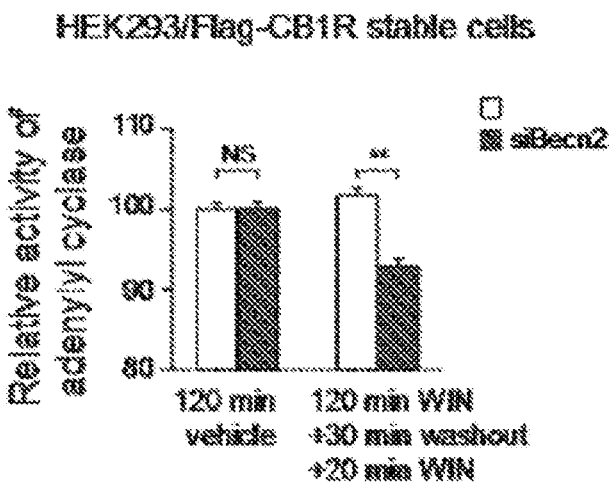

FIG. 4C shows that Becn2 knockdown suppresses the adenylyl cyclase activity downstream of CB1R after prolonged agonist exposure. HEK293/Flag-CB1 R cells transfected with indicated siRNAs were treated either with vehicle for 120 min, or with WIN for 120 min to induce CB1R internalization and degradation, followed by agonist washout and antagonist (rimonabant) treatment for 30 min to trigger CB recycling and another 20 min treatment of WIN to activate any CB1R at the cell surface. Results represent mean±s.e.m of 3 independent experiments.

Figure 4D:
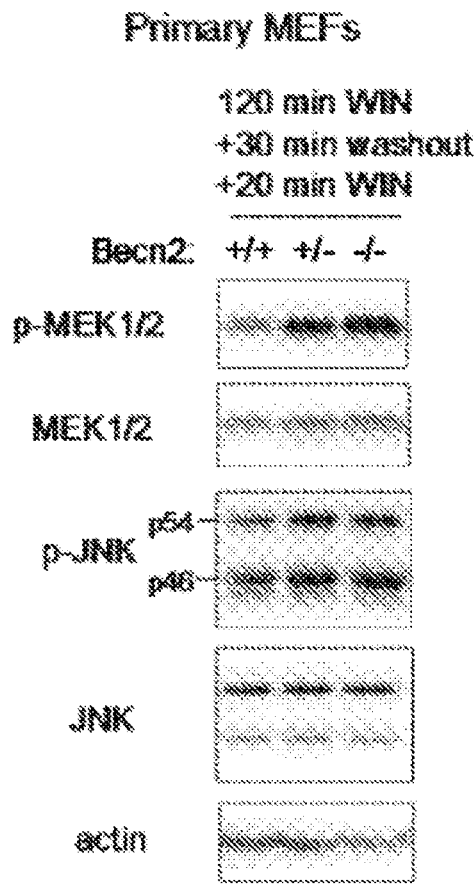
Figure 4E:
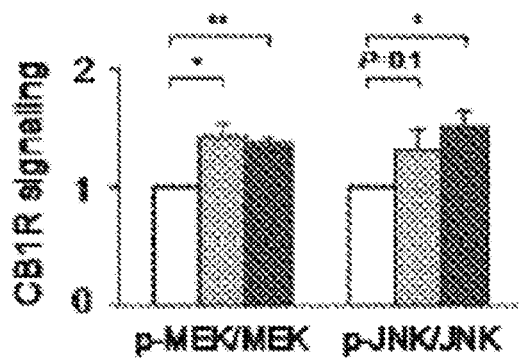

FIGS. 4D and 4E show that Beclin 2 depletion increases cannabinoid-induced CB1R signaling after prolonged exposure. Becn2+/+, Becn2+/− or Becn2−/− primary MEFs were treated as in described for FIG. 4B. Phosphorylation of MEK and JNK downstream of CB1R was analyzed by Western blot (FIG. 4D) and quantified from 3 independent experiments (FIG. 4E). Results represent mean±s.e.m. *P<0.05; P<0.01; *P<0.001; NS, not significant (t-test).

Figure 5:
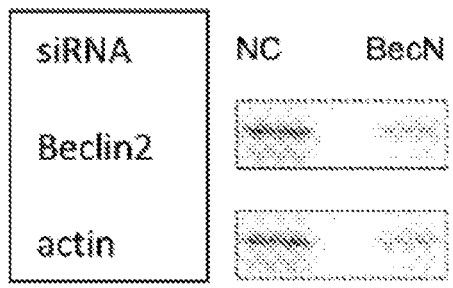

FIG. 5 shows Western blot detection of Beclin 2 in HEK293 cells transfected with non-targeting control (NC) or Becn2 siRNA.

Figure 6A:
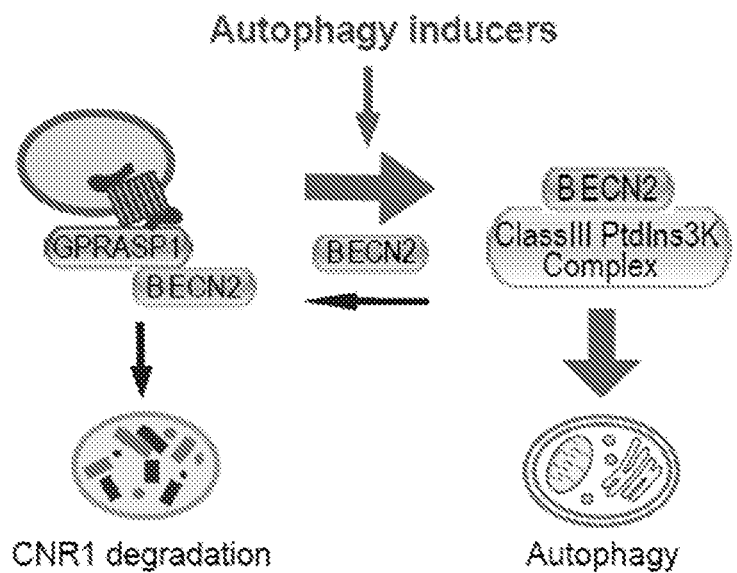

FIG. 6A shows a competitive recruiting model of Beclin 2 by the two lysosomal degradation pathways: autophagy induction promotes sequestering of Beclin 2 to the autophagy pathway from the Beclin 2-GASP1 complex, and thus attenuates lysosomal degradation of CB1R and maintains its responsiveness.

Figure 6B:
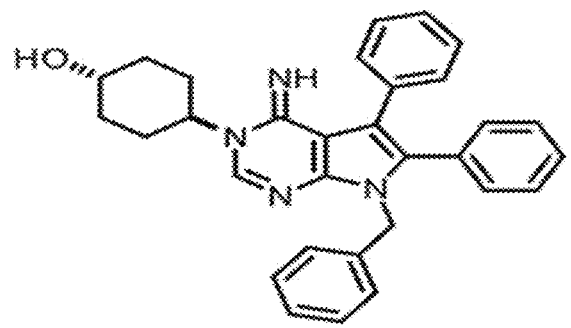

FIG. 6B shows the chemical structure of ML246.

Figure 6C:
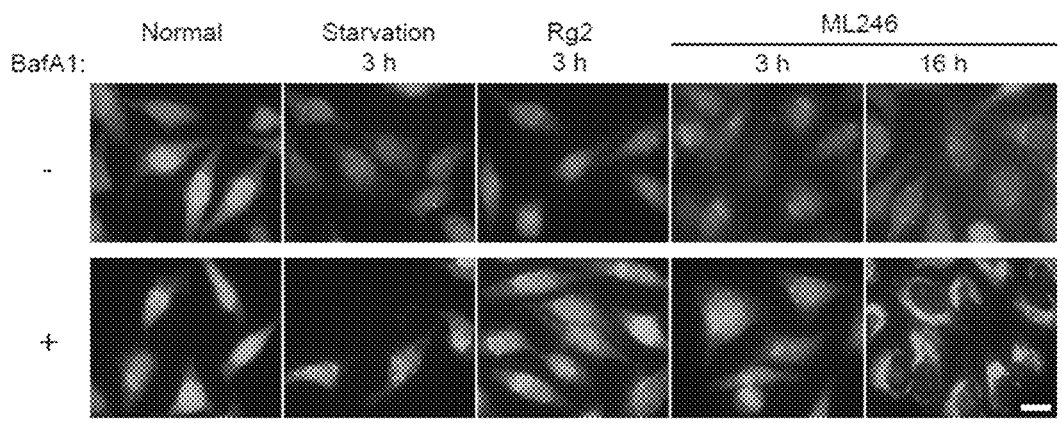
Figure 6D:
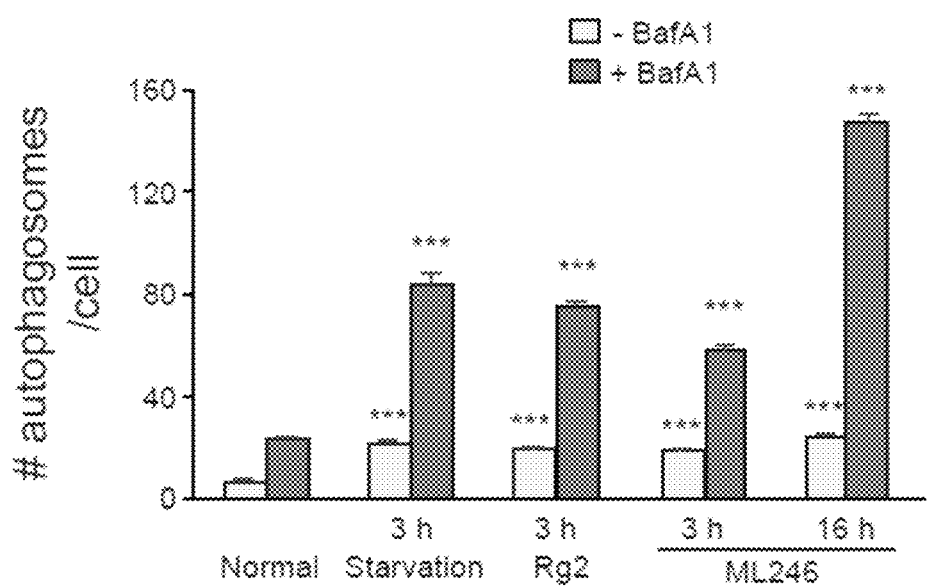

FIG. 6C shows representative images and FIG. 6D shows quantification of GFP-LC3 puncta in Hela cells stably expressing GFP-LC3 cultured for 3 h in normal or starvation medium, or treated with Rg2 or ML246 in normal medium for 3 h or 16 h, in the presence or absence of bafilomycin A1 (BafA1). Results represent mean±s.e.m. Statistics are comparing the indicated value with or without BafA 1 to the one under the normal condition.

Figure 6E:
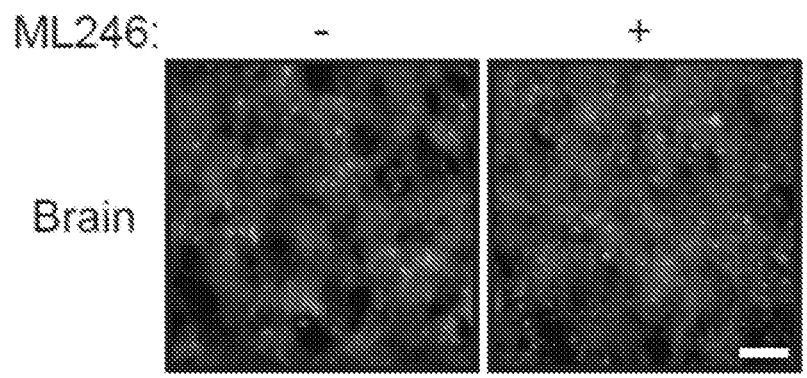

FIG. 6E shows representative images of GFP-LC3 puncta in brain of GFP-LC3 transgenic mice injected with vehicle or ML246. Results represent mean±s.d. Scale bar, 25 μm. N>100 cells or N2::4 mice.

Figure 6F:
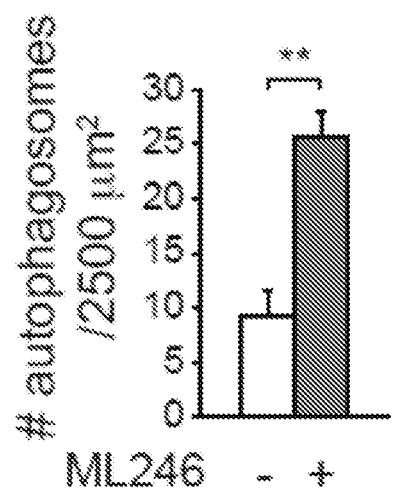

FIG. 6F shows quantification of GFP-LC3 puncta depicted in FIG. 6E.

Figure 7:
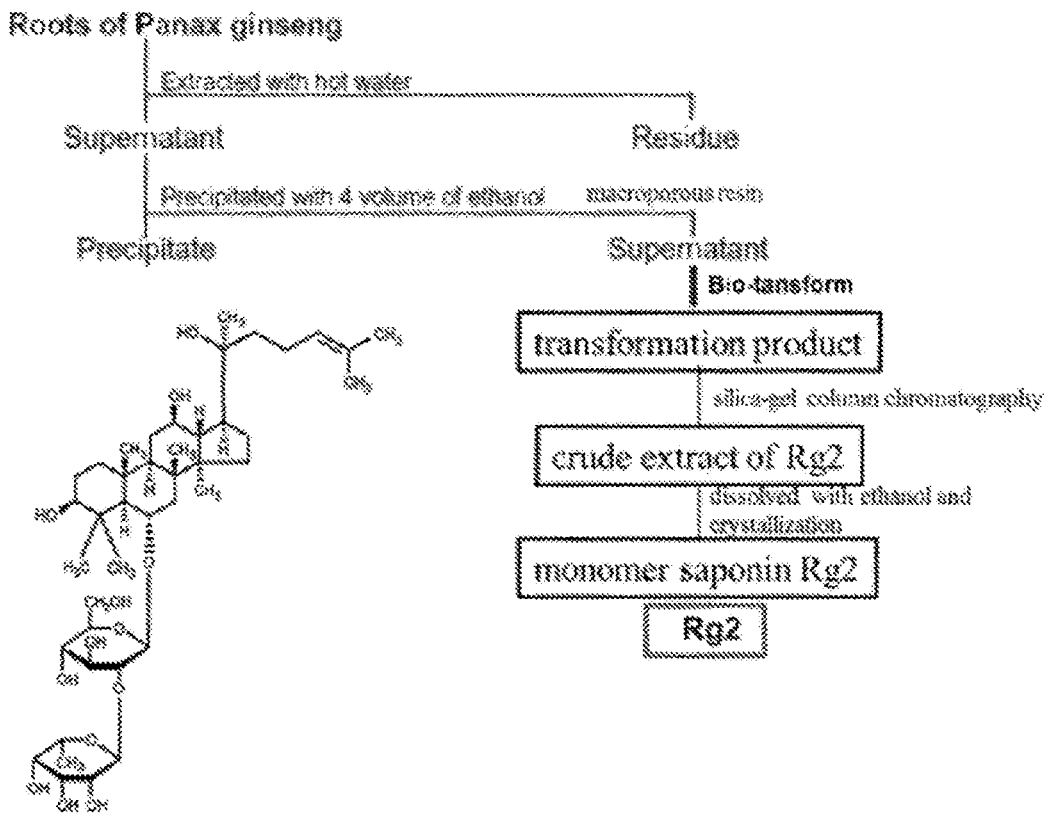

FIG. 7 shows the isolation scheme and chemical structure of Rg2.

Figure 8A:
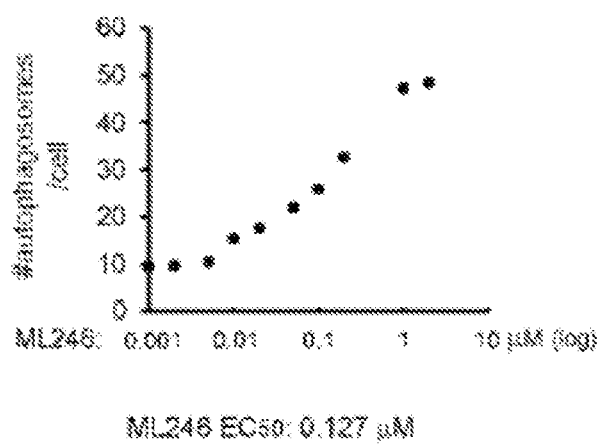

FIG. 8A shows EC50 of ML246 in autophagy induction. Quantification of GFP-LC3 puncta in GFP-LC3/Hela cells after 3-h treatment of ML246 at indicated concentrations.

Figure 8B:
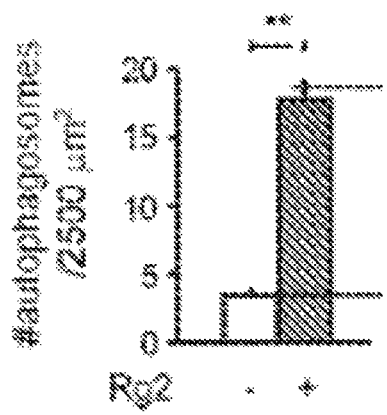

FIG. 8B shows quantification of GFP-LC3 puncta in brain sections of GFP-LC3 mice injected with vehicle or 20 mg/kg Rg2 once daily for 3 d. Scale bar, 20 μm. Results represent mean±s.d. N≥4 mice.

Figure 8C:
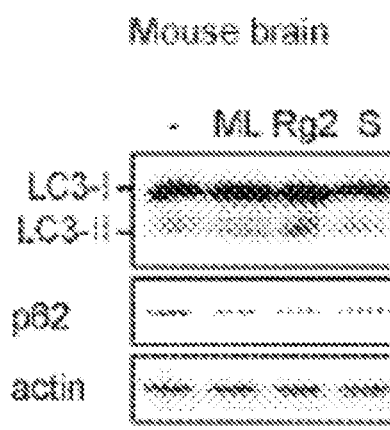

FIG. 8C shows the Western blot detection of LC3 and p62 in brain samples of mice injected with vehicle, ML246 or Rg2 once daily for 3 d, or starved for 48 h.

Figure 8D:
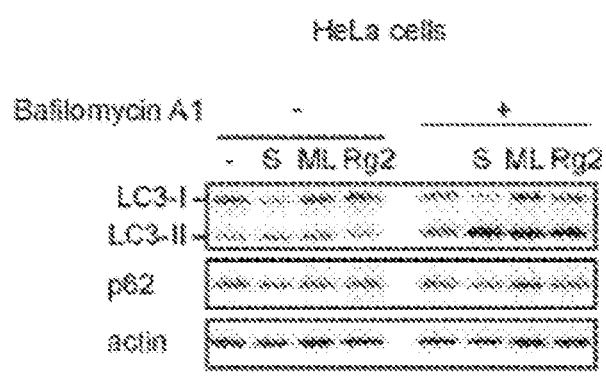

FIG. 8D shows the Western blot detection of LC3 and p62 in Hela cells cultured in normal or starvation medium, or in normal medium supplied with 0.5 μM ML246 or 100 μM Rg2 in the presence or absence of the lysosomal inhibitor bafilomycin A 1 for 3 h. S, starvation; ML=ML246.

Figure 9A:
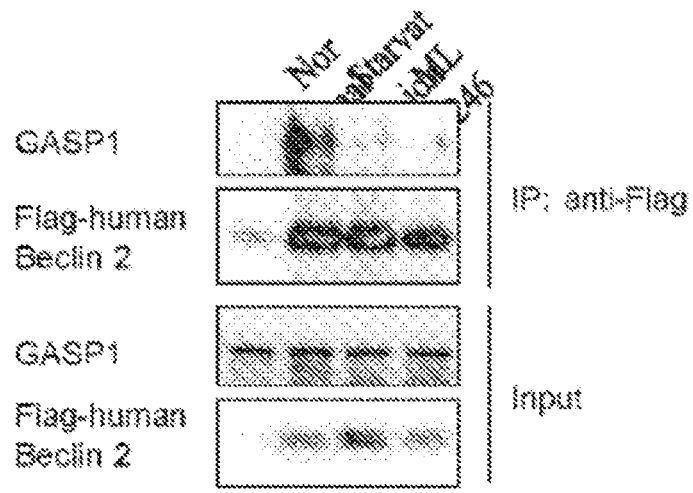

FIG. 9A shows coimmunoprecipitation of endogenous human GASP1 with Flag-human Beclin 2 in HEK293 cells treated with normal or starvation medium, or normal medium with ML246 for 3 h.

Figure 9B:
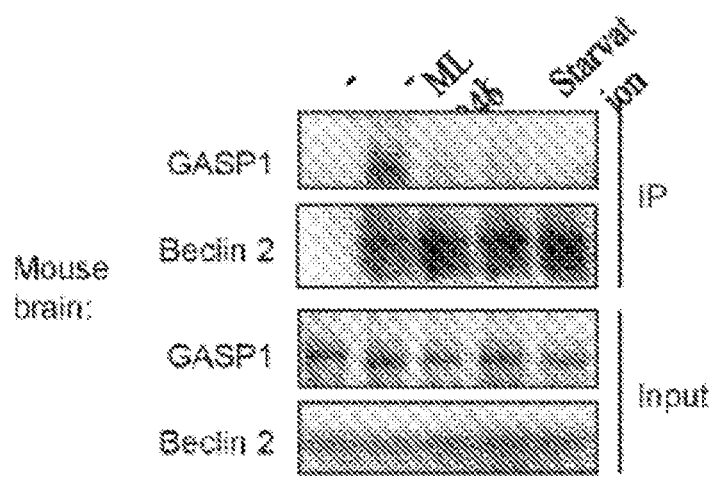

FIG. 9B shows coimmunoprecipitation of endogenous GASP1 with endogenous Beclin 2 using brain lysates from WT mice treated with vehicle, ML246 or Rg2, or with 48-h starvation. Lysates in each group were pooled from 3 mice.

Figure 10A:
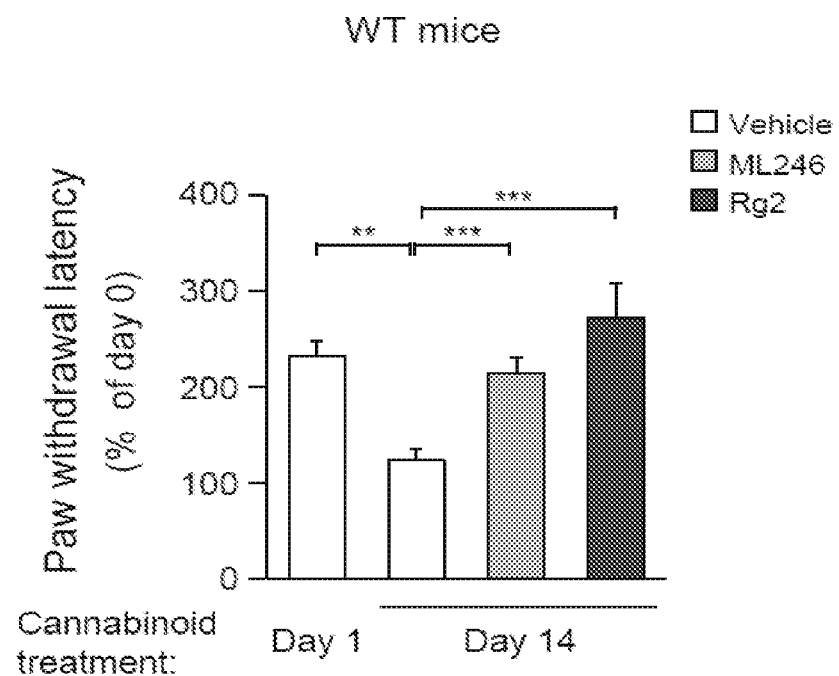

FIG. 10A shows analgesic tolerance of WT mice simultaneously treated with daily WIN and vehicle, ML246, or Rg2 for 14 d.

Figure 10B:
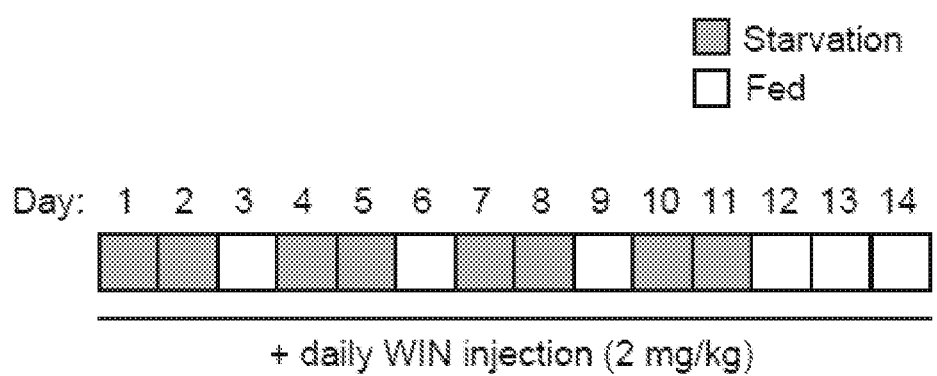

FIG. 10B shows a periodic fasting scheme. WT mice underwent 48 h-fast followed by 24 h-feeding cycles during chronic WIN treatment.

Figure 10C:
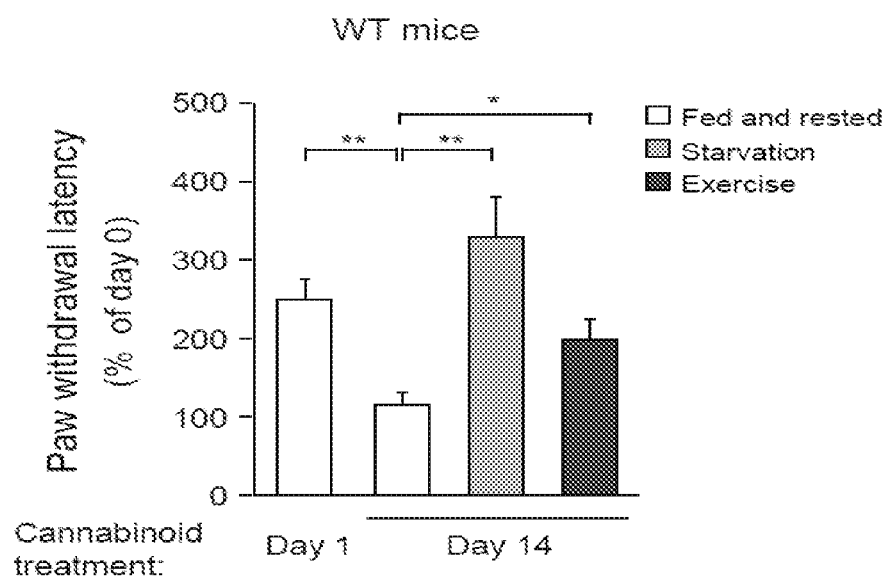

FIG. 10C shows analgesic tolerance of WT mice housed under normal conditions or subjected to either "2 days on-1 day off" periodic starvation or running-wheel exercise, with daily WIN treatment for 14 d. N=8-14 mice/group. Results represent mean±s.e.m.

Figure 11A:
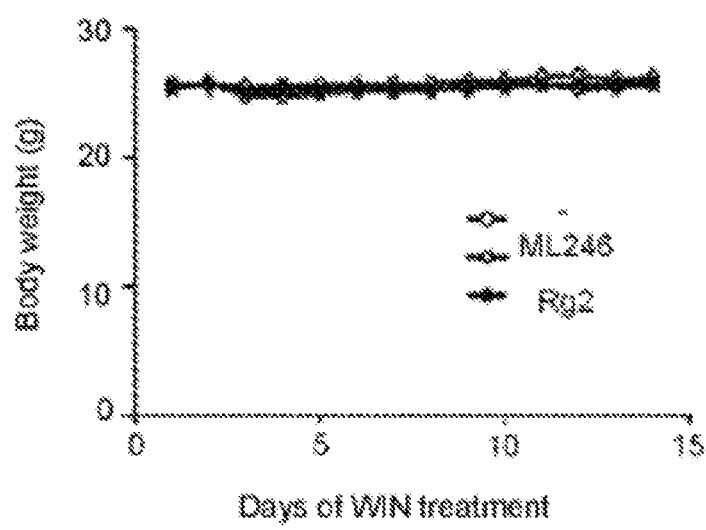

FIG. 11A shows body weight of WT mice injected with vehicle, 10 mg/kg ML246, or 20 mg/kg Rg2 during chronic WIN treatment.

Figure 11B:
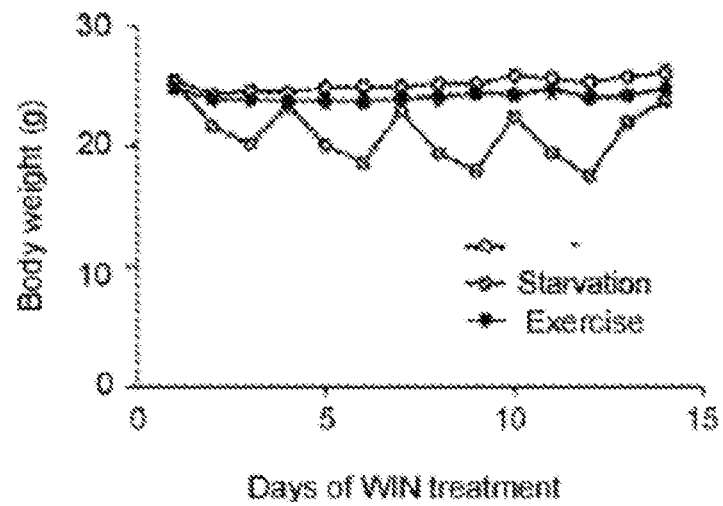

FIG. 11B shows body weight of WT mice housed under nail al fed-and-resting conditions, or subjected to intermittent starvation or voluntary wheel exercise during chronic WIN treatment. Results represent mean±s.e.m. N=8-14 mice/group.

Figures 12A, 12B:
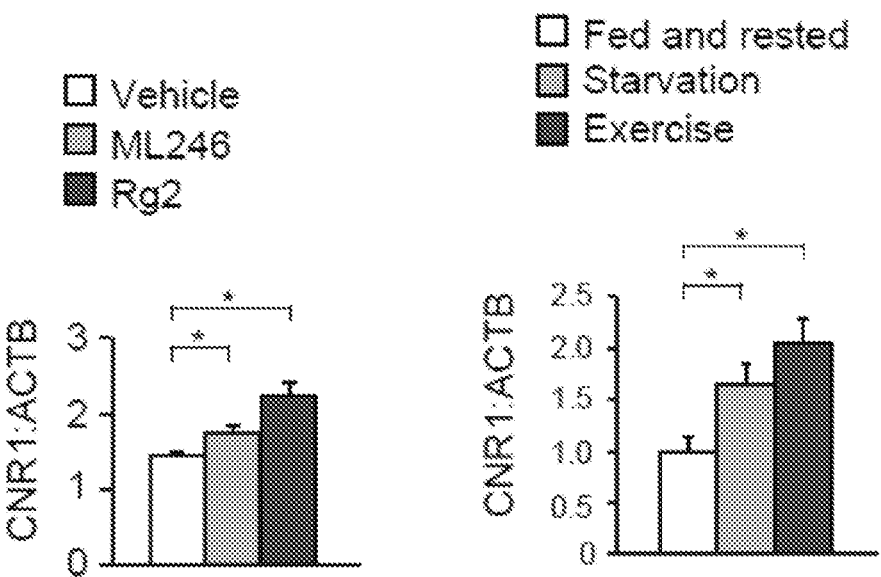

FIG. 12A shows brain CB1R levels of WT mice simultaneously treated with daily WIN and vehicle, ML246 or Rg2 for 14 d.

FIG. 12B shows brain CB1R levels of WT mice housed under normal conditions or subjected to either "2 days on-1 day off" periodic starvation or running-wheel exercise, with daily WIN treatment for 14 d. Western blot images (left) and quantification (right) of 3 mice in each group are shown.

Figure 12C:
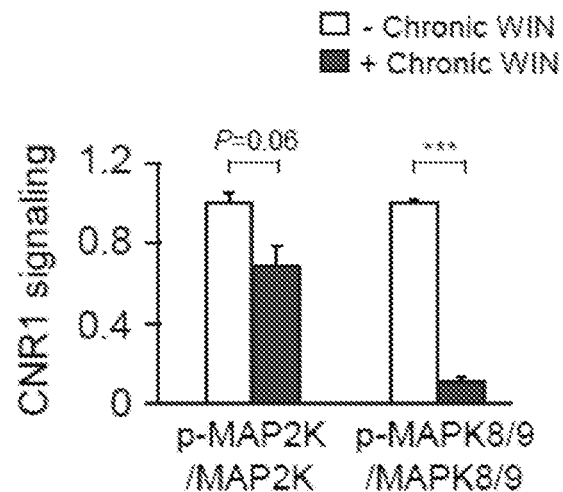

FIG. 12C shows quantification of Western blot images indicating decreased CB1R signaling after chronic WIN treatment. WT mice were treated with either daily WIN or vehicle for 14 d, and then subject to an acute dosage of WIN 1 h prior to collection of brain samples.

Figure 12D:
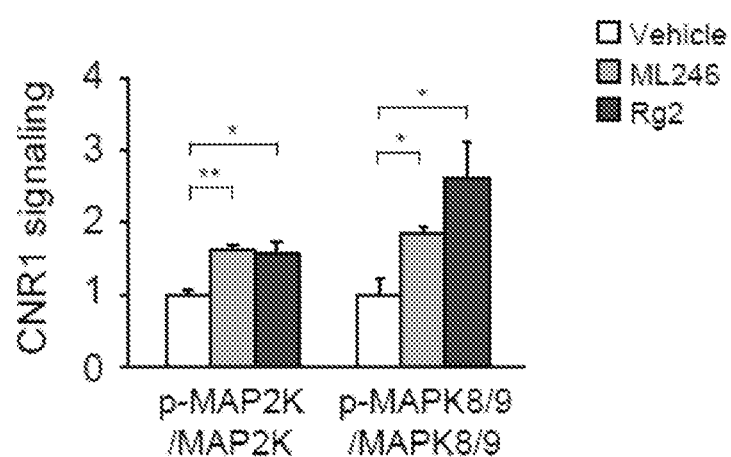

FIG. 12D shows quantification of Western blot analyses on brain lysates from WT mice that were treated as described for FIG. 12A, and then received an acute dosage of WIN 1 h prior to Western blot analyses on brain lysates.

Figure 12E:
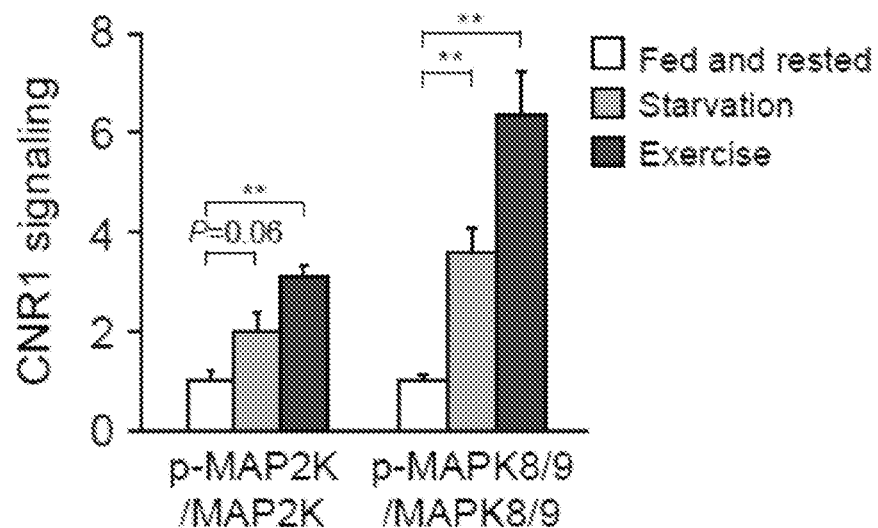

FIG. 12E shows quantification of Western blot analyses on brain lysates from WT mice that were treated as described for FIG. 12B, and injected with acute WIN 1 h prior to Western blot analyses on brain lysates. Western blot images (upper) and quantification (lower) of 3 mice in each group are shown. Results represent mean±s.e.m. *P<0.05, P<0.01, *P<0.001 (t-test).

Figure 13A:
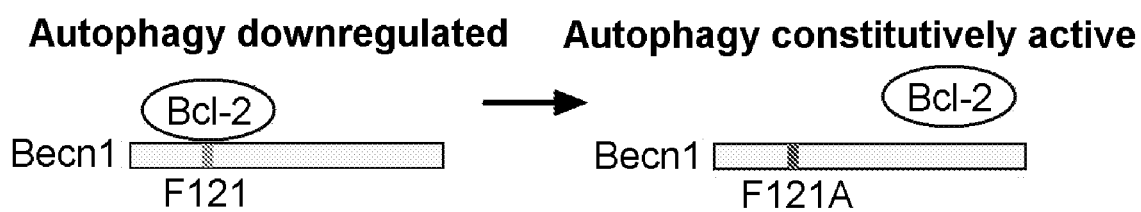

FIG. 13A shows a schematic representation of the strategy for hyperactive autophagy via the $Becn1^{F121A}$ knockin allele. F 121A blocks binding of BECN1 with its inhibitor BCL2, which leads to upregulated BECN1 function and constitutively high autophagy.

Figure 13B:
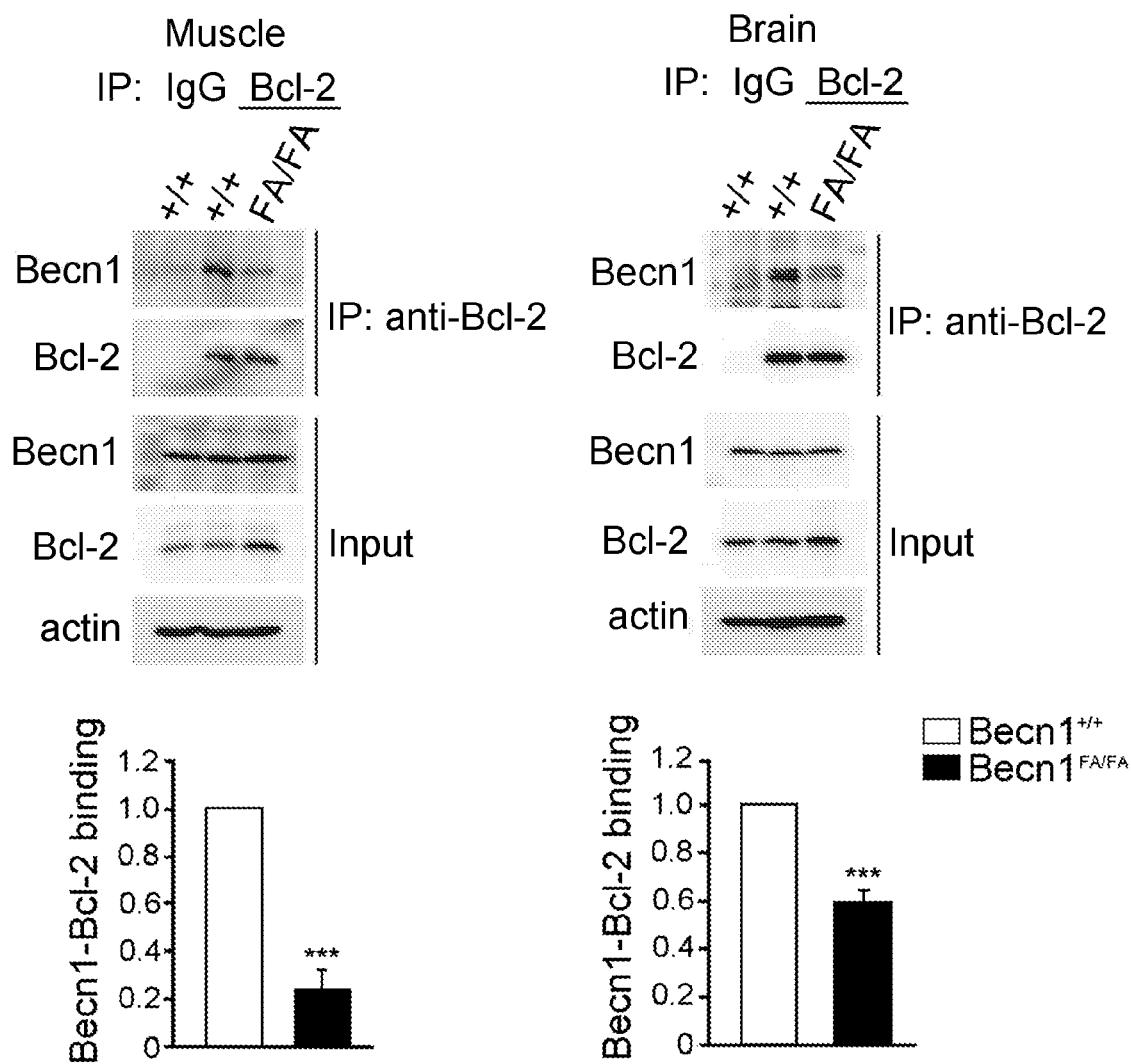

FIG. 13B shows co-immunoprecipitation of BECN1 by BCL2 in skeletal muscle and brain tissues from wild-type (WT) and $Becn1^{F121A}$ mice. Less $Becn1^{F121A}$ is immunoprecipitated by BCL2 than WT BECN1, quantified by the BECN1/BCL2 ratio in the IP samples from 3 independent experiments. FA/FA, $Becn1^{F121A}$ homozygous knock-in mice. ***, P<0.001, t test.

Figure 14A:
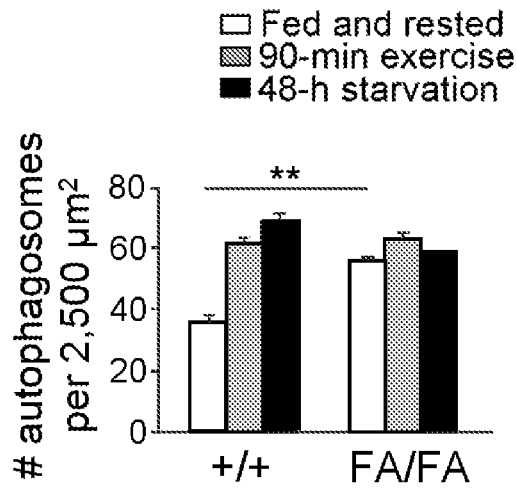

FIG. 14A shows quantification of GFP-LC3 puncta (autophagosomes) in skeletal muscle of GFP-LC3 $Becn1^{+/+}$ and GFP-LC3 $Becn1^{FA/FA}$ mice at non-autophagy-inducing conditions (fed and rested), after 90-min exercise, or after 48 hours of starvation. Scale bar: 25 μm. Results represent mean±s.e.m. 15 N=5. , P<0.05, , P<0.01, t test.

Figure 14B:
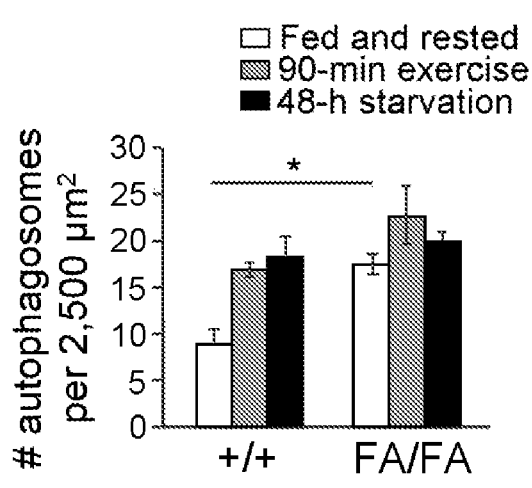

FIG. 14B shows quantification of GFP-LC3 puncta (autophagosomes) in brain of GFP-LC3 $Becn1^{+/+}$ and GFP-LC3 $Becn1^{FA/FA}$ mice at non-autophagy-inducing conditions (fed and rested), after 90-min exercise, or after 48 hours of starvation. Scale bar: 25 μm. Results represent mean±s.e.m. 15 N=5. *, P<0.05, **, P<0.01, t test.

Figure 14C:
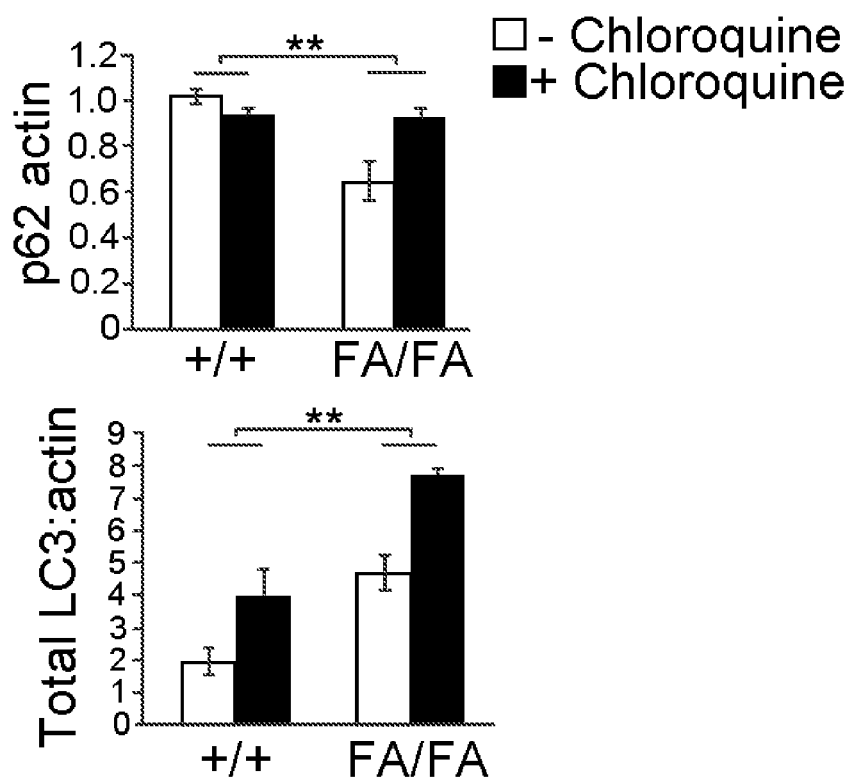

FIG. 14C shows quantification of Western blot analysis of LC3 and p62 levels in skeletal muscle from $Becn1^{+/+}$ and $Becn1^{FA/FA}$ mice injected with one dose of PBS or 50 mg/kg lysosomal inhibitor chloroquine. The autophagy flux is measured by the difference in the p62 and LC3 levels between mice injected with PBS and with chloroquine. Results represent mean±s.e.m. N=3. **, P<0.01, two-way ANOVA for comparison of magnitude of changes between different groups in mice of different genotypes.

Figure 15A:
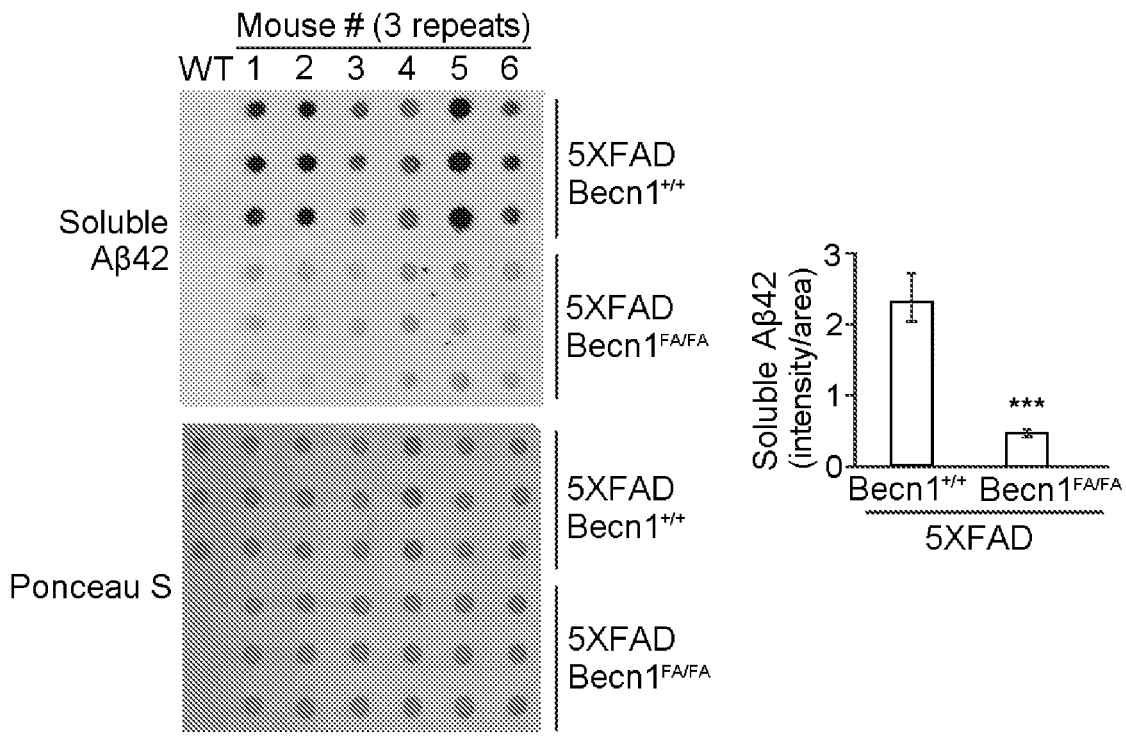

FIG. 15A shows dot-blot assays and quantification of soluble (Aβ42 levels in homogenated brain samples of 6-month old 5XFAD $Becn1^{+/+}$ and 5XFAD $Becn1^{FA/FA}$ mice, immunostained with anti-Aβ42 antibody. Total protein loading was labeled by Ponceau S. Triplicate experiments from 6 mice in each group were shown. ***, P<0.001, t test.

Figure 15B:
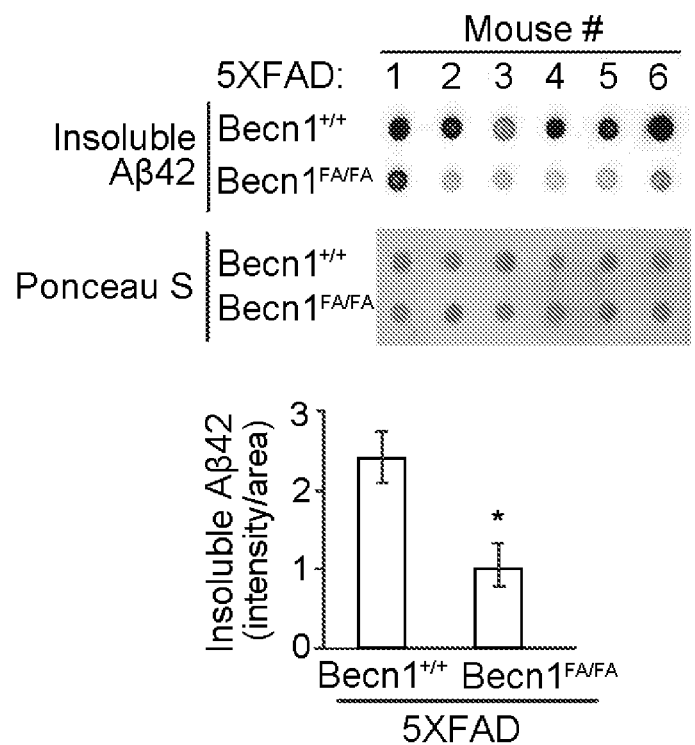

FIG. 15B shows dot-blot assays and quantification of insoluble Aβ42 levels in homogenated brain samples of 6-month old 5XFAD $Becn1^{+/+}$ and 5XFAD $Becn1^{+/+}$ mice, immunostained with anti-Aβ42 antibody. Total protein loading was labeled by Ponceau S. Triplicate experiments from 6 mice in each group were shown. ***, P<0.001, t test.

Figure 15C:
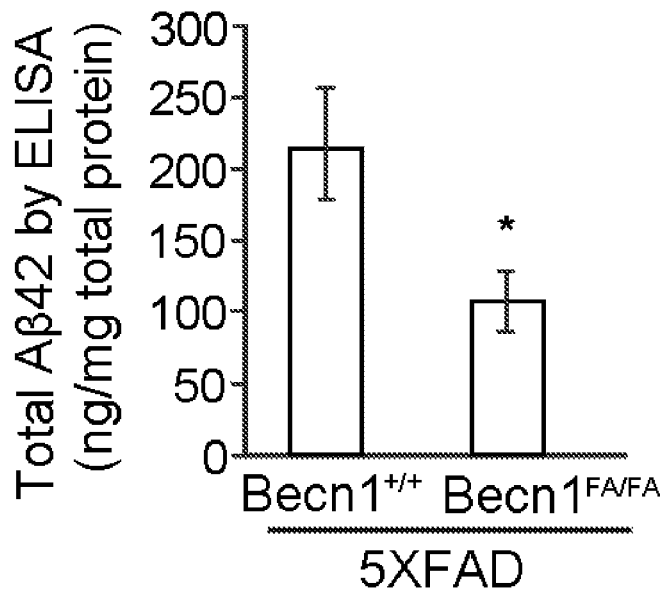

FIG. 15C shows ELISA analyses of total (soluble and insoluble) Aβ42 levels in the cortex of 6-month old 5XFAD Becn1$^{+/+}$ and 5XFAD Becn1$^{FA/FA}$ mice. N=7.

Figure 15D:
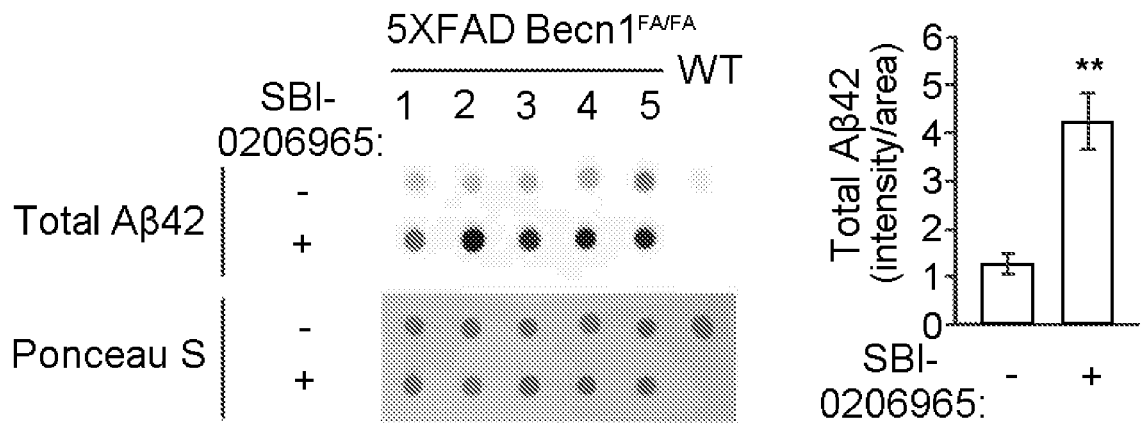

FIG. 15D shows Dot-blot assays and quantification of total Aβ42 levels in homogenated brain samples of 6-month old 5XFAD Becn1$^{FA/FA}$ mice treated with the autophagy inhibitor SBI-0206965 or vehicle once per day for 7 days. Total protein loading was labeled by Ponceau S. N=5. **, P<0.01, t test.

Figure 15E:
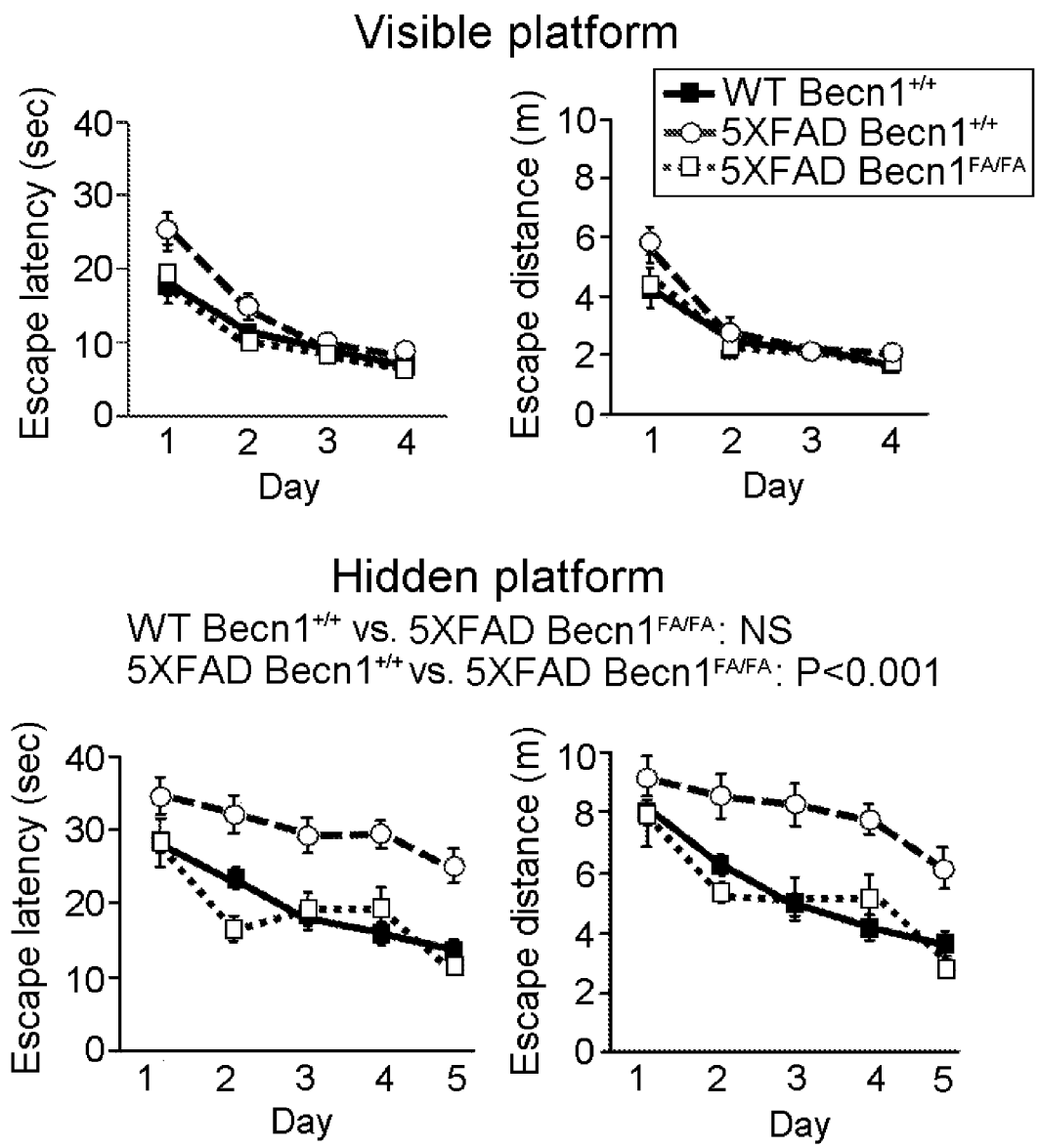

FIG. 15E shows Morris water maze test of 6-month old WT, 5XFAD Becn1$^{+/+}$ and 5XFAD Becn1$^{FA/FA}$ mice. Escape latency and total distance traveled in visible platform test and hidden platform test are shown. N=1 1-20. Results represent mean±s.e.m. Two-way repeated measures ANOVA.

Figure 16:
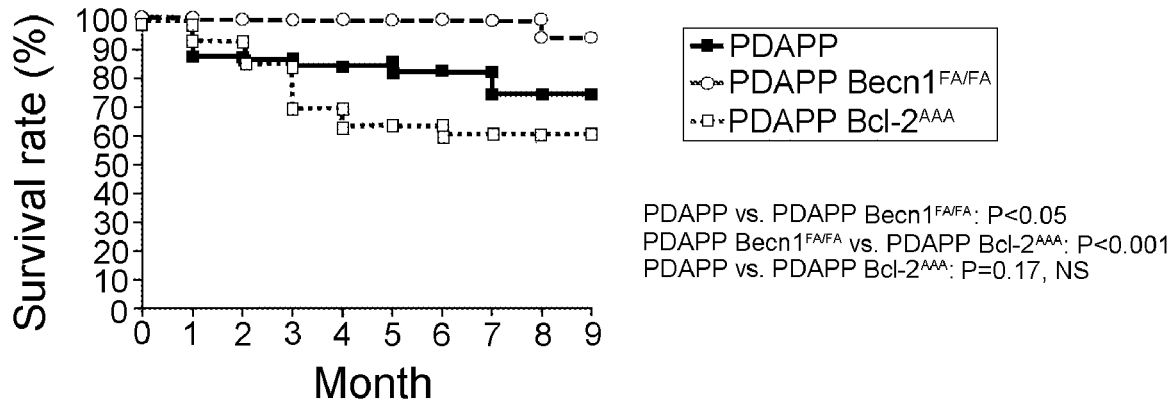

FIG. 16 shows the Kaplan-Meier survival curve of PDAPP mice with normal (PDAPP, N=51), hyperactive (PDAPP Becn1$^{FA/FA}$ N=34), or deficient (PDAPP Bcl2$^{AAA}$, N=33) autophagy monitored over time for 9 months. Statistical significance was analyzed by the log-rank test.

Figure 17A:
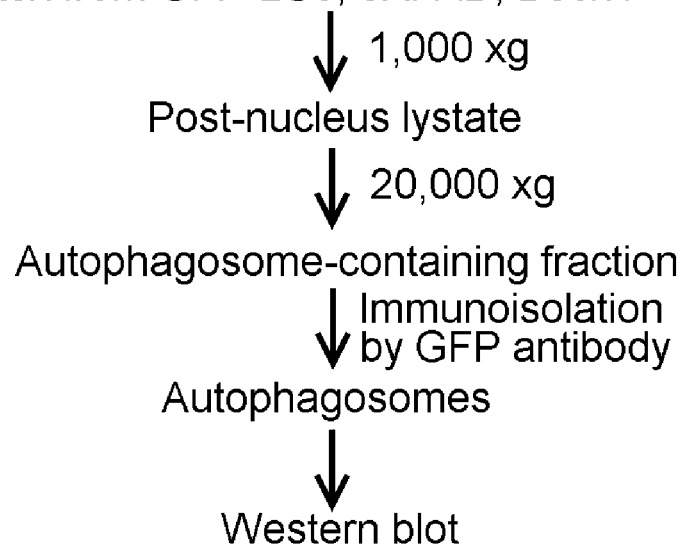

FIG. 17A shows a scheme of immunoisolation of autophagosomes from brain of 12-week old 5XFAD Becn1$^{FA/FA}$ mice expressing GFP-LC3. Briefly, post-nucleus extracts of the brain lysates were obtained by centrifugation at a low speed of 1,000×g. Autophagosomes were enriched by centrifugation at a high speed of 20,000×g, and pulled down by an anti-GFP antibody using magnetic beads.

Figure 17B:
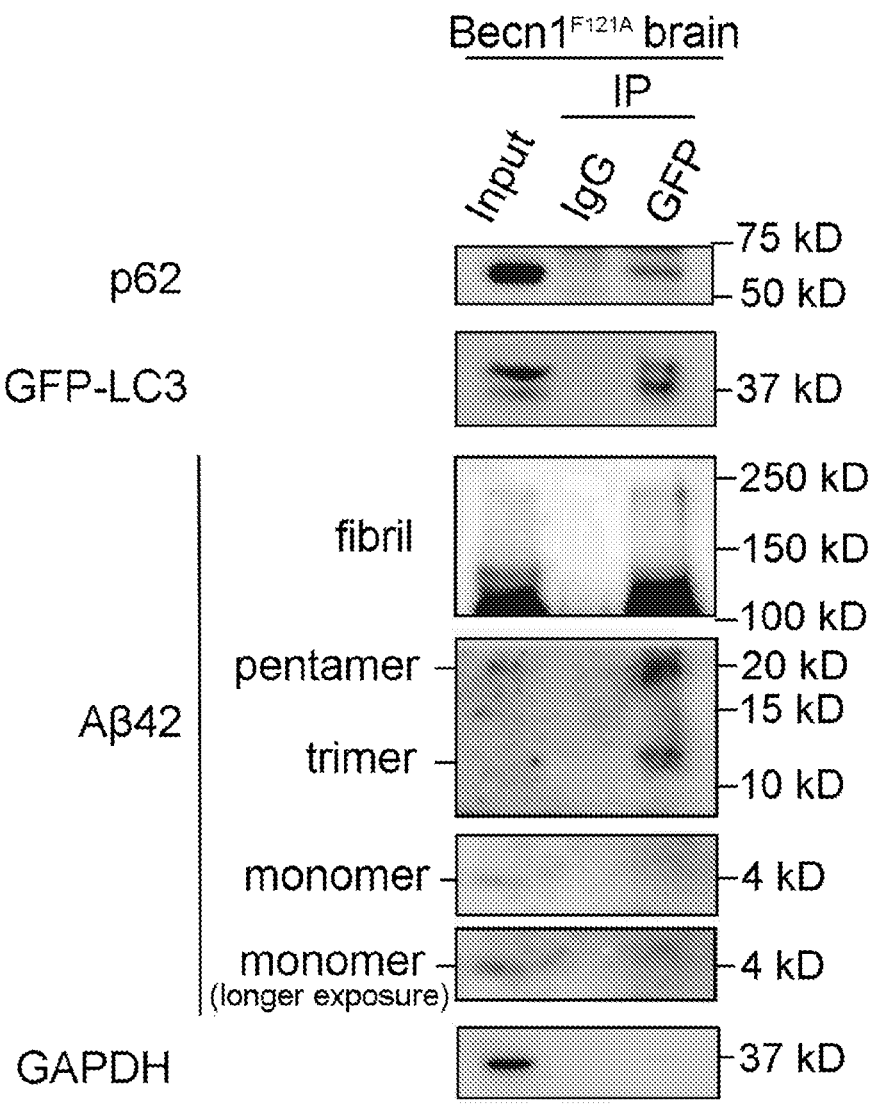

FIG. 17B shows Western blot detection of Aβ42 fibrillar and oligomeric species inside autophagosomes immunoprecipitated by GFP antibody as in the scheme. A known autophagy cargo p62 serves as a positive control, and a cytosolic enzyme GAPDH is a negative control.

Figure 18A:
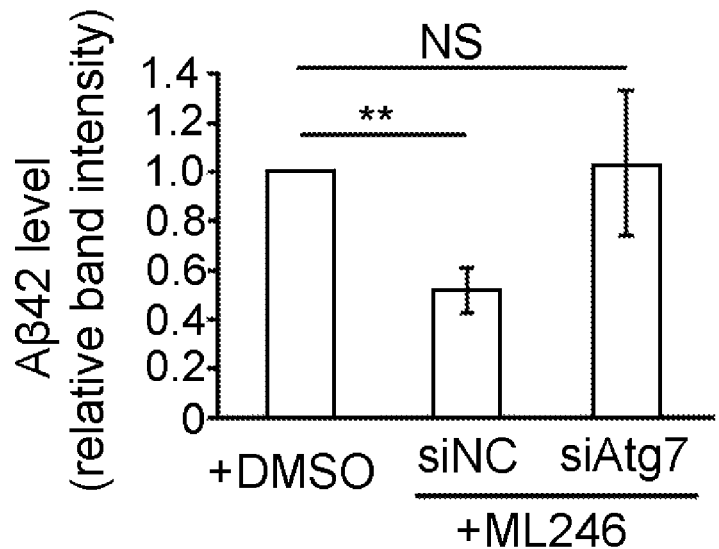

FIG. 18A shows quantification of secreted Aβ42 levels in conditioned media of HEK293 cells stably expressing APP treated with vehicle (DMSO) or ML246 for 24 h, immunostained with anti-Aβ42 antibody. Cells were transfected with non-targeting control (NC) or ATG7 siRNA 24 h prior to ML246 treatment. Results are quantified from 4 independent experiments.

Figure 18B:
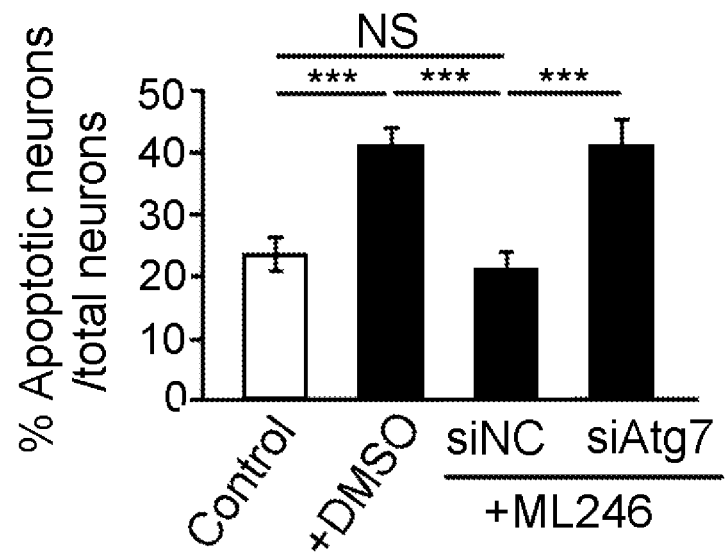

FIG. 18B shows quantification (right) of TUNEL signals (red) in WT primary cortical neurons treated with conditioned media from (B) for 24 h. Nuclei were stained with DAPI. Scale bar, 100 μm. N=10 fields (each field containing 20-30 neurons).

Figure 18C:
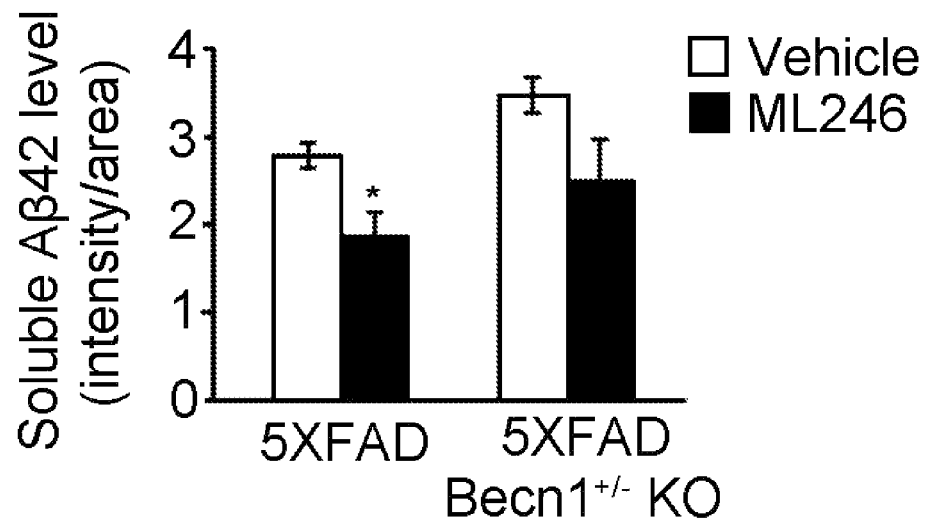

FIG. 18C shows quantification of dot-blot assays on soluble Aβ42 levels in brain samples of 6-month old 5XFAD and 5XFAD Becn1$^{+/-}$ KO mice after 5 weeks of ML246 treatment, immunostained with anti-Aβ42 antibody. Total protein loading was labeled by Ponceau S. Triplicate experiments from 4-5 mice in each group were shown. Results represent mean±s.e.m. NS, not significant; *, P<0.05; , P<0.01; *, P<0.001, t test.

Figure 18D:
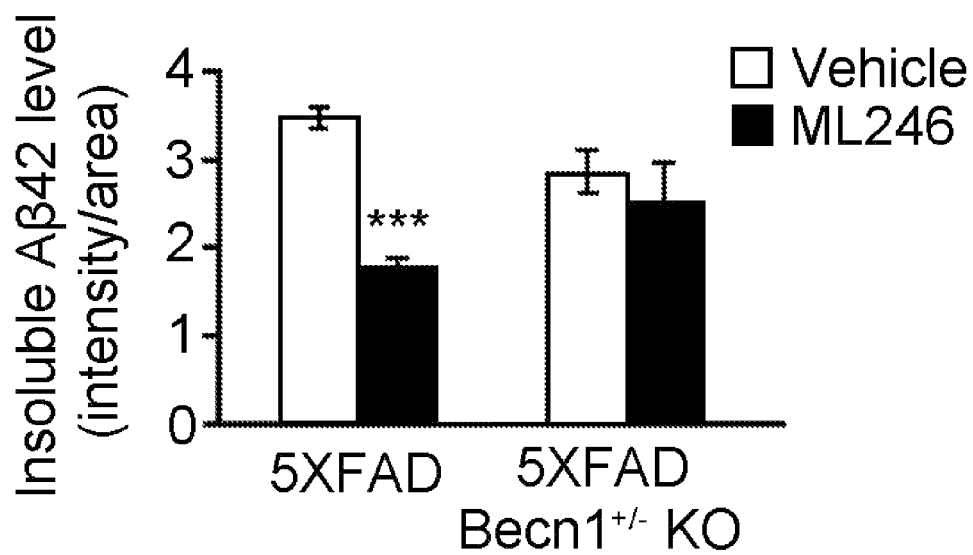

FIG. 18D shows quantification of dot-blot assays on insoluble (FIG. 18D) Aβ42 levels in brain samples of 6-month old 5XFAD and 5XFAD Becn1$^{+/-}$ KO mice after 5 weeks of ML246 treatment, immunostained with anti-Aβ42 antibody. Total protein loading was labeled by Ponceau S. Triplicate experiments from 4-5 mice in each group were shown. Results represent mean±s.e.m. NS, not significant; *, P<0.05; , P<0.01; *, P<0.001, t test.

Figure 19A:
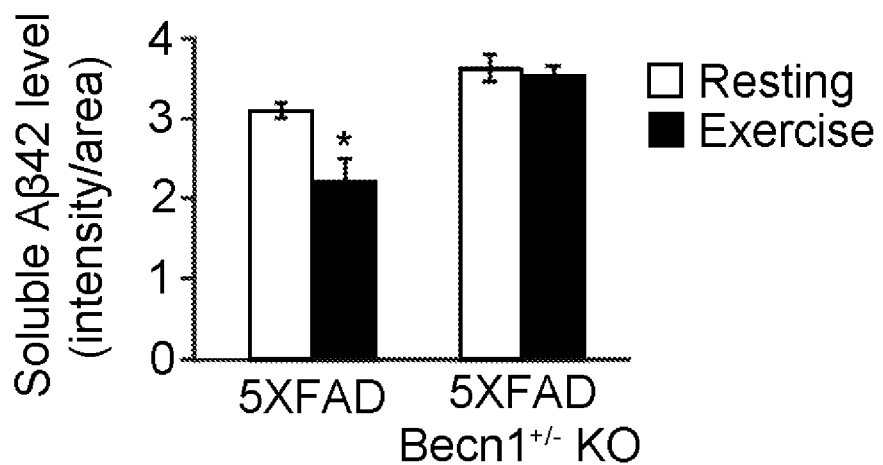

FIG. 19A shows quantification of dot-blot assays on soluble Aβ42 levels in brain samples of 6-month old 5XFAD and 5XFAD Becn1$^{+/-}$ KO mice after 4 months of voluntary running, immunostained with anti-Aβ42 antibody. Total protein loading was labeled by Ponceau S. Triplicate experiments from 4-5 mice in each group were shown.

Figure 19B:
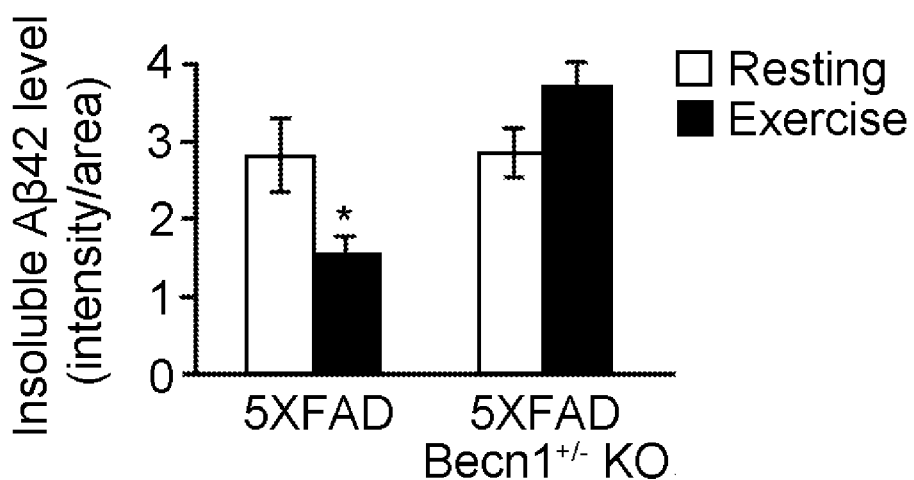

FIG. 19B shows quantification of dot-blot assays on insoluble Aβ42 levels in brain samples of 6-month old 5XFAD and 5XFAD Becn1$^{+/-}$ KO mice after 4 months of voluntary running, immunostained with anti-Aβ42 antibody. Total protein loading was labeled by Ponceau S. Triplicate experiments from 4-5 mice in each group were shown.

Figure 19C:
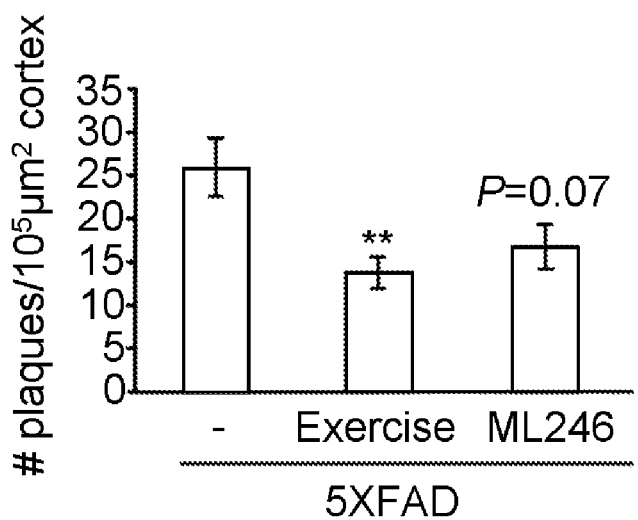

FIG. 19C shows quantification of amyloid deposits stained by Thioflavin S in brain of 6-month old 5XFAD mice, and 5XFAD mice subject to 5 weeks of ML246 treatment or 4 months of voluntary exercise. Scale bar: 500 μm. Results represent mean±s.e.m. N=6-8. *, P<0.05; **, P<0.01, t test.

Figure 19D:
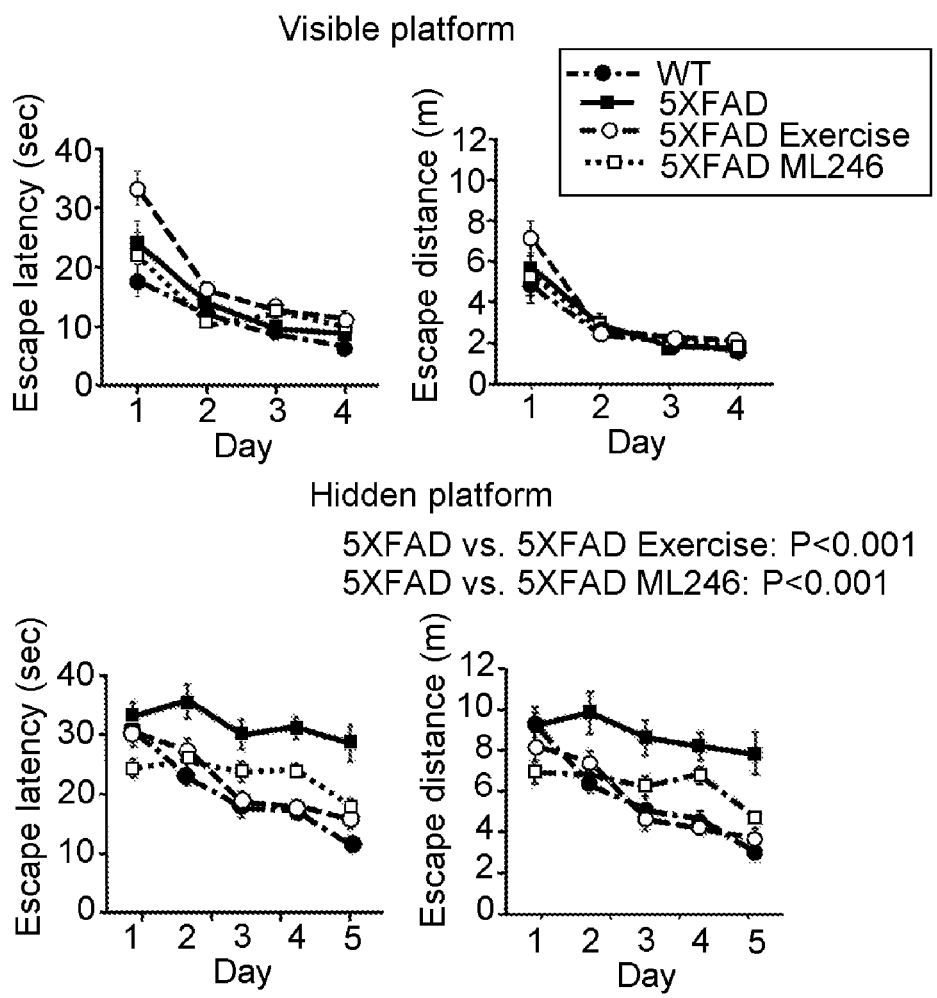

FIG. 19D shows the results of the Morris water maze test of 6-month old WT, 5XFAD, and 5XFAD mice after 5 weeks of ML246 treatment or 4 months of voluntary running. Escape latency and total distance traveled in visible platform test and hidden platform test are shown. N=10-11. Results represent mean±s.e.m. Two-way repeated measures ANOVA.

Figure 20A:
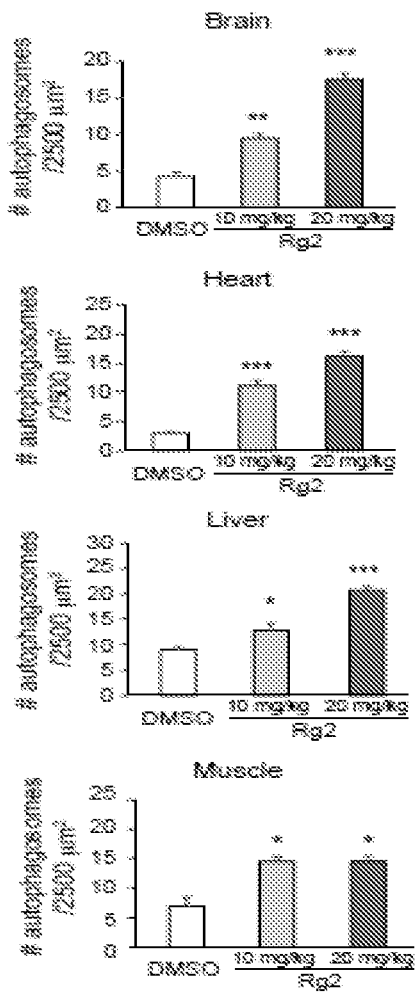

FIG. 20A shows quantification of GFP-LC3 puncta in the indicated organs of GFP-LC3 transgenic mice injected with vehicle (DMSO) or Rg2 once daily for 3 d. Results represent mean±s.e.m. Statistics compare each value to the one with DMSO treatment. *, P<0.05; , P<0.01; *, P<0.001, t test. Scale bar: 20 μm.

Figure 20B:
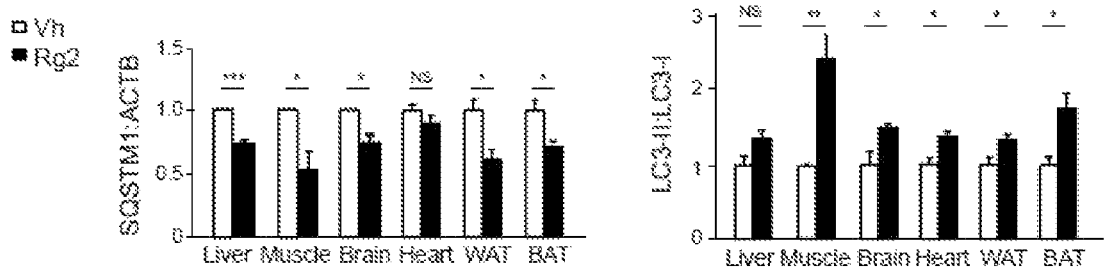

FIG. 20B shows quantification of Western blots of SQSTM1 and LC3 in the indicated organs of mice injected with vehicle (Vh) or Rg2. WAT, white adipose tissue; BAT, brown adipose tissue.

Figure 21A:
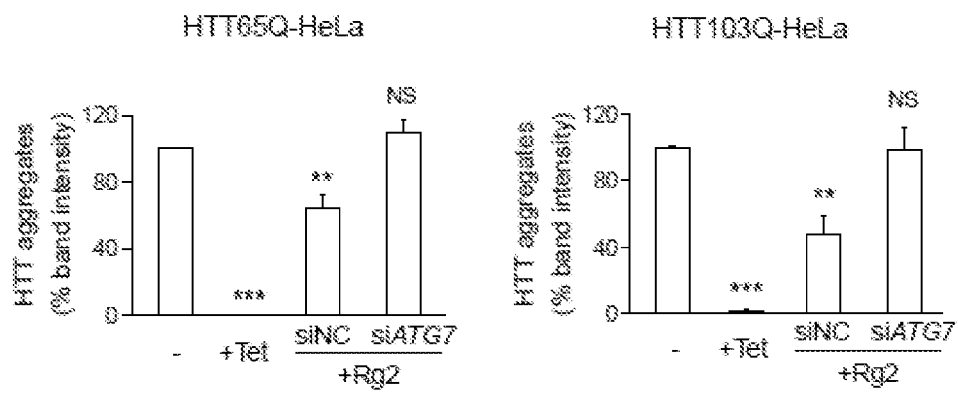

FIG. 21A shows quantification of filter trap assay of stable HeLa cells conditionally expressing HTT25Q-CFP, HTT65Q-CFP or HTT103Q-CFP in a Tet-off system, in the presence or absence of Rg2 or the indicated siRNA. Cells were transfected with nontargeting control (NC) or ATG7 siRNA 24 h prior to Rg2 treatment for another 24 h. HTT aggregates were analyzed by lysate filtration through 0.2 μm nitrocellulose membrane. Cells treated with tetracycline served as negative control.

Figure 21B:
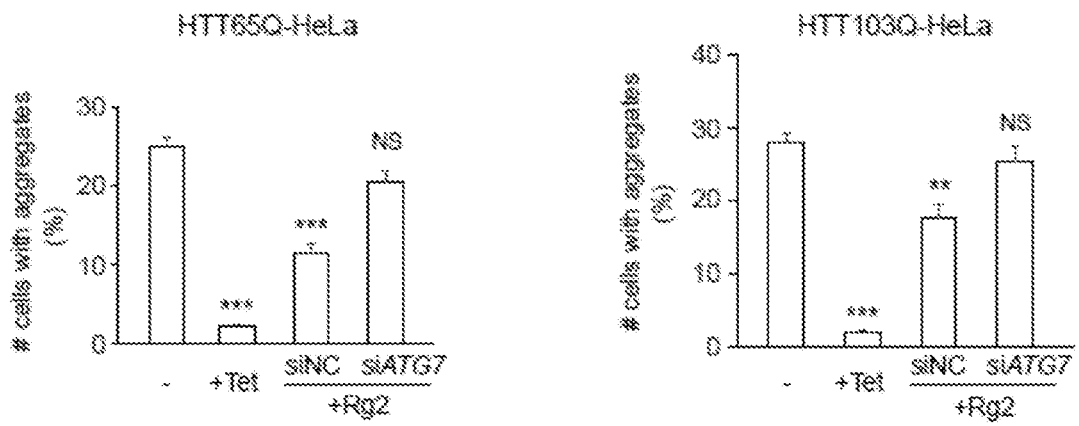

FIG. 21B shows quantification of inclusions formed by CFP-tagged polyglutamine HTT in cells as in FIG. 21A. Blue, DAPI. Results represent mean±s.e.m. Scale bar: 20 μm. Statistics compare each value to the one under the "-" condition. , P<0.01; *, P<0.001; NS, not significant, t test.

Figures 22A, 22B:
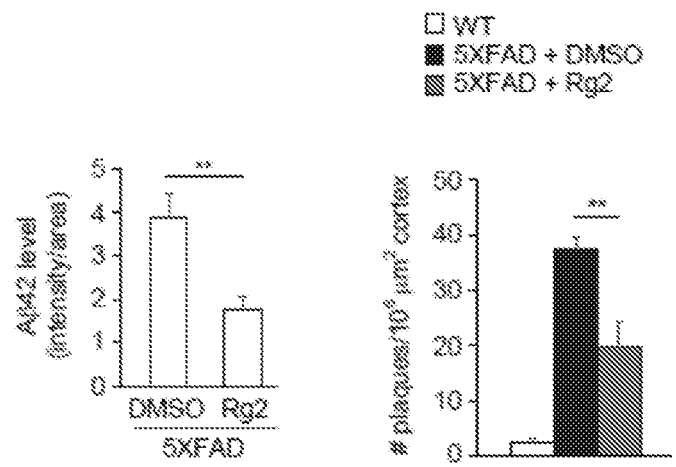

FIG. 22A shows quantification of dot-blot assays on total Aβ42 levels in brain samples of 5XFAD mice treated with vehicle (DMSO) or Rg2 for 4 months, immunostained with either anti-Aβ42 antibody or IgG as control. Total protein loading was labeled by Ponceau S. Triplicate experiments from 4 mice in each group were shown.

FIG. 22B shows quantification of amyloid deposits stained by thioflavin or anti-Aβ42 antibody in brain of 5XFAD mice treated with vehicle or Rg2 for 4 months.

Figure 22C:
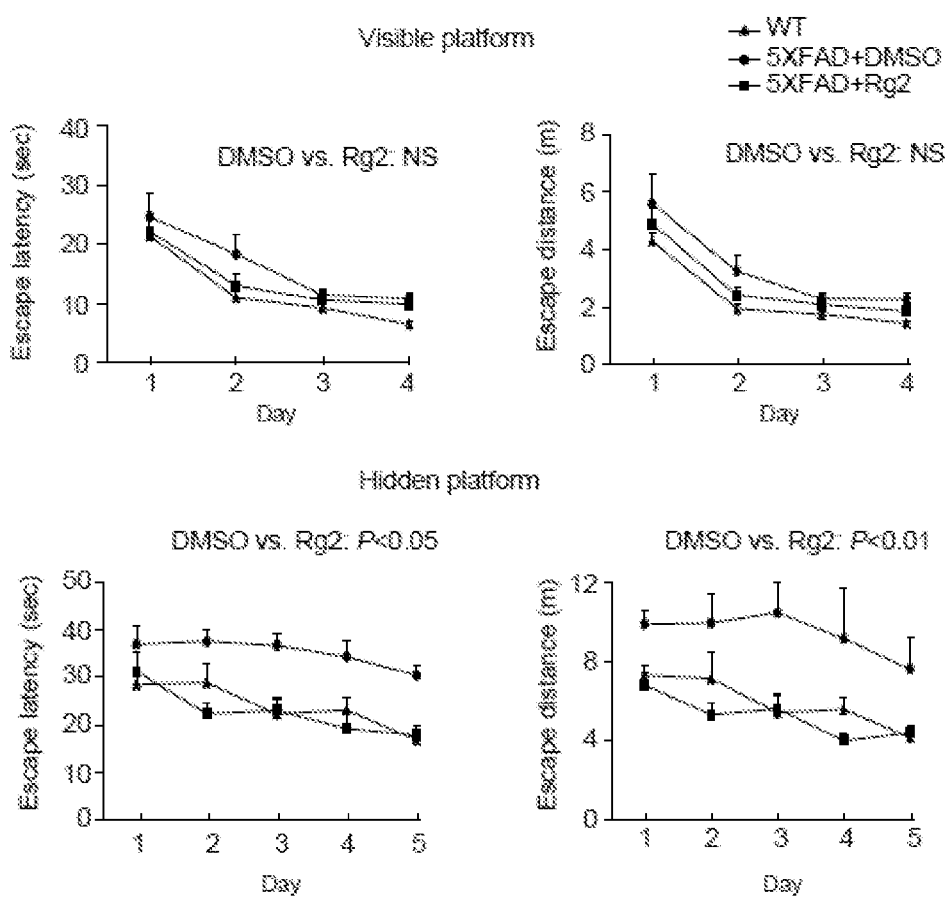

FIG. 22C shows results of the Morris water maze test of 5XFAD mice treated with vehicle or Rg2 for 4 months. Escape latency and total distance traveled in visible platform test and hidden platform test are shown. Results represent mean±s.e.m. Statistics were analyzed by the IBM SPSS Statistics Tools comparing differences between 2 curves.

Figure 22D:
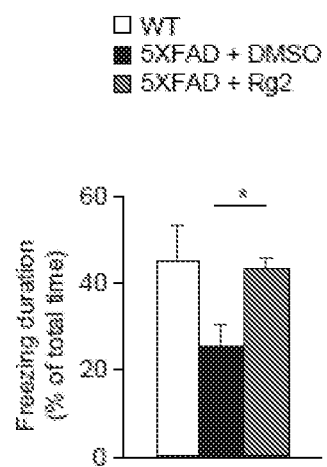

FIG. 22D shows the contextual fear conditioning test of 5XFAD mice treated with vehicle or Rg2 for 4 months. Fear conditioning training exposed mice to 2-s electrical foot shocks separated by 1-min interval through a grid floor at the bottom of the chamber. On the following day, the mice were returned to the same chamber and their movements were recorded with a video camera to test for contextual conditioning. Freezing (very low levels of movement) in the training environment indicate context-associated fear. WT mice without APP transgene were used as negative control in the above studies. N=8. *, $P<0.05$; **, $P<0.01$, t test.

DETAILED DESCRIPTION OF THE INVENTION

The invention provides a compound of formula (I):

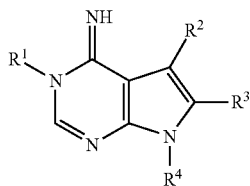

wherein $R^1$ is selected from the group consisting of alkyl, hydroxyalkyl, dialkoxyalkyl, trialkylsiloxyalkyl, thioalkyl, alkoxyalkyl, alkylthioalkyl, cycloalkyl, hydroxycycloalkyl, hydroxycycloalkylalkyl, thiocycloalkyl, alkoxycycloalkyl, alkylthiocycloalkyl, dialkylaminoalkyl, heterocyclyl, heterocyclylalkyl, heteroaryl, arylalkyl, arylalkylpiperidin-4-yl, arylpiperazinylalkyl, and heteroarylalkyl, $R^2$ is aryl or heteroaryl, $R^3$ is selected from the group consisting of H, alkyl, cycloalkyl, aryl, heteroaryl, arylalkyl, and heteroarylalkyl, $R^4$ is selected from the group consisting of alkyl, cycloalkyl, cycloalkylalkyl, aryl, heteroaryl, arylalkyl, and heteroarylalkyl, or a pharmaceutically acceptable salt thereof, wherein $R^1$, $R^2$, $R^3$, and $R^4$, other than H, are optionally substituted on the aryl and/or alkyl portion with one or more substituents selected from the group consisting of halo, alkyl, hydroxyalkyl, thioalkyl, alkoxy, alkylthioalkyl, alkoxycarbonyl, alkylthiocarbonyl, amino, alkylamino, dialkylamino, aminosulfonyl, hydroxyl, perfluoroalkoxy, alkylenedioxy, and alkylcarbonyl, ginsenoside Rg2 of structure (II):

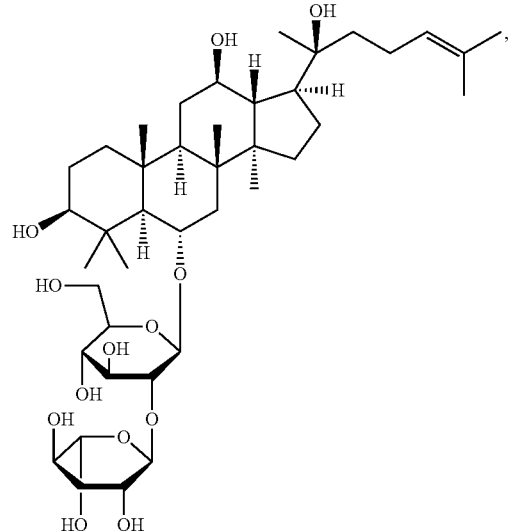

ginsenosides Re, Rf, or Rg1 of formula (III):

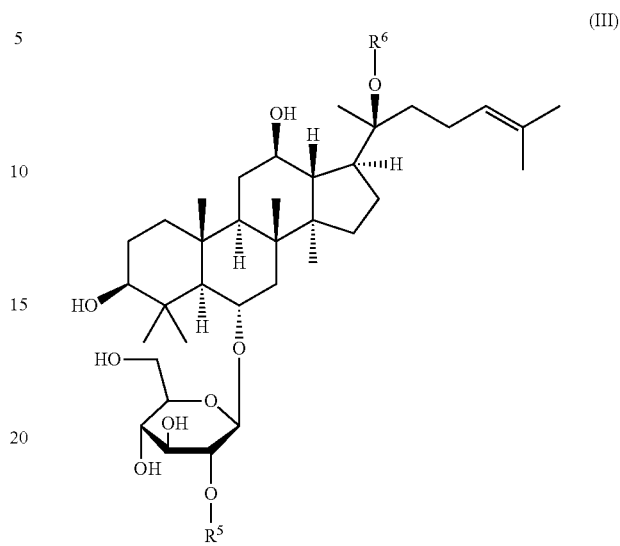

wherein $R^5$ is α-L-rhamnopyranosyl and $R^6$ is β-D-glucopyranosyl (ginsenoside Rc), $R^5$ is β-D-glucopyranosyl and $R^6$ is H (ginsenoside Rf), or $R^5$ is H and $R^6$ is β-D-glucopyranosyl (ginsenoside Rg1), ginsenosides Rb1, Rb2, or Rc of formula (IV):

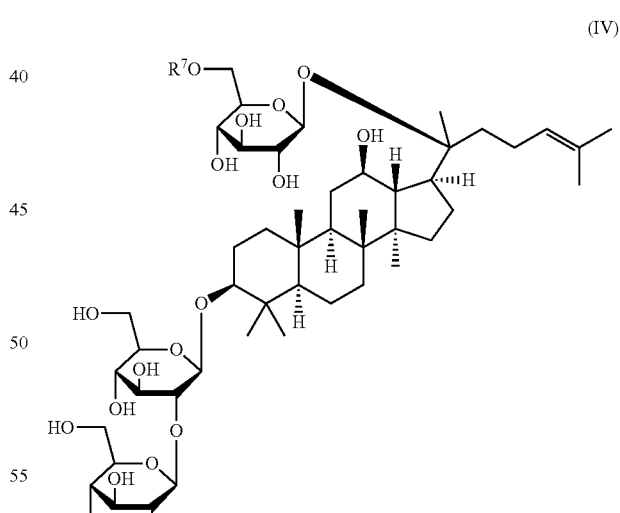

wherein $R^7$ is β-D-glucopyranosyl (ginsenoside Rb1), α-L-arabinopyranosyl (ginsenoside Rb2), or α-L-arabinofuranosyl (ginsenoside Rc), a compound of formula (V):

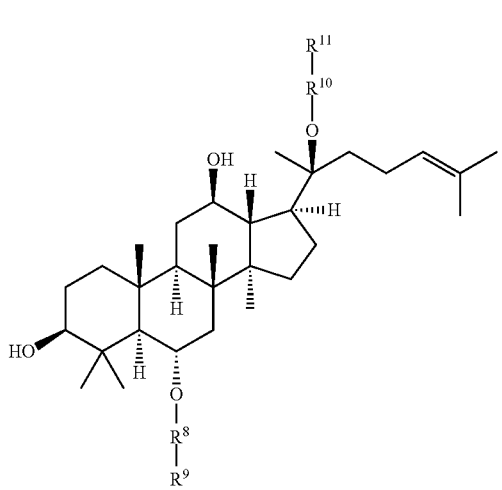

wherein $R^8$-$R^{11}$ are independently selected from the group consisting of β-D-glucopyranosyl, α-L-arabinopyranosyl, α-L-rhamnopyranosyl, and α-L-arabinofuranosyl, a compound of formula (VI):

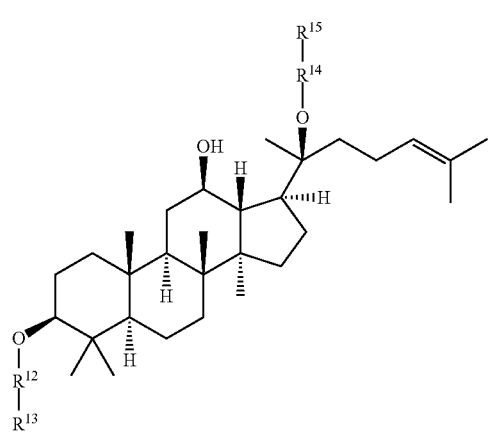

wherein $R^{12}$-$R^{15}$ are independently selected from the group consisting of β-D-glucopyranosyl, α-L-arabinopyranosyl, α-L-rhamnopyranosyl, and α-L-arabinofuranosyl, a compound of formula (VII):

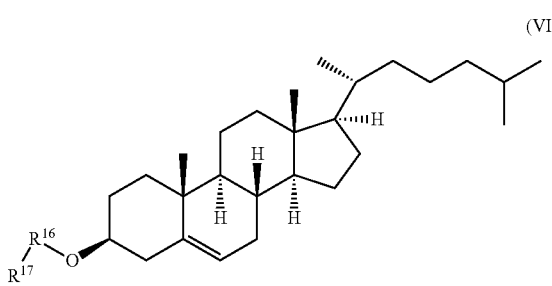

wherein $R^{16}$ and $R^{17}$ are independently selected from the group consisting of β-D-glucopyranosyl, α-L-arabinopyranosyl, α-L-rhamnopyranosyl, and α-L-arabino furanosyl, a compound of formula (VIII):

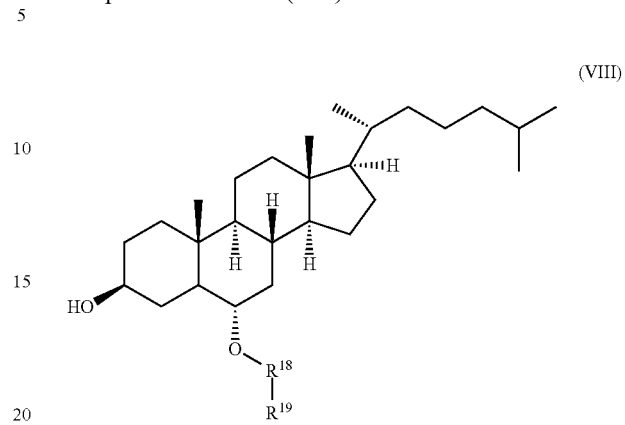

wherein $R^{18}$ and $R^{19}$ are independently selected from the group consisting of β-D-glucopyranosyl, α-L-arabinopyranosyl, α-L-rhamnopyranosyl, and α-L-arabinofuranosyl, a compound of formula (IX):

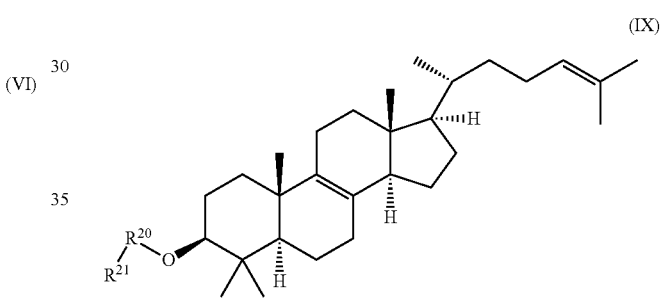

wherein $R^{20}$ and $R^{21}$ are independently selected from the group consisting of β-D-glucopyranosyl, α-L-arabinopyranosyl, α-L-rhamnopyranosyl, and α-L-arabinofuranosyl, or a compound of formula (X):

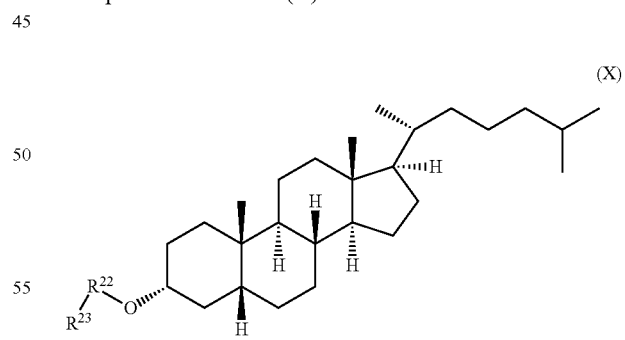

wherein $R^{22}$ and $R^{23}$ are independently selected from the group consisting of β-D-glucopyranosyl, α-L-arabinopyranosyl, α-L-rhamnopyranosyl, and α-L-arabinofuranosyl,
or any combination thereof,
for use in of treating or preventing a condition responsive to the induction of autophagy in a brain of a mammal in need thereof.

In accordance with an embodiment, $R^2$ is phenyl, optionally substituted with one or more substituents selected from halo, alkyl, hydroxyalkyl, thioalkyl, alkoxy, alkylthioalkyl, alkoxycarbonyl, alkylthiocarbonyl, amino, alkylamino, dialkylamino, and alkylcarbonyl.

In accordance with certain embodiments, $R^2$ is phenyl.

In accordance with any of the above embodiments, $R^3$ is phenyl, optionally substituted with one or more substituents selected from halo, alkyl, hydroxyalkyl, thioalkyl, alkoxy, alkylthioalkyl, alkoxycarbonyl, alkylthiocarbonyl, amino, alkylamino, dialkylamino, and alkylcarbonyl.

In accordance with any of the above embodiments, $R^4$ is benzyl, wherein the phenyl ring is optionally substituted with one or more substituents selected from alkyl, hydroxyalkyl, thioalkyl, alkoxy, alkylthioalkyl, alkoxycarbonyl, alkylthiocarbonyl, amino, alkylamino, dialkylamino, aminosulfonyl, hydroxyl, perfluoroalkoxy, and alkylcarbonyl.

In accordance with any of the above embodiments, $R^4$ is benzyl.

In accordance with any of the above embodiments, $R^1$ is a 5 or 6-membered heterocyclyl group having at least one hetero atom selected from O, N, and S; a hydroxy $C_1$-$C_7$ cycloalkyl group; a hydroxy $C_1$-$C_6$ alkyl group; a N,N-di ($C_1$-$C_6$ alkyl)amino $C_1$-$C_6$ alkyl group; a $C_1$-$C_6$ alkoxy $C_1$-$C_6$ alkyl group; a heteroaryl $C_1$-$C_6$ alkyl group; a heterocyclyl $C_1$-$C_6$ alkyl group; phenyl $C_1$-$C_6$ alkyl group wherein the phenyl ring is substituted with one or more $C_1$-$C_6$ alkoxy groups; N-benzyl piperazinyl; N-phenyl piperazinylalkyl; a phenyl $C_1$-$C_6$ alkyl group where the alkyl is substituted with a hydroxy group; or a 5 or 6 membered heteroarylamino $C_1$-$C_6$ alkyl group wherein the heteroaryl group has at least one hetero atom selected from O, N, and S.

In accordance with certain preferred embodiments, $R^1$ is selected from the following:

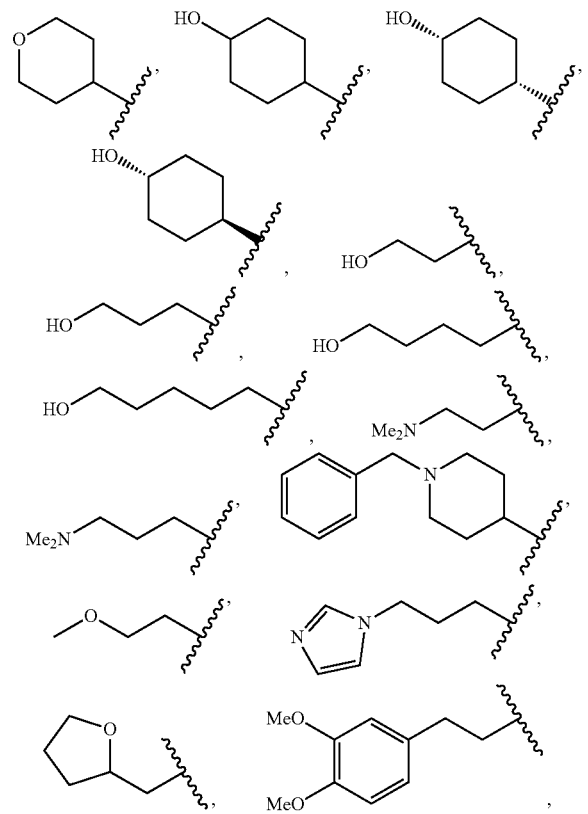
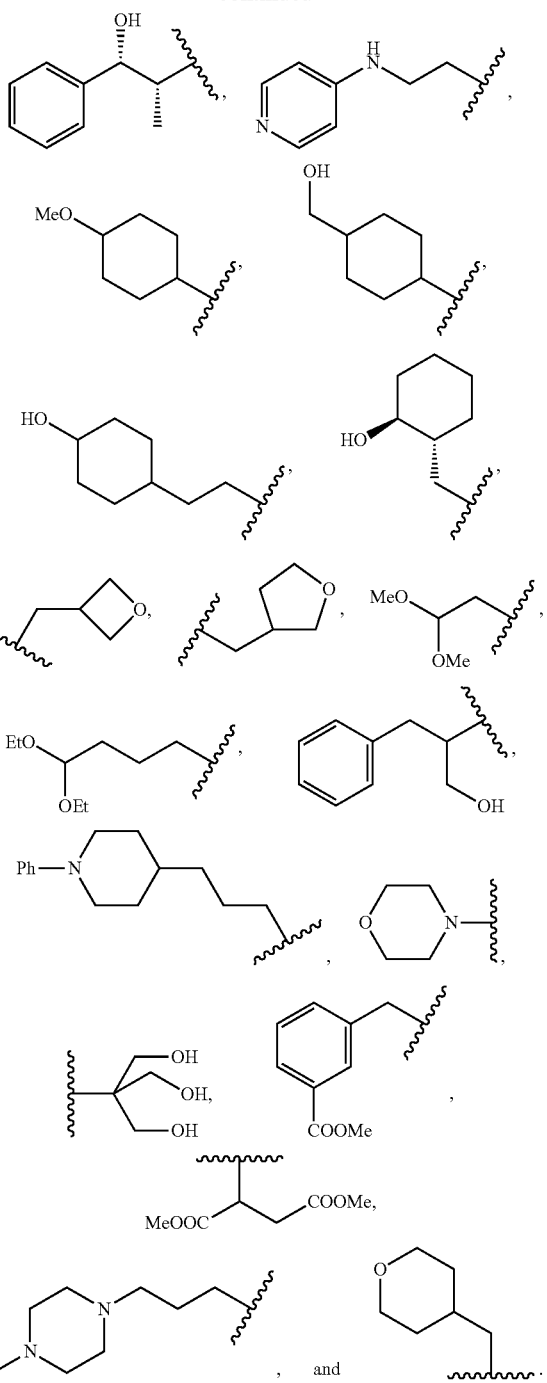

In accordance with certain specific embodiments, $R^2$ is phenyl, $R^3$ is phenyl, $R^4$ is benzyl, and $R^1$ is selected from the following:

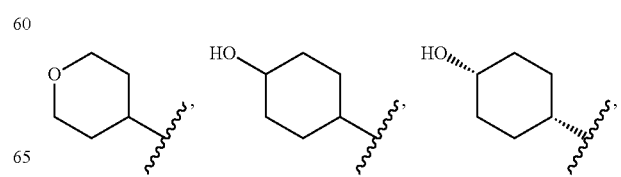

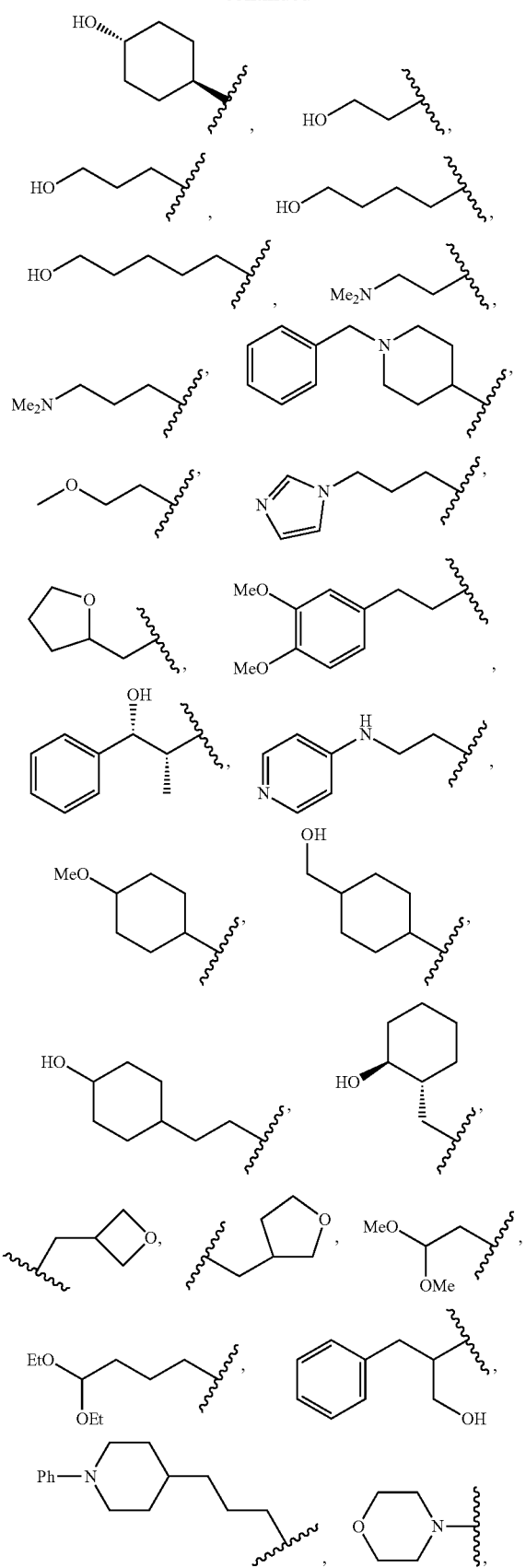

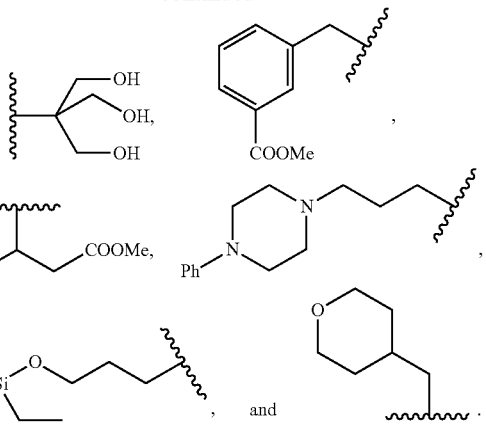

In accordance with certain embodiments, $R^4$ is 4-methoxybenzyl.

In accordance with certain preferred embodiments, $R^1$ is selected from the following:

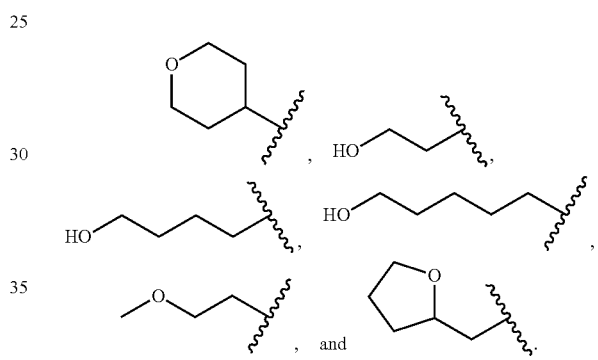

In accordance with certain specific embodiments, $R^2$ is phenyl, $R^3$ is phenyl, $R^4$ is 4-methoxybenzyl, and $R^1$ is selected from the following:

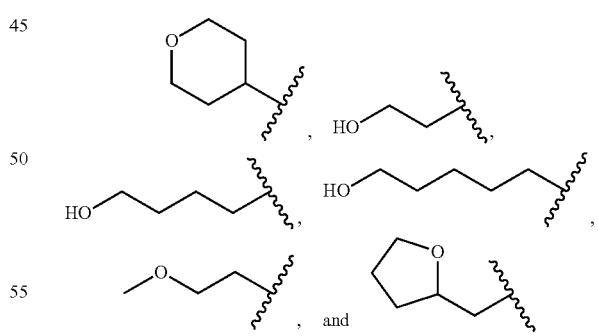

In accordance with any of the above embodiments, $R^4$ is phenylethyl, wherein the phenyl ring is optionally substituted with one or more substituents selected from alkyl, hydroxyalkyl, alkoxy, and alkoxycarbonyl.

In accordance with certain embodiments, $R^4$ is phenylethyl.

In accordance with certain preferred embodiments, $R^1$ is selected from the following:

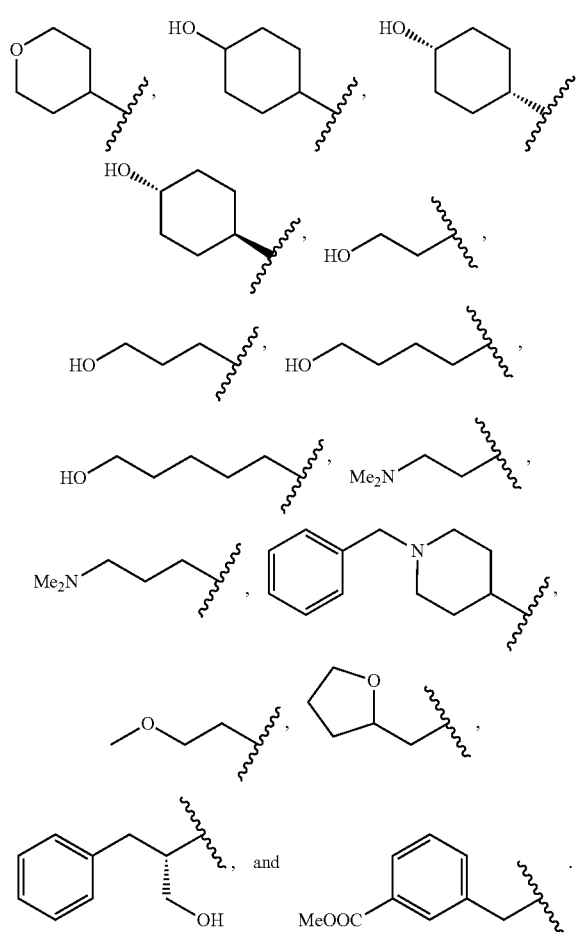

In accordance with certain specific embodiments, $R^2$ is phenyl, $R^3$ is phenyl, $R^4$ is phenylethyl, and $R^1$ is selected from the following:

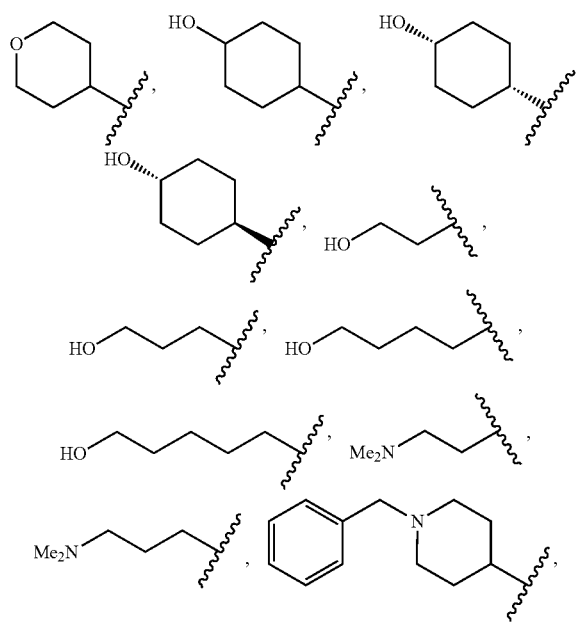

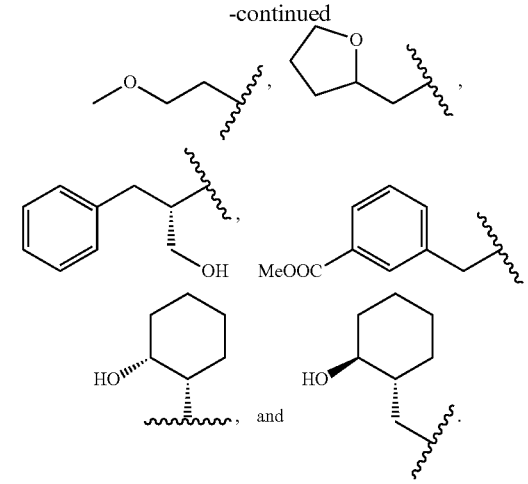

In accordance with certain embodiments, $R^4$ is heteroaryl $C_1$-$C_6$ alkyl.

In accordance with certain embodiments, $R^4$ is

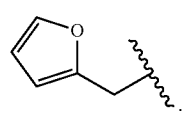 [SMILES: *Cc1ccco1]

In accordance with certain preferred embodiments, $R^1$ is selected from the following:

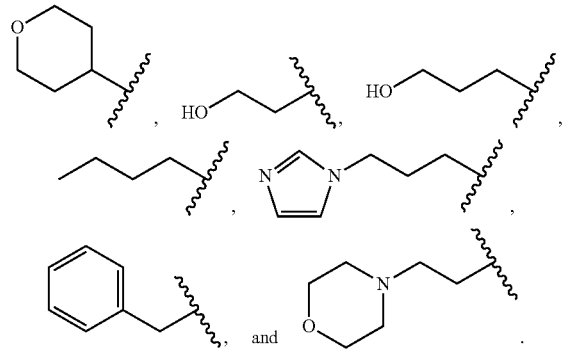

In accordance with certain specific embodiments, $R^2$ is phenyl, $R^3$ is phenyl, $R^4$ is

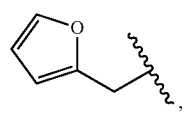

and $R^1$ is selected from the following:

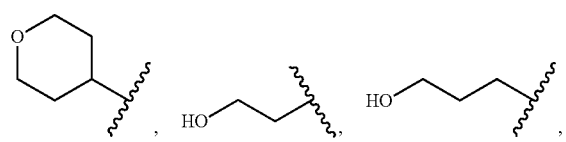

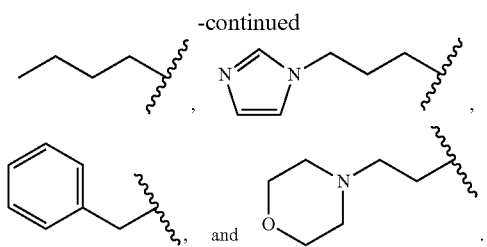

In accordance with certain embodiments, $R^4$ is selected from 4-aminosulfonylbenzyl, 4-trifluoromethoxybenzyl, 4-methoxybenzyl, and cyclopropylmethyl.

In accordance with certain preferred embodiments, $R^1$ is selected from the following:

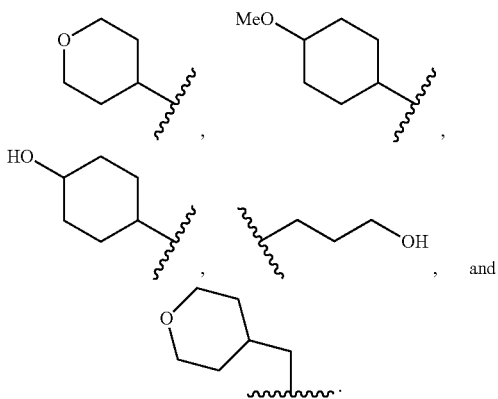

Referring now to terminology used generically herein, the term "alkyl" means a straight-chain or branched alkyl substituent containing from, for example, 1 to about 6 carbon atoms, preferably from 1 to about 4 carbon atoms, more preferably from 1 to 2 carbon atoms. Examples of such substituents include methyl, ethyl, propyl, isopropyl, n-butyl, sec-butyl, isobutyl, tert-butyl, pentyl, isoamyl, hexyl, and the like.

The term "alkenyl," as used herein, means a linear alkenyl substituent containing at least one carbon-carbon double bond and from, for example, about 2 to about 6 carbon atoms (branched alkenyls are about 3 to about 6 carbons atoms), preferably from about 2 to about 5 carbon atoms (branched alkenyls are preferably from about 3 to about 5 carbon atoms), more preferably from about 3 to about 4 carbon atoms. Examples of such substituents include vinyl, propenyl, isopropenyl, n-butenyl, sec-butenyl, isobutenyl, tert-butenyl, pentenyl, isopentenyl, hexenyl, and the like.

The term "cycloalkynyl," as used herein, means a linear alkynyl substituent containing at least one carbon-carbon triple bond and from, for example, 2 to about 6 carbon atoms (branched alkynyls are about 3 to about 6 carbons atoms), preferably from 2 to about 5 carbon atoms (branched alkynyls are preferably from about 3 to about 5 carbon atoms), more preferably from about 3 to about 4 carbon atoms. Examples of such substituents include ethynyl, propynyl, isopropynyl, n-butynyl, sec-butynyl, isobutynyl, tert-butynyl, pentynyl, isopentynyl, hexynyl, and the like.

The term "cycloalkyl," as used herein, means a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. The cyclic alkyl groups may be unsubstituted or further substituted with alkyl groups such as methyl groups, ethyl groups, and the like. The term "cycloalkylalkyl," as used herein, refers to an alkyl group linked to a cycloalkyl group and further linked to a molecule via the alkyl group.

The term "heterocyclyl," as used herein, refers to a monocyclic or bicyclic 5- or 6-membered ring system containing one or more heteroatoms selected from the group consisting of O, N, S, and combinations thereof. The heterocyclyl group can be any suitable heterocyclyl group and can be an aliphatic heterocyclyl group, an aromatic heterocyclyl group, or a combination thereof. The heterocyclyl group can be a monocyclic heterocyclyl group or a bicyclic heterocyclyl group. Suitable bicyclic heterocyclyl groups include monocyclic heterocyclyl rings fused to a $C_6$-$C_{10}$ aryl ring. When the heterocyclyl group is a bicyclic heterocyclyl group, both ring systems can be aliphatic or aromatic, or one ring system can be aromatic and the other ring system can be aliphatic as in, for example, dihydrobenzofuran. Non-limiting examples of suitable aromatic heterocyclyl groups include tetrahydrofuranyl, tetrahydropyranyl, tetrahydrothiopheneyl, pyrrolidinyl, piperidinyl, and morpholinyl. Non-limiting examples of suitable aromatic heterocyclyl groups include furanyl; thiopheneyl; pyrrolyl; pyrazolyl; imidazolyl; 1,2,3-triazolyl; 1,2,4-triazolyl; isoxazolyl; oxazolyl; isothiazolyl; thiazolyl; 1,3,4-oxadiazol-2-yl; 1,2,4-oxadiazol-2-yl; 5-methyl-1,3,4-oxadiazole; 3-methyl-1,2,4-oxadiazole; pyridinyl; pyrimidinyl; pyrazinyl; triazinyl; benzofuranyl; benzothiopheneyl; indolyl; quinolinyl; isoquinolinyl; benzimidazolyl; benzoxazolinyl; benzothiazolinyl; and quinazolinyl. The heterocyclyl group is optionally substituted with 1, 2, 3, 4, or 5 substituents as recited herein such as with alkyl groups such as methyl groups, ethyl groups, and the like, or with aryl groups such as phenyl groups, naphthyl groups and the like, wherein the aryl groups can be further substituted with, for example halo, dihaloalkyl, trihaloalkyl, nitro, hydroxy, alkoxy, aryloxy, amino, substituted amino, alkylcarbonyl, alkoxycarbonyl, arylcarbonyl, aryloxycarbonyl, thio, alkylthio, arylthio, and the like, wherein the optional substituent can be present at any open position on the heterocyclyl group.

The term "heterocyclylalkyl," as used herein, refers to an alkyl group linked to a heterocyclyl group and further linked to a molecule via the alkyl group.

The term "arylalkyl," as used herein, refers to an alkyl group linked to a $C_6$-$C_{10}$ aryl ring and further linked to a molecule via the alkyl group. The term "alkylaryl," as used herein, refers to a $C_6$-$C_{10}$ aryl ring linked to an alkyl group and further linked to a molecule via the aryl group.

The term "alkylcarbonyl," as used herein, refers to an alkyl group linked to a carbonyl group and further linked to a molecule via the carbonyl group, such as alkyl-C(═O)—. The term "alkoxycarbonyl," as used herein, refers to an alkoxy group linked to a carbonyl group and further linked to a molecule via the carbonyl group, such as alkyl-O—C(═O)—.

Whenever a range of the number of atoms in a structure is indicated (such as a $C_1$-$C_{12}$, $C_1$-$C_8$, $C_1$-$C_6$, $C_1$-$C_4$, or $C_2$-$C_{12}$, $C_2$-$C_8$, $C_2$-$C_6$, $C_2$-$C_4$ alkyl, alkenyl, alkynyl, etc.), it is specifically contemplated that any sub-range or individual number of carbon atoms falling within the indicated range also can be used. Thus, for instance, the recitation of a range of 1-8 carbon atoms (such as $C_1$-$C_8$), 1-6 carbon atoms (such as $C_1$-$C_6$), 1-4 carbon atoms (such as $C_1$-$C_4$), 1-3 carbon atoms (such as $C_1$-$C_3$), or 2-8 carbon atoms (such as $C_2$-$C_8$)

as used with respect to any chemical group (such as alkyl, alkylamino, etc.) referenced herein encompasses and specifically describes 1, 2, 3, 4, 5, 6, 7, 8, 9, 10, 11, or 12 carbon atoms, and combinations thereof, as appropriate, as well as any sub-range thereof (such as 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate). Similarly, the recitation of a range of 6-10 carbon atoms (such as, $C_6$-$C_{10}$) as used with respect to any chemical group (such as, aryl) referenced herein encompasses and specifically describes 6, 7, 8, 9, and/or 10 carbon atoms, as appropriate, as well as any sub-range thereof (such as, 6-10 carbon atoms, 6-9 carbon atoms, 6-8 carbon atoms, 6-7 carbon atoms, 7-10 carbon atoms, 7-9 carbon atoms, 7-8 carbon atoms, 8-10 carbon atoms, and/or 8-9 carbon atoms, etc., as appropriate).

The term "halo" or "halogen," as used herein, means a substituent selected from Group VIIA, such as, for example, fluorine, bromine, chlorine, and iodine.

The term "aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise 4n+2π electrons, according to Hückel's Rule.

In an embodiment, the compound is ginsenoside Rg2 of structure (II):

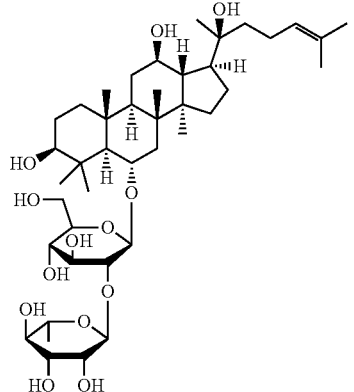

(II)

In certain embodiments, the compound is selected from the group consisting of ginsenosides Re, Rf, or Rg1 of formula (III):

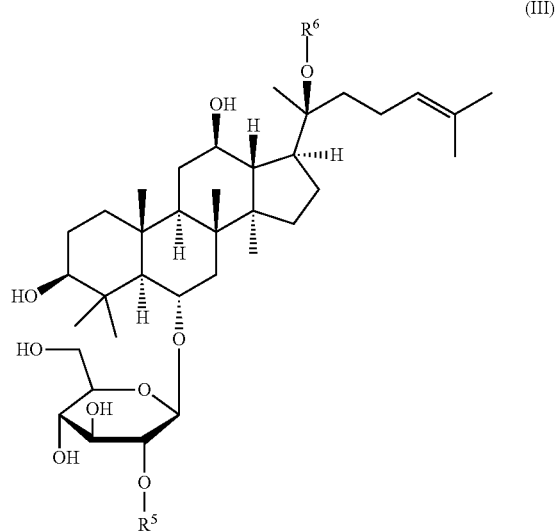

(III)

wherein $R^5$ is α-L-rhamnopyranosyl and $R^6$ is β-D-glucopyranosyl (ginsenoside Rc), $R^5$ is β-D-glucopyranosyl and $R^6$ is H (ginsenoside Rf), or $R^5$ is H and $R^6$ is β-D-glucopyranosyl (ginsenoside Rg1).

In certain embodiments, the compound is selected from the group consisting of ginsenosides Rb1, Rb2, or Rc of formula (IV):

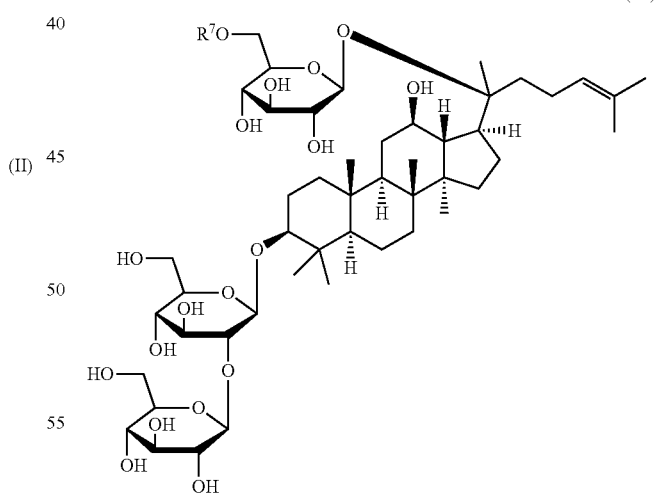

(IV)

wherein $R^7$ is β-D-glucopyranosyl (ginsenoside Rb1), α-L-arabinopyranosyl (ginsenoside Rb2), or α-L-arabinofuranosyl (ginsenoside Rc).

In certain embodiments, the compound is selected from the group consisting of a compound of formula (V):

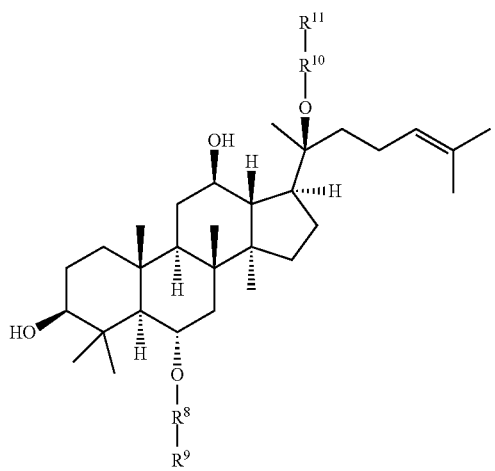

(V)

wherein $R^8$-$R^{11}$ are independently selected from the group consisting of β-D-glucopyranosyl, α-L-arabinopyranosyl, α-L-rhamnopyranosyl, and α-L-arabinofuranosyl.

In certain embodiments, the compound is selected from the group consisting of a compound of formula (VI):

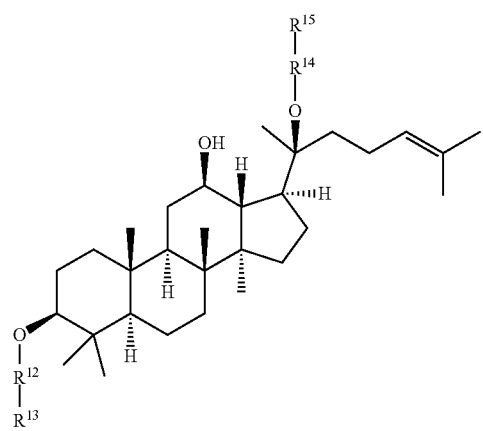

(VI)

wherein $R^{12}$-$R^{15}$ are independently selected from the group consisting of β-D-glucopyranosyl, α-L-arabinopyranosyl, α-L-rhamnopyranosyl, and α-L-arabinofuranosyl.

In certain embodiments, the compound is selected from the group consisting of a compound of formula (VII):

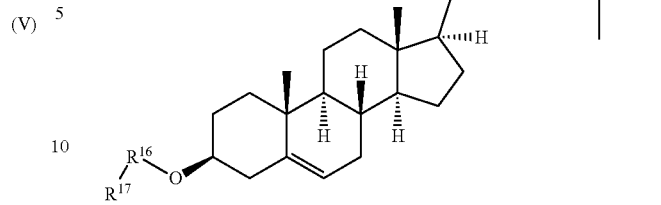

(VII)

wherein $R^{16}$ and $R^{17}$ are independently selected from the group consisting of β-D-glucopyranosyl, α-L-arabinopyranosyl, α-L-rhamnopyranosyl, and α-L-arabinofuranosyl.

In certain embodiments, the compound is selected from the group consisting of a compound of formula (VIII):

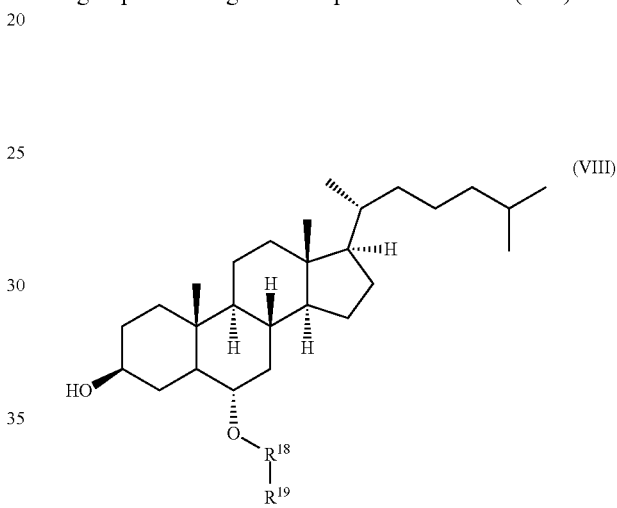

(VIII)

wherein $R^{18}$ and $R^{19}$ are independently selected from the group consisting of β-D-glucopyranosyl, α-L-arabinopyranosyl, α-L-rhamnopyranosyl, and α-L-arabinofuranosyl.

In certain embodiments, the compound is selected from the group consisting of a compound of formula (IX):

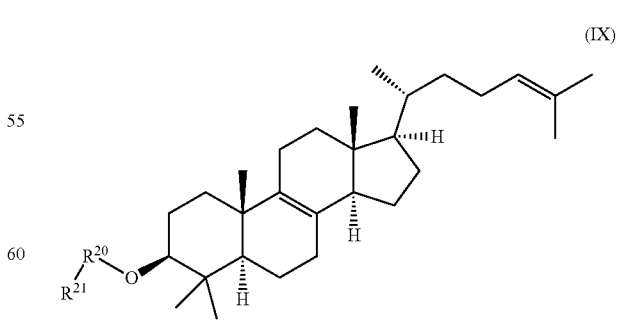

(IX)

wherein $R^{20}$ and $R^{21}$ are independently selected from the group consisting of β-D-glucopyranosyl, α-L-arabinopyranosyl, α-L-rhamnopyranosyl, and α-L-arabinofuranosyl.

In certain embodiments, the compound is selected from the group consisting of a compound of formula (X):

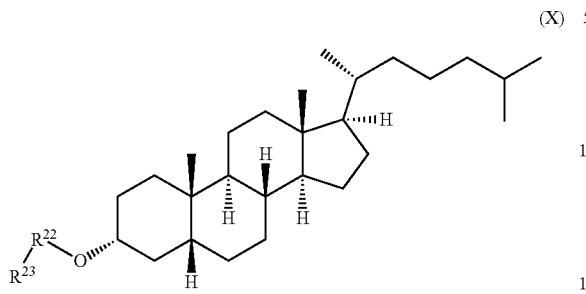

(X)

wherein $R^{22}$ and $R^{23}$ are independently selected from the group consisting of β-D-glucopyranosyl, α-L-arabinopyranosyl, α-L-rhamnopyranosyl, and α-L-arabinofuranosyl.

The phrase "pharmaceutically acceptable salt" is intended to include non-toxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media such as ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p. 1445, and *Journal of Pharmaceutical Science,* 66, 2-19 (1977).

Suitable bases include inorganic bases such as alkali and alkaline earth metal bases, such as those containing metallic cations such as sodium, potassium, magnesium, calcium and the like. Non-limiting examples of suitable bases include sodium hydroxide, potassium hydroxide, sodium carbonate, and potassium carbonate. Suitable acids include inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, maleic acid, tartaric acid, fatty acids, long chain fatty acids, and the like. Preferred pharmaceutically acceptable salts of inventive compounds having an acidic moiety include sodium and potassium salts. Preferred pharmaceutically acceptable salts of inventive compounds having a basic moiety (such as a dimethylaminoalkyl group) include hydrochloride and hydrobromide salts. The compounds of the present invention containing an acidic or basic moiety are useful in the form of the free base or acid or in the form of a pharmaceutically acceptable salt thereof.

It should be recognized that the particular counterion forming a part of any salt of this invention is usually not of a critical nature, so long as the salt as a whole is pharmacologically acceptable and as long as the counterion does not contribute undesired qualities to the salt as a whole.

It is further understood that the above compounds and salts may form solvates, or exist in a substantially uncomplexed form, such as the anhydrous form. As used herein, the term "solvate" refers to a molecular complex wherein the solvent molecule, such as the crystallizing solvent, is incorporated into the crystal lattice. When the solvent incorporated in the solvate is water, the molecular complex is called a hydrate. Pharmaceutically acceptable solvates include hydrates, alcoholates such as methanolates and ethanolates, acetonitrilates and the like. These compounds can also exist in polymorphic forms.

In any of the above embodiments, the compound or salt of formula (I) can have at least one asymmetric carbon atom. When the compound or salt has at least one asymmetric carbon atom, the compound or salt can exist in the racemic form, in the Rum of its pure optical isomers, or in the form of a mixture wherein one isomer is enriched relative to the other. In particular, in accordance with the present invention, when the inventive compounds have a single asymmetric carbon atom, the inventive compounds may exist as racemates, that is as mixtures of equal amounts of optical isomers, that is equal amounts of two enantiomers, or in the form of a single enantiomer. As used herein, "single enantiomer" is intended to include a compound that comprises more than 50% of a single enantiomer (that is enantiomeric excess up to 100% pure enantiomer).

When the compound or salt has more than one chiral center, the compound or salt can therefore exist as a mixture of diastereomers or in the form of a single diastereomer. As used herein, "single diastereomer" is intended to mean a compound that comprises more than 50% of a single diastereomer (that is diastereomeric excess to 100% pure diastereomer).

Synthetic Method

A general synthesis of embodiments of the compounds of the invention is depicted in Scheme 1. The synthesis of the compound 104 commences with reaction of alpha hydroxyketone 100 with a primary amine in the presence of catalytic zinc chloride to give the alpha aminoketone 101, which is not isolated but reacts directly with malononitrile to give aminopyrrole 102. Reaction of aminopyrrole 102 with triethyl orthoformate gives the imidate 103. Reaction of imidate 103 with primary amine $R^1NH_2$ in a solvent such as methanol provides final product 104.

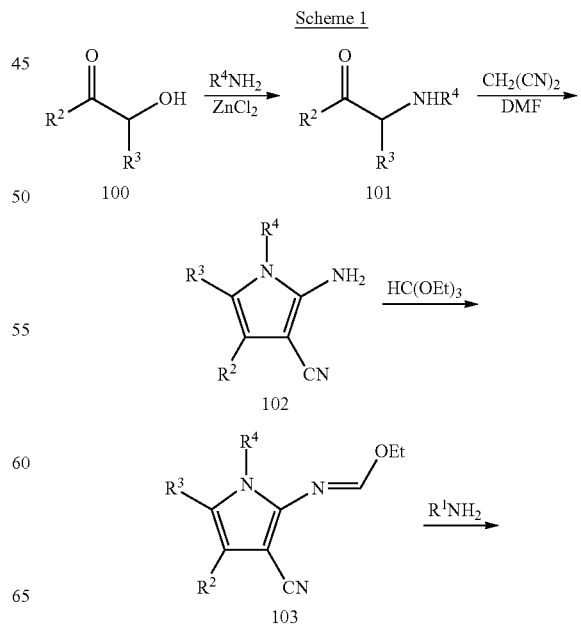

Scheme 1

-continued

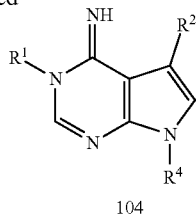

104

The present invention is further directed to a pharmaceutical composition comprising a pharmaceutically acceptable carrier and at least one compound or salt described herein.

It is preferred that the pharmaceutically acceptable carrier be one that is chemically inert to the active compounds and one that has no detrimental side effects or toxicity under the conditions of use.

The choice of carrier will be determined in part by the particular compound of the present invention chosen, as well as by the particular method used to administer the composition. Accordingly, there is a wide variety of suitable formulations of the pharmaceutical composition of the present invention. The following formulations for oral, aerosol, nasal, pulmonary, parenteral, subcutaneous, intravenous, intramuscular, intraperitoneal, intrathecal, intratumoral, topical, rectal, and vaginal administration are merely exemplary and are in no way limiting.

The pharmaceutical composition can be administered parenterally, such as intravenously, subcutaneously, intradermally, or intramuscularly. Thus, the invention provides compositions for parenteral administration that comprise a solution or suspension of the inventive compound or salt dissolved or suspended in an acceptable carrier suitable for parenteral administration, including aqueous and non-aqueous isotonic sterile injection solutions.

Overall, the requirements for effective pharmaceutical carriers for parenteral compositions are well known to those of ordinary skill in the art. See, such as Banker and Chalmers, eds., *Pharmaceutics and Pharmacy Practice*, J. B. Lippincott Company, Philadelphia, pp. 238-250 (1982), and Toissel, *ASHP Handbook on Injectable Drugs,* 4th ed., pp. 622-630 (1986). Such solutions can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound or salt of the present invention may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-beta-aminopropionates, and 2-alkyl-imidazoline quaternary ammonium salts, and (e) mixtures thereof.

The parenteral formulations can contain preservatives and buffers. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Topical formulations, including those that are useful for transdermal drug release, are well-known to those of skill in the art and are suitable in the context of the invention for application to skin. Topically applied compositions are generally in the form of liquids, creams, pastes, lotions and gels. Topical administration includes application to the oral mucosa, which includes the oral cavity, oral epithelium, palate, gingival, and the nasal mucosa. In some embodiments, the composition contains at least one active component and a suitable vehicle or carrier. It may also contain other components, such as an anti-irritant. The carrier can be a liquid, solid or semi-solid. In embodiments, the composition is an aqueous solution. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

Formulations suitable for oral administration can consist of (a) liquid solutions, such as a therapeutically effective amount of the inventive compound dissolved in diluents, such as water, saline, or orange juice, (b) capsules, sachets, tablets, lozenges, and troches, each containing a predetermined amount of the active ingredient, as solids or granules, (c) powders, (d) suspensions in an appropriate liquid, and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compound or salt of the present invention, alone or in combination with other suitable components, can be made into aerosol formulations to be administered via inhalation. The compounds are preferably supplied in finely divided form along with a surfactant and propellant. Typical percentages of active compound are 0.01%-20% by weight, preferably 1%-10%. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25%-5%. The balance of the composition is ordinarily propellant. A carrier can also be included as desired, such as lecithin for intranasal delivery. These aerosol formulations can be placed into acceptable pressurized propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

Additionally, the compound or salt of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

It will be appreciated by one of ordinary skill in the art that, in addition to the afore-described pharmaceutical compositions, the compound or salt of the present invention may be formulated as inclusion complexes, such as cyclodextrin inclusion complexes, or liposomes. Liposomes serve to target the compounds to a particular tissue, such as lymphoid tissue or cancerous hepatic cells. Liposomes can also be used to increase the half-life of the inventive compound. Liposomes useful in the present invention include emulsions, foams, micelles, insoluble monolayers, liquid crystals, phospholipid dispersions, lamellar layers and the like. In these preparations, the active agent to be delivered is incorporated as part of a liposome, alone or in conjunction with a suitable chemotherapeutic agent. Thus, liposomes filled with a desired inventive compound or salt thereof, can be directed to the site of a specific tissue type, hepatic cells, for example, where the liposomes then deliver the selected compositions. Liposomes for use in the invention are formed from standard vesicle-forming lipids, which generally include neutral and negatively charged phospholipids and a sterol, such as cholesterol. The selection of lipids is generally guided by consideration of, for example, liposome size and stability of the liposomes in the blood stream. A variety of methods are available for preparing liposomes, as described in, for example, Szoka et al., *Ann. Rev. Biophys. Bioeng.*, 9, 467 (1980), and U.S. Pat. Nos. 4,235,871, 4,501,728, 4,837,028, and 5,019,369. For targeting to the cells of a particular tissue type, a ligand to be incorporated into the liposome can include, for example, antibodies or fragments thereof specific for cell surface determinants of the targeted tissue type. A liposome suspension containing a compound or salt of the present invention may be administered intravenously, locally, topically, etc. in a dose that varies according to the mode of administration, the agent being delivered, and the stage of disease being treated.

To facilitate an understanding of the present disclosure, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having a disease" refers to a subject that presents one or more symptoms indicative of a disease (e.g., Alzheimer's disease (AD)). A subject suspected of having a disease may also have one or more risk factors. A subject suspected of having disease has generally not been tested for the disease. However, a "subject suspected of having disease" encompasses an individual who has received a preliminary diagnosis but for whom a confirmatory test has not been done or for whom the level or severity of metabolic disease is not known.

As used herein, the term "subject diagnosed with a disease" refers to a subject who has been tested and found to have a disease (e.g., AD). As used herein, the Willi "initial diagnosis" refers to a test result of initial disease that reveals the presence or absence of disease.

As used herein, the term "subject at risk for disease" refers to a subject with one or more risk factors for developing a specific disease (e.g., AD). Risk factors include, but are not limited to, gender, age, genetic predisposition, environmental exposure, and previous incidents of disease, pre-existing diseases, and lifestyle.

As used herein, the term "non-human animals" refers to all non-human animals including, but not limited to, vertebrates such as rodents, non-human primates, ovines, bovines, ruminants, lagomorphs, porcines, caprines, equines, canines, felines, ayes, etc.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., AD). Test compounds comprise both known and potential therapeutic compounds. A test compound can be determined to be therapeutic by screening using the screening methods of the present disclosure.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, and industrial samples. Such examples are not however to be construed as limiting the sample types applicable to the present disclosure.

As used herein, the term "effective amount" refers to the amount of a compound (e.g., a compound described herein) sufficient to effect beneficial or desired results. An effective amount can be administered in one or more administrations, applications or dosages and is not limited to or intended to be limited to a particular formulation or administration route.

As used herein, the term "co-administration" refers to the administration of at least two agent(s) (e.g., autophagy inhibitor compound having a structure presented above or elsewhere described herein) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent with a carrier, inert or active, making the composition especially suitable for diagnostic or therapeutic use in vivo, or ex vivo.

As used herein, the term "toxic" refers to any detrimental or harmful effects on a cell or tissue as compared to the same cell or tissue prior to the administration of the toxicant.

In an embodiment, condition is a decrease in levels or activity of cannabinoid receptor 1 (CB1R).

In certain embodiments, the decrease in the levels or activity of CB1R results from repeated administration of at least one CB1R receptor agonist to the mammal.

In an embodiment, the CB1R receptor agonist is a cannabinoid.

In certain embodiments, the use or method results in reduction of cannabinoid tolerance and enhancement of the analgesic effects of cannabinoids.

In an embodiment, the induction of autophagy results in sequestration of Beclin 2 from binding with GASP1.

The cannabinoid can be any suitable cannabinoid, many of which are known in the art. In a particular embodiment, the CBR1 receptor agonist is tetrahydrocannabinol.

The effects of cannabinoids are mediated by binding and activation of a G protein-coupled receptor (GPCR) cannabinoid receptor 1 (CB1R), and chronic exposure to cannabinoids results in lysosomal trafficking and degradation of CB1R, which causes diminished cellular responses and requires higher doses to produce the same effects. Therefore, retaining the functionality of CB1R may play an important role in the prevention of cannabinoid tolerance, especially in clinical applications. A recently identified autophagy gene, Beclin 2/Becn2, which belongs to the Beclin (coiled-coil, myosin-like BCL2-interacting protein) family, may link CB1R-regulated cell signaling and animal behavior to the autophagy pathway. Autophagy is an essential catabolic process that breaks down damaged or unnecessary structures in lysosomes, and the resulting metabolites are recycled and reused for new protein synthesis and energy production. Autophagy is intensely induced by physiological stimuli or stress, such as starvation9 and physical exercise, 10 and malfunction of autophagy has been implicated in a variety of diseases, including neurodegeneration, cardiovascular diseases, cancer and metabolic disorders. In addition to a role in autophagy, Beclin 2 is also essential for agonist-induced lysosomal degradation of a group of specific GPCRs, including CB1R, D2 dopamine receptor (D2R) and delta opioid receptor (DOR). In vitro biotin protection degradation data suggested that Beclin 2 mediates the degradation of these GPCRs by binding to GPCR-associated sorting protein 1 (GASP1), an adaptor protein that degrades GPCRs independently of ubiquitination and certain components of the canonical ESCRT (endosomal sorting complex required for transport) machinery.

It is unclear whether Beclin 2 regulates the downstream events of these GPCRs in response to chronic agonist exposure, including receptor re-sensitization, signaling cascades and drug-responsive behaviors in vivo, which are important questions especially when many of the GPCRs in this specific group are targets of psychoactive drugs, such as CB1R. In addition, the function, genetic basis and molecular mechanism of autophagy in the regulation of drug tolerance and dependence after repeated usage remain mysterious. It is also unknown how the autophagy pathway crosstalks with drug-responsive GPCR signaling and behavioral regulation, and whether Beclin 2 plays a role in the process.

Results

Figure 1:
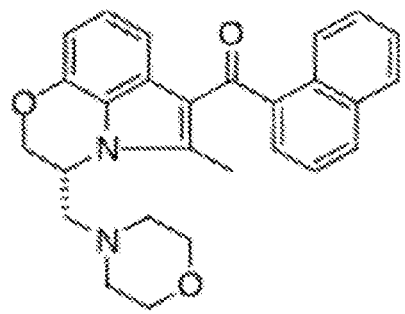
FIG. 1 shows the chemical structure of WIN55,212-2.

It was hypothesized that in response to prolonged cannabinoid exposure, Beclin 2 mediates the degradation and rapid deactivation of CB1R. To test this hypothesis, it was sought to use the Becn2+/− embryonic development period. Becn2+/− were treated or 14 d with WINSS,212-2 (WIN), a synthetic cannabinoid drug and CB1R agonist (FIG. 1), and analyzed the levels of CB1R in brain were. Compared to WT mice, Becn2+/− significantly higher level of brain CB1R after 14 d of chronic cannabinoid treatment (FIG. 2a), in addition to a trend of increased steady-state CB1R levels under normal conditions (with DMSO treatment), which suggests that Beclin 2 loss-of-function increases the availability of CB1R after repeated agonist dosage.

To study whether Beclin 2 functions in CB1R-regulated behavioral responsiveness following chronic cannabinoid treatment, the anti-nociceptive effect of WIN as a readout was analyzed by analgesic tolerance tests (FIG. 2B), using WT mice and mice heterozygous for Becn2 or Becn1, another Beclin family member that does not bind GASP1 or regulate GPCR degradation as control. There were no genotype differences either in basal pain sensitivity to infrared heat-generated pain (agonist-free, day 0) (FIG. 2C), or in analgesic effects of acute WIN treatment prior to chronic WIN administration (day 1) (FIG. 2D). However, 14 d of repeated WIN dosage markedly decreased its analgesic effect in WT and Becn2+/− mice (day 14) (FIG. 2D), suggesting that Becn2+/− induced by prolonged cannabinoid exposure. Notably, body weight of mice of all genotypes remained constant during chronic WIN treatment (FIG. 3). Thus, these data demonstrate that Beclin 2 downregulates the level of brain CB1R after prolonged WIN treatment, and Beclin 2 loss-of-function protects animals from developing analgesic tolerance to repeated exposure of cannabinoid drugs.

CB1R is Re-Sensitized at the Cell Surface upon Beclin 2 Loss

Next, the cellular mechanism underlying the behavioral protection against tolerance upon loss of Beclin 2 was investigated. Published data have shown that Beclin 2 is required for agonist-induced lysosomal transport of DOR, another GASP1-bound GPCR, which is relocalized to the plasma membrane upon loss of Beclin 2.8 However, it is unknown whether in the absence of Beclin 2 these recycled receptors are functional, or whether Beclin 2 also plays a role in the trafficking, recycling and signaling of CB1R after prolonged agonist exposure. Here it is proposed that Beclin 2 depletion stabilizes CB1R levels by promoting its recycling and resensitization at the cell surface, and tested this hypothesis from three aspects. The intracellular trafficking of CB1R in response to agonists was first followed, by examining its colocalization with endosome (EEA1) or lysosome (LAMP1) markers in the absence of Beclin 2.

By pulse-labeling cell-surface CB1R with antibody, it was found that compared to basal conditions (0 min), in a significantly higher number of cells treated with control siRNA, CB1R was transported to endosomes after 30 min of WIN treatment and to lysosomes after 60 min, whereas in cells transfected with Becn2 siRNA, instead of being transported to lysosomes for degradation, internalized CB1R was trapped in endosomal structures even after 60 min of WIN treatment (FIG. 4A, FIG. 5). In addition, in Becn2 siRNA-treated cells the endocytosed CB1R relocalized to the cell surface after 30 min of agonist removal and antagonist treatment (FIG. 4B).

Thus, these data demonstrate that loss of Beclin 2 leads to accumulation of CB1R in the endosomes and its eventual recycling to the plasma membrane.

Next, to study whether the recycled CB1R caused by Beclin 2 depletion is resensitized and functional, the signaling pathways downstream of CB1R at both biochemical and cellular levels were examined. CB1R is coupled to the Gi/o protein, and CB1R activation inhibits the adenylyl cyclase activity and cyclic AMP (cAMP) production, and activates the MAPK (mitogen-activated protein kinases) pathways, including MEK1/2 and JNK cascades. Thus, cannabinoid-induced cAMP suppression (FIG. 4C) and MAPK cascade phosphorylation were measured (FIG. 4D) in cell lines and primary MEFs following prolonged agonist treatment. It was found that the intracellular cAMP level was reduced in Becn2 siRNA-treated cells compared to control cells (FIG. 4C), which suggests an increased level of functional CB1R at the cell surface and is an indication of CB1R resensitization upon loss of Beclin 2. Furthermore, a higher level of cannabinoid-induced phosphorylation of MEK1/2 and JNK in Becn2 KO primary MEFs than in WT MEFs was detected (FIG. 4D), showing higher CB1R functionality after chronic agonist exposure in the absence of Beclin 2. Overall, these data show that loss of Beclin 2 leads to CB1R resensitization.

Identification of Novel Brain-Penetrable Autophagy Inducers

Accordingly, an important translational question is how to reduce Beclin 2 activity to maintain CB sensitivity and prevent drug tolerance induced by repeated cannabinoid exposure. To avoid the technical difficulty and risk of directly deleting Beclin 2 in vivo (such as injecting shRNAs or CRISPR/Cas9 constructs), which may disrupt Beclin 2-regulated autophagy, a novel and more convenient strategy to achieve the same goal via modulating the Beclin 2 interactome was developed and tested, which will not affect the essential autophagy function of Beclin 2 (FIG. 6A). Beclin 2 is present in two distinct protein complex pools, the Beclin 2-class III phosphatidylinositol 3-kinase complex for autophagy, and the Beclin 2-GASP1-GPCR complex in which Beclin 2-GASP1 binding is required for GPCR degradation. Thus, it was hypothesized that Beclin 2 is a limiting factor that regulates the balance between the two lysosomal degradation pathways, and that competitive recruitment of Beclin 2 to the autophagy machinery by activating autophagy prevents it from functioning in CB1R downregulation and thus restores CB1R functionality and reverses drug tolerance. To test this hypothesis, whether autophagy activation by brain-penetrable inducers inhibits the Beclin 2-GASP1 interaction was first examined. From a small-molecule library screen and a macro-molecule plant-chemical screen, two novel brain-penetrable autophagy-inducing compounds were identified: ML246 (also named metarrestin based on its anti-metastasis effects in cancer), a synthetic small molecule derived from a high-throughput screen against a pan-cancer cellular marker; and Rg2, a 785 Da natural steroid glycoside compound isolated from Panax ginseng by analytical chemistry approaches (FIG. 7). To determine autophagy activation by the two compounds, several markers of autophagy induction were analyzed, including formation of autophagosomes in cells and transgenic mice expressing GFP-tagged LC3 (an autophagosome marker), degradation of p62 (an autophagy substrate protein), and conversion of LC3 from the non-lipidated form (LC3-1) to the autophagosome-associated lipidated form (LC3-11). Both compounds markedly increased numbers of GFP-LC3 puncta (representing autophagosomes) and decreased levels of p62 in Hela cells and in mouse brain, as potent as starvation (FIGS. 6C-E, FIGS. 8A-C), although not detect significant changes in LC3-11 conversion in brain were not detected. In addition, when co-treated with the lysosomal inhibitor bafilomycin A 1, ML246 or Rg2 led to more accumulation of GFP-LC3 puncta, LC3-11 and p62 compared to normal conditions (FIGS. 6C and 6D, FIG. 8D), demonstrating an increased level of autophagic flux induced by either compound. Therefore, both agents are effective autophagy inducers in vitro and in vivo.

Activation of Autophagy Pharmacologically or Physiologically Attenuates Beclin 2-GASP1 Binding In Vitro and In Vivo Based on this model, the effect of these inducers on the Beclin 2-GASP1 interaction in vitro and in mouse brain were subsequently examined. It was found that autophagy induction either pharmacologically with ML246 or physiologically with starvation medium for 3 h potently blocked coimmunoprecipitation of endogenous GASP1 by Beclin 2 in HEK293 cells (FIG. 9A). Furthermore, injection of ML246 or Rg2 to WT mice, as well as 48-h starvation, dramatically decreased the binding between endogenous Beclin 2 and endogenous GASP1 in mouse brain (FIG. 9B). Thus, these data suggest that both physiological and novel pharmacological autophagy inducers attenuate Beclin 2-GASP1 binding, and serve as new candidate therapeutics in the prevention of receptor downregulation and cannabinoid tolerance to prolonged exposure.

Synthetic, Natural or Physiological Autophagy Inducers Prevent WT Mice from Analgesic Tolerance after Chronic Cannabinoid Usage Their therapeutic efficacy in WT mice were then tested. It was found that compared with vehicle injection, co-treatment of either ML246 or Rg2 with WIN potently rescued the pain-relieving effect of WIN in WT mice on day 14 to a day 1-like level (before repeated dosage) (FIG. 10A), demonstrating that the autophagy-inducing compounds prevent analgesic tolerance induced by chronic WIN administration. The co-treatment regime did not alter body weight of the mice (FIG. 11A). To confirm the findings with pharmacological inducers, it was further asked whether autophagy induction by physiological methods also rescues cannabinoid tolerance. Two methods that activate autophagy in mouse brain were adopted: the first is daily voluntary exercise by running wheel, which allows mice to run for approximately 1 km/night; and the second is a "2-day on/1-day off" periodic starvation protocol, in which mice were subject to cycles of 48-h fasting followed by 24-h feeding that allows them to return to normal weight in each cycle (FIG. 10B, FIG. 11B). At the end of chronic WIN treatment, similar to mice treated with autophagy-inducing compounds, mice undergoing daily running or intermittent fasting showed significantly higher sensitivity to the analgesic effects of WIN (FIG. 10C), suggesting that physiological autophagy inducers, such as exercise and starvation, prevent analgesic tolerance as well. Altogether, these data indicate that both pharmacological and physiological autophagy inducers prevent cannabinoid tolerance to repeated dosage.

Autophagy Induction Preserves Brain CB Level and Activity in Response to Chronic Cannabinoids To investigate whether restoration of CB1R signaling underlies the behavioral regulation by autophagy activation, the level and functionality of CB1R in mouse brain after co-administration of chronic cannabinoids and autophagy inducers were analyzed. Consistent with behavioral sensitization to WIN, after chronic WIN treatment higher levels of CB1R in the brain of mice concurrently treated with ML246 or Rg2 were detected (FIG. 12A), or fasted or exercised FIG. 12B), which were comparable to the brain CB level prior to chronic cannabinoid exposure (FIG. 1A). To determine whether the increased level of CB1R represents CB1R re-sensitization in the brain, the agonist-induced phosphorylation of signaling kinases downstream of CB1R after chronic WIN exposure were analyzed. It was found that repeated WIN treatment decreased activation of CB1R signaling induced by agonists (FIG. 12C), whereas autophagy induction either pharmacologically by ML246 or Rg2, or physiologically by starvation or exercise, rescued the CB1R signaling in spite of repeated WIN dosage, as demonstrated by increased phosphorylation of MEK and JNK (FIGS. 12D and 12E). Thus, these findings demonstrate that activating autophagy pharmacologically or physiologically effectively improves CB1R signaling after chronic cannabinoid exposure.

Discussion

These findings characterized an autophagy gene as a novel regulator of drug-responsive behaviors, and linked autophagy for the first time to CB1R sensitization and drug tolerance to cannabinoids, a substance that has emerged as a major medical and social challenge in recent decades. It was demonstrated that Beclin 2 is a new target in the prevention of tolerance to repeated cannabinoid dosage, and the concept of activating autophagy as an anti-tolerance therapeutic method was developed. Furthermore, novel autophagy-inducing compounds that achieve this goal by biochemically manipulating the Beclin 2-GASP1 protein complex were identified, which serve as candidate drug compounds to strengthen the pain-relieving effects of cannabinoids for chronic usage. Notably, it was also found that periodic starvation and daily exercise are effective to disrupt the Beclin 2-GASP1 interaction and to prevent mice from cannabinoid tolerance after repeated usage, although it cannot be ruled out that in these cases Beclin 2- or autophagy-independent mechanisms may also play a role in the anti-tolerance effects. To conclusively establish a causal relationship between Beclin 2-GASP1 binding and cannabinoid tolerance, it is useful to directly disrupt the Beclin 2-GASP1 interaction or specifically perturb the Beclin 2 function in autophagy in vivo.

Synthetic, Natural or Physiological Autophagy Inducers Prevent WT Mice from Analgesic Tolerance after Chronic Cannabinoid Usage The efficacy of ML246 and Rg2 in the maintenance of cannabinoid analgesia in WT mice was then tested. It was found that compared with vehicle injection, cotreatment of either ML246 or Rg2 with WIN potently rescued the pain-relieving effect of WIN in WT mice on day 14 to a day 1-like level (i.e., before repeated dosage) (FIG. 10A), suggesting that the autophagy-inducing compounds prevent analgesic tolerance induced by chronic WIN administration. The cotreatment regimen did not alter body weight of the mice. To confirm the findings with pharmacological inducers, it was further asked whether autophagy induction by physiological methods also rescues cannabinoid tolerance. Two methods were adopted that activate autophagy in mouse brain: the first is daily voluntary exercise by use of running wheels, which allows mice to run for approximately 1 km/night; and the second is a "2-day on/1-day off" periodic starvation protocol, in which mice were subjected to cycles of 48-h fasting followed by 24-h feeding that allowed them to return to normal weight in each cycle (FIG. 10B).

Although the increase in autophagosome formation was not significant in the brain (frontal cortex) of GFP-LC3 mice after a single bout of 48 h fasting as previously reported using fluorescence microscopy, a cumulative effect on autophagy induction was observed in the same brain region after multiple rounds of alternating fasting and feeding, demonstrated by a significant induction of GFP-LC3 puncta in the frontal cortex after 4 cycles of "2-day on/1-day off"

starvation. Although the exact mechanism of this additive effect is currently unclear, it is proposed that it may be due to a relatively stable glucose supply and low metabolism in the brain (compared to muscle and liver), leading to slow formation/turnover of autophagosomes that can be detected after repeated induction. This hypothesis is supported by the observation that skeletal muscle, which has high metabolic activity, does not show much cumulative effect with regard to autophagy induction by periodic starvation cycles. At the end of chronic WIN treatment, similar to mice treated with autophagy-inducing compounds, mice undergoing daily running or intermittent fasting showed significantly higher sensitivity to the analgesic effects of WIN (FIG. 10C), suggesting that physiological autophagy inducers, such as exercise and starvation, prevent analgesic tolerance as well. Altogether, these data show that both pharmacological and physiological autophagy inducers prevent cannabinoid tolerance to repeated dosage.

Autophagy Induction Preserves Brain CNR1 Level and Activity in Response to Chronic Cannabinoids To investigate whether restoration of CNR1 signaling underlies the behavioral regulation by autophagy activation, the level and functionality of CNR1 in mouse brain after co-administration of chronic cannabinoids and autophagy inducers was analyzed. Consistent with behavioral sensitization to WIN, after chronic WIN treatment we detected higher levels of CNR1 in the brain of mice concurrently treated with ML246 or Rg2 (FIG. 12A), or fasted or exercised (FIG. 12B), which were comparable to the brain CNR1 level prior to chronic cannabinoid exposure (FIG. 1A). To determine whether the increased level of CNR1 represents CNR1 resensitization in the brain, the agonist-induced phosphorylation of signaling kinases downstream of CNR1 after chronic WIN exposure was analyzed. It was found that repeated WIN treatment decreased activation of CNR1 signaling induced by agonists (FIG. 12C), whereas autophagy induction, either pharmacologically by ML246 or Rg2, or physiologically by starvation or exercise, rescued the CNR1 signaling in spite of repeated WIN dosage, demonstrated by increased phosphorylation of MAP2K and MAPK8/9 (FIGS. 12D-E). Thus, these findings show that activating autophagy pharmacologically or physiologically effectively improves CNR1 signaling after chronic cannabinoid exposure.

Cannabinoids can serve as promising therapeutics in many clinical occasions, such as alternative pain-relieving drugs for patients who develop tolerance to opioid medication. Yet cannabinoids' own potential of drug tolerance and dependence limits the medical use, which is sometimes a neglected issue due to the notion that cannabis may not cause as strong tolerance and dependence as some other drugs of abuse, such as opioids. Drug tolerance is likely to develop at different kinetics to various CB1R agonists of different efficacy; thus, it is investigated whether the pharmacological or physiological autophagy inducers mediate the same anti-tolerance responses to the natural cannabinoid THC (tetrahydrocannabinol) and other synthetic CB agonists in addition to WIN55,212-2. It is also useful to analyze the role of Beclin 2 and autophagy in the regulation of cannabinoid tolerance in disease models of inflammatory or neuropathic pain, as thermal pain generated in the analgesic tolerance tests may not exactly mimic these types of clinical pain. Thus, in some embodiments, surgical- or chemical-stimulation of inflammatory or neuropathic pain using the Becn2 KO mouse model is performed.

In certain embodiments, provided herein are compositions and methods for treating or preventing neurodegenerative disease. In particular, provided herein are compositions, methods, and uses of autophagy induction/activation mediated by compounds of the invention for treating and preventing neurodegenerative diseases, such as Alzheimer's disease and Huntington's disease.

In certain embodiments, the induction of autophagy results in reduction of amyloid β (Aβ) peptides.

In an embodiment, the Aβ peptides comprise Aβ42 peptide.

In certain embodiments, the induction of autophagy results in reduction of huntingtin.

In certain embodiments, the induction of autophagy prevents memory loss in neurodegeneration.

Autophagy is an evolutionarily conserved lysosomal catabolic pathway regulated by autophagy-related (ATG) proteins. Autophagy is induced by stress conditions such as hypoxia, starvation or oxidative stress; upon autophagy induction, autophagosomes sequester cytoplasmic components and fuse with lysosomes to generate autolysosomes, in which degradation of the autophagic cargos occurs. Although many studies have reported the roles of autophagy in the elimination of wasteful components, including protein aggregates, the relationship between autophagy and neurodegenerative disease progression, for example, Alzheimer's disease (AD) is complex. Several lines of evidence show an impairment of the autophagy pathway in the pathogenesis of AD. Brain from AD patients shows an abnormal accumulation of autophagic vacuoles and a reduction in the level of Beclin 1/BECN1, an essential autophagy protein and ortholog of ATG6.

However, direct evidence of autophagosome-mediated degradation of A or APP in brain is lacking. Paradoxically, autophagy has been reported to promote, rather than reduce, the production of A. Knockout (KO) of an essential autophagy gene Atg7 specifically in forebrain excitatory neurons of AD mice decreases extracellular amyloid plaque formation, which is due to reduced processing and secretion of Aβ; however, these Atg7 KO mice have exacerbated memory deficits indicating that the intracellular level of amyloids, which may be regulated by autophagy, may play a key role in cognitive impairment in AD. It is also under debate whether the level of the precursor protein APP is directly regulated by autophagy in either rodent brain or primary neurons. On the other hand, enhancing lysosomal degradation capacity by genetic deletion of Cystatin B, a suppressor of lysosomal cysteine proteases, or use of autophagy-inducing chemicals such as a phytochemical Rg2 or the mTOR inhibitor rapamycin, reduces amyloid burden and memory deficit in mouse models of AD. However, the mechanism of these compounds remains enigmatic. In addition, although knockout of autophagy genes leads to neurodegeneration, it is unknown whether physiologically increased basal autophagy prevents neurotoxicity of Aβ and has beneficial effects in protecting against Alzheimer's-like diseases.

Thus, to directly assess the function of physiological enhancement of autophagy in vivo, a unique mouse model of constitutively active autophagy caused by a single knockin mutation (F121A) in Becn 1 was generated and characterized. These autophagy-hyperactive mice were crossed with the 5XFAD transgenic AD mice, which overexpress a combination of 5 familial Alzheimer's disease (FAD) mutations in human APP and human PS I (presenihn 1) proteins and show early amyloid deposition beginning at 2 months of age and cognitive decline at 6 months of age. It was demonstrated that elevated basal autophagy targets Aβ oligomers, and significantly reduces the accumulation of Aβ, but not APP. Genetic hyperactivation of autophagy also ameliorates neuronal dysfunction and enhances survival in AD mice. In addition to genetic activation of autophagy, it was also found that autophagy hyperactivation either pharmacologically by a novel compound ML246 or physiologically by voluntary exercise protects AD mice from amyloid deposition and memory loss. Overall, this study provides the first evidence that hyperactive autophagy caused by a single mutation in Becn 1 sequesters amyloids and restores memory in AD, and also establishes the first genetic model of constitutively active autophagy as a useful in vivo tool to study autophagy in different diseases.

Accordingly, provided herein are compositions and methods for treating or preventing neurodegenerative disease by inducing autophagy with genetic, pharmaceutical, or lifestyle interventions.

Provided herein are methods of treating and preventing neurodegenerative disease through inducing autophagy (e.g., by inhibiting Becn1-Bcl-2 interactions). In some embodiments, the subject exhibits or does not exhibit symptoms of the disease. For example, in some embodiments, agents or interventions described herein are administered to a subject found to be at risk for a disorder (e.g., a subject exhibiting one or more markers or symptoms of, for example, AD but not meeting the diagnostic criteria for diagnosis of a disorder).

In some embodiments, the compounds and pharmaceutical compositions described herein are administered in combination with one or more additional agents, treatment, or interventions (e.g., agents, treatments, or interventions useful in the treatment of AD). Examples of agents useful in the treatment of PAH include, but are not limited to, donepezil (Aricept), galantamine (Razadyne), and rivastigmine (Exelon).

Some embodiments of the present invention provide methods for administering an effective amount of a compound of the invention and at least one additional therapeutic agent.

In some embodiments of the present invention, an intervention of the invention and one or more additional agents are administered to an animal under one or more of the following conditions: at different periodicities, at different durations, at different concentrations, by different administration routes, etc. In some embodiments, the intervention is administered prior to the additional agent, e.g., 0.5, 1, 2, 3, 4, 5, 10, 12, or 18 hours, 1, 2, 3, 4, 5, or 6 days, or 1, 2, 3, or 4 weeks prior to the administration of the additional agent. In some embodiments, the intervention is administered after the additional agent, e.g., 0.5, 1, 2, 3, 4, 5, 10, 12, or 18 hours, 1, 2, 3, 4, 5, or 6 days, or 1, 2, 3, or 4 weeks after the administration of the additional agent. In some embodiments, the intervention and the additional agent are administered concurrently but on different schedules, e.g., the intervention is administered daily while the additional agent is administered once a week, once every two weeks, once every three weeks, or once every four weeks. In other embodiments, the intervention is administered once a week while the additional agent is administered daily, once a week, once every two weeks, once every three weeks, or once every four weeks.

A knockin point mutation F121A in Becn1 leads to constitutively high autophagy in vivo.

To study how autophagy physiologically regulates the progression of Alzheimer's disease (AD), a new knock-in mouse model with hyperactive autophagy, by genetically disrupting the nutrient-regulated interaction between BECN1 and its inhibitor BCL2 (FIG. 13A) was generated. Reversible BECN1-BCL2 binding is an important regulatory mechanism of autophagy induction. When nutrients are abundant, BECN1 is bound and inhibited by BCL2, an anti-apoptotic and anti-autophagy protein. In response to stress such as starvation, BECN1 is released from the inhibitory binding of BCL2 for autophagy function.

The BCL2 binding site in human BECN1 is reported as FI23. It was found that F121 in the BH3 domain of mouse BECN1 is the corresponding conserved residue of human F123. Thus, it is proposed that mutating the residue F121 (TTT) to an alanine (A, GCT) disrupts BECN1-BCL2 binding and leads to constitutive activation of BECN1 and autophagy in mice (FIG. 13A). A global knock-in mouse line was then generated (BECN1$^{F4/F4}$), and it was found that the homozygous BECN1$^{F4/F4}$ mice are viable, fertile, of normal size and weight, and display normal histology in major organs under normal housing conditions (data not shown). The BECN1 protein expression level in BECN1$^{F4/F4}$ mice is also comparable to that in WT in multiple major organs, including brain, heart, skeletal muscle, liver and pancreas. Co-immunoprecipitation analysis showed that in BECN1$^{F4/F4}$ mice, there is much less interaction between BECN1 and BCL2 in both skeletal muscle and brain than in WT mice (FIG. 13B), indicating that the F121A mutation significantly weakens BCL2 binding to BECN1 in vivo.

To determine whether these mice have hyperactive autophagy, the mice were crossed with the GFP-LC3 autophagy reporter mice 12. Upon autophagy induction, diffusely distributed autophagosome marker protein LC3 (LC3-1) is conjugated to phosphatidylethanolamine to form lipidated LC3 (LC3-11), which specifically associates with autophagosomal membranes and can be resolved by western blot or visualized as fluorescent puncta. It was found that under non-autophagy-inducing conditions (fed and resting), Becn1$^{F4/F4}$ knock-in mice exhibited a higher number of GFP-LC3 puncta (autophagosomes) in both skeletal muscle (FIG. 14A) and brain (FIG. 14B) than wild-type (WT) mice, which reached similar levels under autophagy-inducing conditions (90-min treadmill exercise or 48-h starvation). These data indicate that Becn1$^{F4/F4}$ mice show high basal autophagy. To determine that the increment of autophagosomes in Becn1$^{F4/F4}$ mice is due to elevated autophagic flux, rather than a block in autophagosome degradation, the autophagy flux was analyzed by inhibiting lysosomal degradation using the lysosomal inhibitor chloroquine. In skeletal muscle of Becn1$^{F4/F4}$ mice, chloroquine injection led to more accumulation of LC3 and GFP-LC3 puncta compared to WT mice, measured by western blot analyses and microscopy, respectively (FIG. 14C). In addition, compared to WT mice, Becn1$^{F4/F4}$ mice showed a lower level of p62, an autophagy cargo protein, in skeletal muscle, which was rescued by chloroquine treatment (FIG. 14C). These data indicate that the Becn1$^{F121A}$ mutation in mice leads to higher autophagic degradation of LC3 and p62. Altogether, it is concluded that mutating F121 to A disrupts BECN1-BCL2 binding and constitutively activates autophagy in mice, thus providing a novel mouse model with hyperactive autophagy as a useful tool to analyze the physiological effects of autophagy upregulation in vivo.

Becn1$^{F121A}$ decreases amyloid accumulation and improves cognitive function in the 5XFAD Alzheimer's mouse model.

To determine the effects of autophagy activation on AD, the Becn1$^{F121A}$ mice were crossed with the 5XFAD mice, an amyloida mouse model used in AD research. 5XFAD mice demonstrate early and aggressive phenotypes of intraneuronal Aβ42 aggregates, β-amyloid plaques and neurodegeneration, and represent a good model for this study. Amyloid burden was first analyzed in the resulting 5XFAD Becn1$^{FA/FA}$ mice by dot blot assays, ELISA and microscopy at the age of 6 months (FIGS. 15A-D). The dot blot assay has been previously validated to measure levels of Aβ342 in APP transgenic mouse. It was found that 5XFAD Becn1$^{FA/FA}$ mice show lower levels of both soluble and insoluble Aβ42 in the brain than the 5XFAD mice by dot blot assays (FIGS. 15A-B), whereas expression of the precursor APP remained unaffected, indicating that Becn1FA/FA-mediated hyperactive autophagy downregulates the levels of Aβ42, but not of APP. This was also confirmed by ELISA analyses on the level of total brain Aβ342 (FIG. 15C). Furthermore, staining of amyloid plaques by Thioflavin S or Aβ42 antibody showed that there is a significant reduction of amyloid plaques in the cortex and a trend of reduction in the hippocampus of SXFAD Becn1$^{FA/FA}$ mice.

Importantly, Becn1$^{F121A}$-induced reduction in Aβ42 is dependent on autophagy but not other pathways that regulate amyloid transport. It was found that short-term (7-day) treatment of 5XFAD Becn1$^{F121A}$ mice with SBI-0206965, an autophagy inhibitor blocking the kinase activity of an essential upstream kinase ULK I 30, abolished the reduction in brain Aβ2 levels by dot blot assays (FIG. 15D). Similarly, in HEK293 cells stably expressing APP and Becn1$^{F121A}$, siRNA knockdown of the essential autophagy gene ATG7 significantly increased the level of intracellular Aβ42 by western blot analysis. The reduced Aβ42 level is not due to alterations in APP trafficking in Becn1$^{F121A}$ mice, as immunofluorescence microscopy showed no detectable difference in the amount of APP colocalized with RabS+ early endosomes or Rab7+ late endosomes in primary cortical neurons isolated from PDAPP Becn1$^{-/+}$ mice and PDAPP BeC1$^{FA/FA}$ mice. Furthermore, APP internalization and trafficking, by biotin protection assays using HEK293 cells expressing APP and WT Becn1 or Becn1$^{F121A}$ (the endogenous BECNI was deleted by CRISPR/Cas9) were also biochemically analyzed. After inducing endocytic trafficking of cell surface APP by incubating the cells at 37° C. for 5 min or 15 min, a similar level of APP endocytosis (represented by biotinylated APP that is protected from glutathione stripping) in cells expressing WT Becn1 and expressing Becn1$^{F121A}$ was observed. Thus, altogether, these results demonstrated that Becn1$^{F121A}$ does not affect APP trafficking. In addition, 5XFAD BeCn1$^{F121A}$ mice expressed a similar level of amyloid receptors in the brain that contribute to the clearance of Aβ, such as LDLR (Low-density lipoprotein receptor) and LRP I (LDLR-related protein 1), compared to 5XFAD mice expressing WT Becn1. Thus, altogether, it is concluded that the Becn1$^{F121A}$ knockin mutation reduces amyloid accumulation, and the effect of Becn1$^{F121A}$ on Aβ metabolism is mediated by the hyperactive autophagy activity.

Next, to analyze memory function, Morris water maze tests on WT mice and AD mice with normal or high autophagy were performed. During the visible platform training, all 3 groups of mice showed no significant difference in either escape latency or distance (FIG. 15C), indicating that there was no visual or swimming abnormality among all groups. In contrast, during the hidden platform trials, SXFAD mice expressing WT Becn1 showed apparent deficiency in memorizing the platform location, while 5XFAD Becn1$^{F121A}$ mice had significantly improved performance day by day in both escape latency and distance, similar to WT mice (FIG. 15E). These data indicate that the memory impairment caused by Aβ accumulation is ameliorated by the Becn1 F121A mutation. Overall, it is concluded that genetic stimulation of basal autophagy mediated by Becn1$^{F121A}$ reduces Aβ42 levels and plaque formation in mouse brain, and improves memory capacity that is impaired by amyloid aggregation in AD.

Becn1$^{F121A}$ increases survival of PDAPP AD mice.

To fully analyze the function of the Becn1$^{F121A}$ allele in AD, another amyloid mouse model, known as PDAPP mice, was used. These mice carry a V717F (Indiana) mutation in APP, and exhibit extracellular amyloid deposition starting at 6-9 months of age. The PDAPP mice have been shown to display an increased mortality rate compared to other AD lines. Similar to previous reports, it was found that PDAP mice have higher early mortality than WT mice starting at 2 months of age (FIG. 16). PDAPP mice were crossed with either the autophagy-hyperactive Becn1$^{F121A}$ mice, or autophagy-deficient Bcl2$^{AAA}$ mice. Bcl2$^{AAA}$ mice contain 3 knock-in alanine mutations (T69A, S70A and S84A) at the phosphorylation residues of BCL2, which block BCL2phosphorylation and BECN1 release from BCL2 binding; thus, they are opposite to the Becn1$^{F121A}$ mice and show defective autophagy H. Notably, homozygous expression of the Becn1$^{F121A}$ mutation decreased mortality in PDAPP mice, while the autophagy-deficient PDAPP Bcl2$^{AAA}$ mice showed a trend of exacerbated mortality compared to the PDAPP mice with normal autophagy (FIG. 16). These data indicate a positive impact of hyperactive autophagy mediated by Becn1$^{F121A}$ 1A on the survival of PDAPP Alzheimer's mice.

AP oligomers are sequestered inside autophagosomes.

To directly address whether intracellular amyloids are efficient autophagic cargos, and degraded by the autophagy machinery upon autophagy hyperactivation, a method to immunoisolate intact autophagosomes from the cortex of 5XFAD Becn1$^{FA/FA}$ mice expressing the autophagosome marker GFP-LC3 was developed. After sequential centrifugation and immunoprecipitation by anti-GFP antibody and magnetic beads, the purity of autophagosomes was validated by co-isolation of a known autophagy cargo p62 but not a cytosolic enzyme GAPDH (FIG. 17B). It was found that Aβ42 oligomers, including trimers, pentamers and higher-molecular weight fibrils or fibril intermediates (of size between 100 kD and 250 kD), but not monomers, are co-immunoprecipitated and concentrated with autophagosomes from autophagy-hyperactive mice (FIG. 17B). Thus, these data indicate biochemically that intracellular Aβ oligomers are cargos of autophagy, and are sequestered and cleared by hyperactive autophagy in brain.

Autophagy stimulation by ML246 and voluntary exercise reduces Aβ accumulation and improves cognitive function in 5XFAD mice.

In addition to Becn2$^{F121A}$-mediated genetic activation of autophagy, it was decided to further study whether stimulating autophagy pharmacologically is also protective against neurodegenerative progression. A brain-penetrable autophagy-inducing small molecule ML246 (metarrestin) was recently identified, and analyzed its effects on the clearance of aggregate-prone proteins in vitro and in vivo. For in vitro analyses, the HEK293 cell line stably expressing APP (APP-HEK293) was utilized, in which the produced Aβ molecules are efficiently secreted, to study the effect of ML246 on amyloid metabolism. Via dot blot assays, it was found that ML246 treatment for 24 h significantly reduced the level of secreted Aβ in the conditioned media (FIG. 18A). In addition, cultured WT primary cortical neurons treated with the conditioned media from ML246-treated APP-HEK293 cells underwent a lower level of apoptotic cell death than those treated with media from vehicle-treated APP-HEK293 cells (FIG. 18B). These results demonstrate that ML246 reduces amyloid production and secretion in vitro. Importantly, siRNA knockdown of the essential autophagy gene ATG7 in APP-HEK293 cells reversed the ML246-mediated reduction of both secreted Aβ42 (FIG. 18A) and apoptotic neuronal death (FIG. 18B), suggesting that the effect of ML246 in amyloid metabolism is autophagy-dependent.

ML246 promotes the removal of intracellular aggregates formed by polyglutamine (polyQ)-expansion proteins. HeLa cell lines stably expressing tetracycline-repressible expanded polyQ-repeat protein HTT (huntingtin) was used as a model, HTT65Q and HTT103Q. In contrast to the HTT protein with the normal number of glutamine repeats (HTT25Q), HTT65Q and HTT103Q formed insoluble polyQ aggregates larger than 0.2-μm diameter, which can be detected by filter trap assay. It was discovered that the accumulation of both HTT65Q and HTT103Q aggregates is decreased after ML246 treatment for 24 h, whereas knockdown of ATG7 prevents this reduction, suggesting that ML246 reduces intracellular protein aggregation, and this effect is dependent on the autophagy activity. Fluorescence imaging further confirmed that ML246 administration decreased the number of cells positive for HTT aggregates, which is also in an ATG7-dependent manner (FIG. S6B). Thus, these data indicate that the autophagy pathway stimulated by ML246 promotes the clearance of aggregate-prone proteins (including both amyloid and polyQ expansion proteins) in vitro, and ML246 can be used as a candidate compound for in vivo analyses in AD mouse models.

Accordingly, the function of ML246-induced autophagy in amyloid accumulation and cognitive function in 5XFAD mice was investigated. Via dot blot assays, it was found that compared to the ones treated with vehicle, 6-month old 5XFAD mice treated with ML246 for 5 weeks showed decreased levels of both soluble (FIG. 18C) and insoluble Aβ42 in brain (FIG. 18D). The expression of the precursor APP was not affected, supporting the hypothesis that the level of Aβ42, but not APP, is regulated by autophagy. Notably, the effect of ML246 was abolished in the autophagy-deficient 5XFAD Becn1+/− KO mice (FIGS. 18D-E), further supporting that ML246-induced reduction of Aβ42 in vivo is autophagy-dependent.

Moreover, in addition to pharmacological approaches, physical exercise has recently demonstrated as a fast and robust physiological method to induce autophagy in various tissues, including brain. Intriguingly, previous studies indicated that aerobic exercise decreases amyloid load in AD mouse models, and is also associated with a lower risk of cognitive decline among elderly populations. Thus, it was hypothesized that exercise-induced autophagy may represent a cellular mechanism underlying the neuroprotective effects of exercise in AD brain. To test this hypothesis, 2-month old 5XFAD mice were housed individually with access to a running wheel for 16 weeks. Through dot blot assays on brain lysates, it was found that 5XFAD mice subject to 16 weeks of voluntary running have significantly lower levels of both soluble (FIG. 19A) and insoluble (FIG. 19B) Aβ42 in brain than those housed under resting conditions (without running wheels), suggesting that physical exercise decreases the amyloid burden in AD mouse brain. Fluorescence microscopy also shows a significant reduction of amyloid plaques after exercise training, and a trend of plaque reduction after ML246 treatment, stained by thioflavin S or Aβ2 antibody in brain of 5XFAD mice, especially in the cerebral cortex (FIG. 19C). Similar to ML246 treatment, APP expression is not affected by exercise. In comparison, exercise failed to amyloid accumulation in the autophagy-deficient 5XFAD Becn1+/− KO mice (FIGS. 19A-B), suggesting that the autophagy pathway is required for the effects of exercise on amyloid accumulation.

Finally, to analyze whether the autophagy-inducing compound ML246 has the potential to improve the cognitive function of Alzheimer's mice, Morris water tests were performed on 6-month old 5XFAD mice injected with ML246 daily for 5 weeks. It was found that ML246 treatment, as well as 16-week voluntary exercise, improved the performance of 5XFAD mice during the hidden platform trials, compared to the vehicle-treated resting mice at the same age (FIG. 19C). These data suggest that similar to exercise, the autophagy inducer ML246 ameliorates memory impairment in AD mice.

Discussion

The role of autophagy in amyloid production and clearance has been unclear. In this study, a mouse model with hyperactive autophagy was generated by knocking-in a point F121A to Beclin11/Becn1, and it was found that Becn $1^{F121}$A-mediated autophagy hyperactivation reduces brain amyloid accumulation, ameliorates cognitive deficits, and improves survival rates in Alzheimer's mouse models.

BECN1 is a core component of the type III phosphatidylinositol-3-kinase (PI3K) complex, and is key for the initiation of autophagosome biogenesis. Lentiviral overexpression of Becn1 has been shown to reduce APP levels in cultured CHO cells or decrease amyloid deposition in AD mouse brain. Yet it is unclear whether Becn1 overexpression represents a physiological method for autophagy activation. Thus, a strategy was designed to constitutively activate autophagy in vivo by preventing BECN1 from binding with its inhibitor BCL2. Under nutrient rich conditions, BECN1 is bound and inhibited by BCL2; whereas in the presence of stress such as nutrient starvation and exercise, BCL2 is phosphorylated and released from BECN1, which activates autophagy and represents a physiological regulatory mechanism of the function of Becn1 in autophagy. In this new knock-in mouse model, the introduction of the F121A mutation in Becn1 (F121A) disrupts the BCL2 binding site, resulting in the constitutive activation of BECN1 in autophagy that is no longer regulated by stress. In skeletal muscle and brain of the Becn1$^{F121A}$ mice, the autophagy levels under basal conditions are as high as those obtained after physical exercise or starvation in WT mice. Thus, these mice were consequently crossed with amyloid mouse models, including 5XFAD and PDAPP mice, to study the function of Becn1-mediated autophagy in AD. Given the roles of autophagy in a broad spectrum of diseases, this new mouse model can be a useful genetic tool to study the physiological effects of autophagy hyperactivation in multiple diseases.

It was found that Becn1$^{F121A}$-mediated autophagy hyperactivation decreases Aβ levels and improves memory in 5XFAD mice. Besides the plasma membrane, APP also localizes to the secretory pathway (such as the trans-Golgi network and endoplasmic reticulum), endosomes, lysosomes and mitochondria. It is not known whether it is the intracellular Aβ, or the extracellular secreted pool taken back up by cells, that is regulated by autophagy in Becn1$^{FA/FA}$ mice. Several studies also suggest that BECN1 promotes internalization and lysosomal trafficking of the precursor protein APP. In cultured neuronal and HEK293 cell lines, BECN1 has been reported to promote endocytosis and endolysosomal and autolysosomal proteolysis of plasma membrane APP. The adaptor protein AP2 seems to interact with LC3 to target APP to autophagosome. However, whether APP trafficking and degradation depends on other key components in the autophagy machinery is not known, whether the process of autophagosome-mediated APP degradation occurs in AD mouse brain or neurons is still under debate Jts. These data argue against a role of autophagy in regulating the levels of APP, since it was found that Becn1$^{F121A}$ does not alter the level, internalization, or trafficking of APP in mouse brain, primary cortical neurons, or cell lines (FIG. S4, S5B-C), suggesting that the effect of Becn1$^{F121A}$ on amyloid metabolism is not the regulation of APP.

The role of autophagy in the regulation of Aβ is more complex. On one hand, Becn1 has been shown to be important for the phagocytosis and autophagic degradation of extracellular Aβ by cultured microglial cells, and Becn1-deficient mice showed impaired Aβ clearance 4, which is consistent with these findings. On the other hand, autophagy is suggested to facilitate Aβ processing and secretion from neurons, using neuroglioma cell lines and tissue-specific Atg7 KO mice in excitatory forebrain neurons. Thus, the autophagy-hyperactive AD mouse model is useful to assess the overall readout of autophagy activation on Aβ levels in vivo (FIG. 3-4). Using this model system, Aβ oligomers in purified intact autophagosomes were biochemically detected (FIG. 5), suggesting that autophagy a direct role in brain amyloid clearance. A model is proposed in which autophagic degradation of Aβ occurs in both neurons and glial cells, where neuronal autophagy mainly degrades de-novo processed Aβ, whereas autophagy in glia removes Aβ re-uptaken from the extracellular space (FIG. S7B).

Furthermore, besides hyperactivating autophagy by genetic factors, the effects of ML246, an autophagy-inducing compound that can pass the blood-brain barrier, on Aβ accumulation and cognition in AD mice were analyzed. Pharmacological strategies to autophagy have been recently proposed in the prevention of neurodegenerative diseases. Most autophagy inducers that have been tested are based on inhibiting the autophagy suppressor mTOR, such as the well-known mTOR inhibitor rapamycin which seems to be effective to decease Aβ levels and prevent cognitive impairment in AD mice when used at early stages prior to the formation of extracellular plaques. Here it has been shown that ML246 is able to decrease protein aggregation in cultured cells, and reduce Aβ levels and ameliorate memory deficit in 5XFAD mice, and notably, compound treatment was started at the age of 4-5 months when amyloid deposition has already been documented in this AD mouse model. Thus, ML246 is an autophagy activator of neuroprotective function and for use in AD treatment.

In addition to genetic and compound inducers of autophagy, it was also studied whether activating autophagy by physiological methods prevents AD. Starvation and exercise are the best-known physiological inducers of autophagy in vivo. Interestingly, although starvation induces detectable formation of autophagosomes in neurons of 3-month 5XFAD mice after 48 h, it seems ineffective in removing intra-neuronal or extracellular Aβ 55, likely due to insufficient degradation of Aβ-containing autolysosomes after short-term starvation. In comparison, exercise, either forced exercise by treadmill or voluntary exercise by miming wheel, has been recently shown to increase the autophagy flux in various tissues, including skeletal muscle and cerebral cortex in mice. Thus, the effects of physical exercise were investigated in AD, and demonstrated that 4 months of voluntary running exerted positive effects on animal behavior and amyloid pathology in brain of 5XFAD mice. It should be noted that voluntary exercise was started at the age of 2 months prior to any detectable cognitive impairment. Physical exercise has previously been indicated to play a role against cognitive decline in AD, but the molecular mechanism remains unknown. It has been shown for the first time that compared with AD mice with normal autophagy activity, exercise is not able to reduce amyloid deposition in brain of autophagy-deficient AD mice, indicating that exercise-induced autophagy may be an important mechanism mediating some of the beneficial effects of exercise on AD, although exercise may affect other pathways that also contribute to the exercise-mediated neuroprotective effects. Intriguingly, treadmill exercise does not appear to be as effective as voluntary wheel running to prevent neurodegeneration. It is likely that the stress associated with forced running on the treadmill exerts detrimental effects on animal behavior and disease pathogenesis. Finally, considering that one key problem in AD is the late diagnosis of the disease that significantly the effectiveness of subsequent treatments, voluntary exercise should be considered as an important component in modem lifestyle to effectively induce autophagy and prevent cognitive decline as a non-pharmacological intervention.

In summary, in this study 3 new strategies were developed to potently activate autophagy in the brain, genetic (by the Becn1$^{F121A}$ mutation), pharmacological (e.g., by ML246), and physiological (by voluntary exercise). Using the different approaches, evidence has been provided that autophagy induction ameliorates amyloid pathology and reduces cognitive deficits in 5XFAD mice. These data revealed the potential of autophagy stimulation in lowering toxic aggregate-prone proteins and improving neuronal functions for the treatment of AD.

In an embodiment, the compound is Rg2 of formula (II).

Rg2, a ginseng-derived steroid glycoside, induces autophagy in mouse tissues The autophagy-inducing and therapeutic potential of Rg2 was investigated in vivo. Panax ginseng has been used for thousands of years in East Asia as a traditional herbal medicine to treat diabetes and angiogenesis in cancer, and ginsenosides are proposed to be the major bioactive components. However, to date there has been a lack of clear experimental evidence characterizing the effectiveness and pharmacological mechanism of a variety of ginsenosides. Accordingly, it is hypothesized that the ginsenoside Rg2 may carry out some of the beneficial effects of Panax ginseng by activating autophagy.

To test this hypothesis, it was confirmed that Rg2 induces autophagy in vivo, by injecting Rg2 intraperitoneally (i.p.) into transgenic mice globally expressing GFP-LC3. It was found that Rg2 injection at the dose of both 10 mg/kg and 20 mg/kg significantly increases the number of GFP-LC3 puncta (autophagosomes) in multiple tissues, including brain frontal cortex, heart, liver and muscle (FIG. 2A). In addition, Rg2 treatment resulted in increased LC3-I to LC3-II conversion and decreased levels of SQSTM1 in liver, muscle, brain, heart, white adipose tissue and brown adipose tissue (FIG. 2B), supporting that Rg2 induces autophagy in vivo. Importantly, Rg2 treatment does not alter food intake in these mice, demonstrating that autophagy induced by Rg2 is not due to fasting. Furthermore, in vivo autophagy induction by Rg2 via GFP-LC3 puncta assays in both muscle and brain was examined. It was found that Rg2-induced autophagy peaks at 4 h and declines to the basal level after 8 to 16 h in muscle, whereas in the brain, autophagy activity peaks at 4 h and lasts for at least 24 h. Plasma protein binding assays demonstrated that when injected into mice, the percentage of Rg2 bound by plasma protein is approximately 42% at 10 μg/ml, 24% at 50 μg/ml, and 15% at 100 μg/ml (FIG. S6). Thus, the majority of Rg2 is not bound by plasma proteins and is freely available. Taken together, Rg2 was identified as a new in vivo autophagy inducer in vivo.

The accumulation of protein aggregates has been implicated in the pathogenesis of several neurodegenerative diseases. One approach by which these aggregates can be eliminated is through the activation of autophagy. In addition, it was found that Rg2 is able to enter the brain by the pharmacokinetics study. Its level peaks 15 min after injection, gradually decreases over 8 h postinjection, and is still detectable after 24 h postinjection. Thus, it is proposed that the ginsenoside Rg2 may mediate the protective effects against neurodegeneration by enhancing the autophagic clearance of aggregate-prone proteins.

Accordingly, whether Rg2 affects the clearance of proteinaceous inclusions in vitro was next determined, using HeLa cell lines expressing tetracycline-repressible expanded polyglutamine (polyQ)-repeat protein HTT (huntingtin), HTT65Q and HTT103Q. Unlike the HTT protein with the normal number of glutamine repeats (HTT25Q), HTT65Q and HTT103Q formed insoluble polyQ aggregates larger than 0.2-μm diameter, which were detected by filter trap assays (FIG. 5A). It was found that Rg2 treatment decreased accumulation of both HTT65Q and HTT103Q aggregates. The effect of Rg2 was abolished upon knockdown of the essential autophagy gene ATG7 (FIG. 5A), suggesting that Rg2-induced aggregate reduction is ATG7-dependent, and thus autophagy-dependent. This was also confirmed by immunofluorescence imaging analysis, which showed that the number of cells positive for HTT aggregates was reduced upon Rg2 administration (FIG. 5B). The Rg2-mediated reduction in HTT-positive cells was not due to reduced cell viability, as cells treated for 24 h (the same treatment time used to measure HTT aggregate clearance) grew as well as the control cells without mutant HTT expression (+Tet). Thus, these data suggest that autophagy induction by Rg2 enhances clearance of HTT aggregates in vitro.

To analyze whether Rg2 is protective in neurodegenerative disorders caused by aggregate-prone proteins, a mouse model of Alzheimer's disease was used, the 5XFAD mice, which overexpress a combination of 5 familial Alzheimer's disease (FAD) mutations in human APP (amyloid precursor protein) and human PS1 (presenilin 1) proteins. These mice demonstrate early and aggressive phenotypes of intraneuronal Aβ42 aggregates, β-amyloid plaques and neurodegeneration, and represent a good model for our study. Using dot blot assays of the brain lysates, it was found that compared with vehicle (DMSO) treatment, Rg2 injection for 16 weeks in 2 month-old male 5XFAD mice effectively decreased the level of brain Aβ42 (FIG. 6A), the aggregate-prone peptide cleaved from APP, whereas expression of the precursor APP remained unaffected (FIG. S10B). Microscopy data further showed that in Rg2-treated 5XFAD mice, there was a significantly fewer number of amyloid plaques, stained by either thioflavin or Aβ42 antibody (FIG. 6B). Collectively, these data demonstrated that Rg2 reduces intracellular Aβ42 levels and extracellular plaque formation in mouse brain.

Rg2 improves cognitive function in a mouse model of Alzheimer's disease

To determine the effects of Rg2 treatment in vivo, we performed several behavioral assays in the 5XFAD mouse model were performed. For cognitive function, Morris water maze tests were performed. In water maze tests with a visible platform there was no significant difference in either escape latency or distance among WT, vehicle (DMSO)-treated mice or Rg2-treated mice (FIG. 6C), suggesting there was no visual abnormality among all groups. In contrast, in tests with a hidden platform, vehicle-treated 5XFAD mice showed apparent deficiency in learning and memory of the platform location over the time of 5 d, whereas Rg2-treated mice had significantly improved performance in both escape latency and distance similar to WT mice (FIG. 6C). These data suggest that the learning and memory impairment caused by amyloid accumulation is ameliorated by Rg2 treatment. It should be noted that no rescue in the locomotor activity of Rg2-treated 5XFAD mice compared to vehicle-treated ones was observed, as assayed quantitatively by the distance travelled in the open-field tests, suggesting that the shortened escape latency and distance in the hidden platform test is not due to overall improvement in physical ability. In addition, in 5XFAD mice with or without Rg2 injection, contextual fear memory was tested, which is mediated by hippocampal function and impaired by amyloid deposition. It was found that treatment of Rg2 rescued the freezing responses of 5XFAD mice when they were placed in the same context of the foot-shock conditioning chamber (FIG. 6D), suggesting an improvement of the hippocampal-dependent contextual fear memory in these mice. Overall, Rg2 treatment improves mouse learning and memory function that is impaired by Aβ aggregation.

The invention includes the following embodiments:

1. A compound of formula (I):

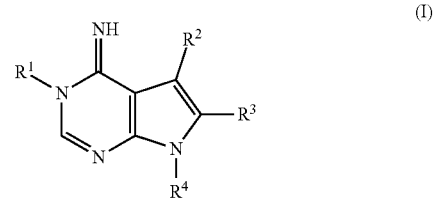

wherein $R^1$ is selected from the group consisting of alkyl, hydroxyalkyl, dialkoxyalkyl, trialkylsiloxyalkyl, thioalkyl, alkoxyalkyl, alkylthioalkyl, cycloalkyl, hydroxycycloalkyl, hydroxycycloalkylalkyl, thiocycloalkyl, alkoxycycloalkyl, alkylthiocycloalkyl, dialkylaminoalkyl, heterocyclyl, heterocyclylalkyl, heteroaryl, arylalkyl, arylalkylpiperidin-4-yl, arylpiperazinylalkyl, and heteroarylalkyl, $R^2$ is aryl or heteroaryl, $R^3$ is selected from the group consisting of H, alkyl, cycloalkyl, aryl, heteroaryl, arylalkyl, and heteroarylalkyl, $R^4$ is selected from the group consisting of alkyl, cycloalkyl, cycloalkylalkyl, aryl, heteroaryl, arylalkyl, and heteroarylalkyl, or a pharmaceutically acceptable salt thereof, wherein $R^1$, $R^2$, $R^3$, and $R^4$, other than H, are optionally substituted on the aryl and/or alkyl portion with one or more substituents selected from the group consisting of halo, alkyl, hydroxyalkyl, thioalkyl, alkoxy, alkylthioalkyl, alkoxycarbonyl, alkylthiocarbonyl, amino, alkylamino, dialkylamino, aminosulfonyl, hydroxyl, perfluoroalkoxy, alkylenedioxy, and alkylcarbonyl, ginsenoside Rg2 of structure (II):

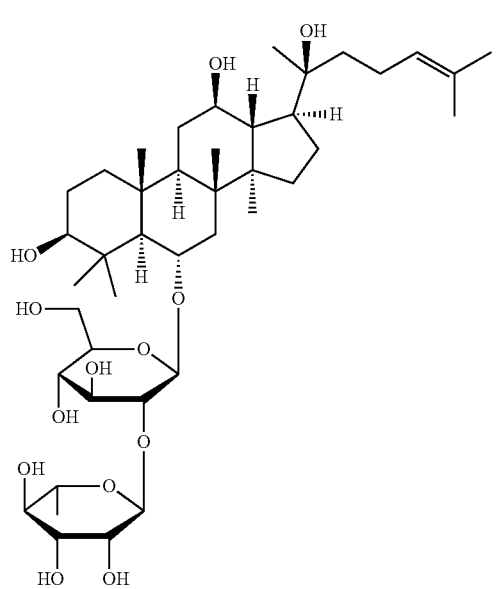

(II)

ginsenosides Re, Rf, or Rg1 of formula (III):

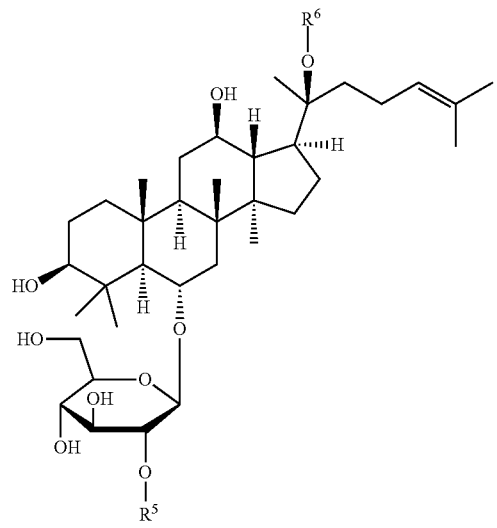

(III)

wherein $R^5$ is α-L-rhamnopyranosyl and $R^6$ is β-D-glucopyranosyl (ginsenoside Re), $R^5$ is β-D-glucopyranosyl and $R^6$ is H (ginsenoside Rf), or $R^5$ is H and $R^6$ is β-D-glucopyranosyl (ginsenoside Rg1), ginsenosides Rb1, Rb2, or Rc of formula (IV):

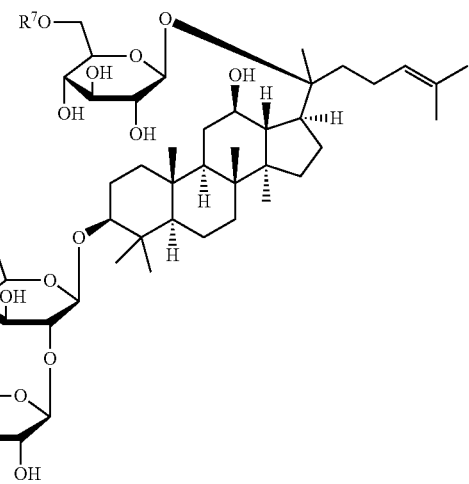

(IV)

wherein $R^7$ is β-D-glucopyranosyl (ginsenoside Rb1), α-L-arabinopyranosyl (ginsenoside Rb2), or α-L-arabinofuranosyl (ginsenoside Rc), a compound of formula (V):

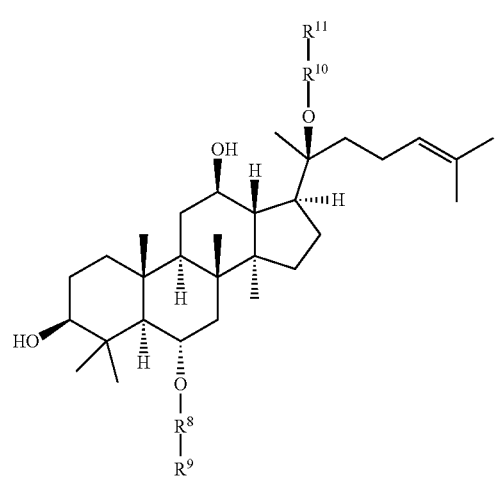

(V)

wherein $R^8$-$R^{11}$ are independently selected from the group consisting of β-D-glucopyranosyl, α-L-arabinopyranosyl, α-L-rhamnopyranosyl, and α-L-arabinofuranosyl, a compound of formula (VI):

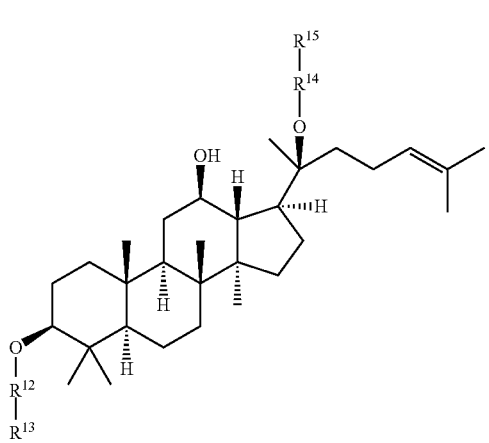

wherein $R^{12}$-$R^{15}$ are independently selected from the group consisting of β-D-glucopyranosyl, α-L-arabinopyranosyl, α-L-rhamnopyranosyl, and α-L-arabinofuranosyl, a compound of formula (VII):

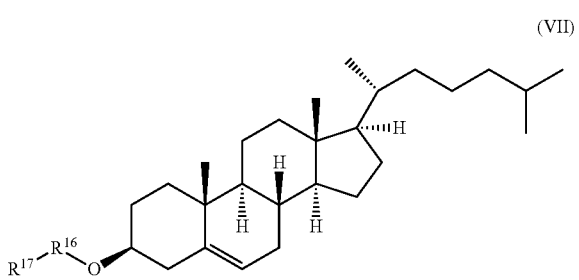

wherein $R^{16}$ and $R^{17}$ are independently selected from the group consisting of β-D-glucopyranosyl, α-L-arabinopyranosyl, α-L-rhamnopyranosyl, and α-L-arabinofuranosyl, a compound of formula (VIII):

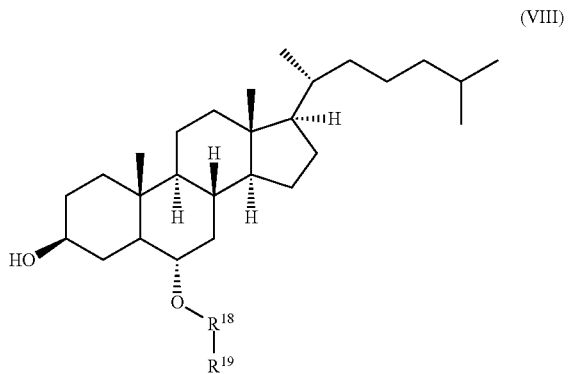

wherein $R^{18}$ and $R^{19}$ are independently selected from the group consisting of β-D-glucopyranosyl, α-L-arabinopyranosyl, α-L-rhamnopyranosyl, and α-L-arabinofuranosyl, a compound of formula (IX):

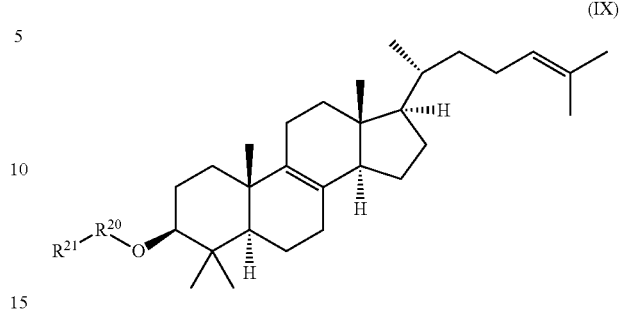

wherein $R^{20}$ and $R^{21}$ are independently selected from the group consisting of β-D-glucopyranosyl, α-L-arabinopyranosyl, α-L-rhamnopyranosyl, and α-L-arabinofuranosyl, or a compound of formula (X):

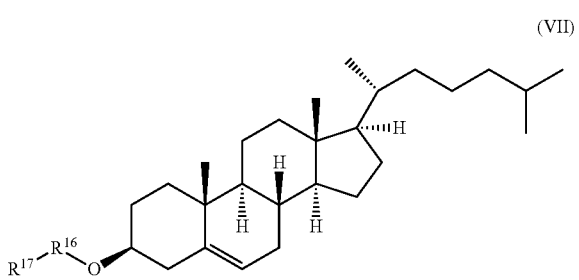

wherein $R^{22}$ and $R^{23}$ are independently selected from the group consisting of β-D-glucopyranosyl, α-L-arabinopyranosyl, α-L-rhamnopyranosyl, and α-L-arabinofuranosyl, or any combination thereof, for use in of treating or preventing a condition responsive to the induction of autophagy in a brain of a mammal in need thereof.

2. The compound or salt for use according to embodiment 1, wherein the compound is of formula (I) and $R^2$ is phenyl, optionally substituted with one or more substituents selected from the group consisting of halo, alkyl, hydroxyalkyl, thioalkyl, alkoxy, alkylthioalkyl, alkoxycarbonyl, alkylthiocarbonyl, amino, alkylamino, dialkylamino, and alkylcarbonyl.

3. The compound or salt for use according to embodiment 1 or 2, wherein $R^3$ is phenyl, optionally substituted with one or more substituents selected from the group consisting of halo, alkyl, hydroxyalkyl, thioalkyl, alkoxy, alkylthioalkyl, alkoxycarbonyl, alkylthiocarbonyl, amino, alkylamino, dialkylamino, and alkylcarbonyl.

4. The compound or salt for use according to any one of embodiments 1-3, wherein $R^4$ is benzyl, wherein the phenyl ring is optionally substituted with one or more substituents selected from the group consisting of alkyl, hydroxyalkyl, thioalkyl, alkoxy, alkylthioalkyl, alkoxycarbonyl, alkylthiocarbonyl, amino, alkylamino, dialkylamino, aminosulfonyl, hydroxyl, perfluoroalkoxy, and alkylcarbonyl.

5. The compound or salt for use according to any one of embodiments 1-4, wherein $R^1$ is a 5 or 6-membered heterocyclyl group having at least one hetero atom selected from the group consisting of O, N, and S; a hydroxy $C_1$-$C_7$ cycloalkyl group; a hydroxy $C_1$-$C_6$ alkyl group; a N,N-di($C_1$-$C_6$ alkyl)amino $C_1$-$C_6$ alkyl group; a $C_1$-$C_6$ alkoxy $C_1$-$C_6$ alkyl group; a heteroaryl $C_1$-$C_6$ alkyl group; a heterocyclyl $C_1$-$C_6$ alkyl group; phenyl $C_1$-$C_6$ alkyl group where the phenyl ring is substituted with one or more $C_1$-$C_6$ alkoxy groups; N-benzyl piperazinyl; N-phenyl piperazinyl-alkyl; a phenyl $C_1$-$C_6$ alkyl group where the alkyl is substituted with a hydroxy group; or a 5 or 6 membered heteroarylamino $C_1$-$C_6$ alkyl group wherein the heteroaryl group has at least one hetero atom selected from the group consisting of O, N, and S.

6. The compound or salt of any one for use according to embodiments 1-5, wherein $R^1$ is selected from the group consisting of the following:

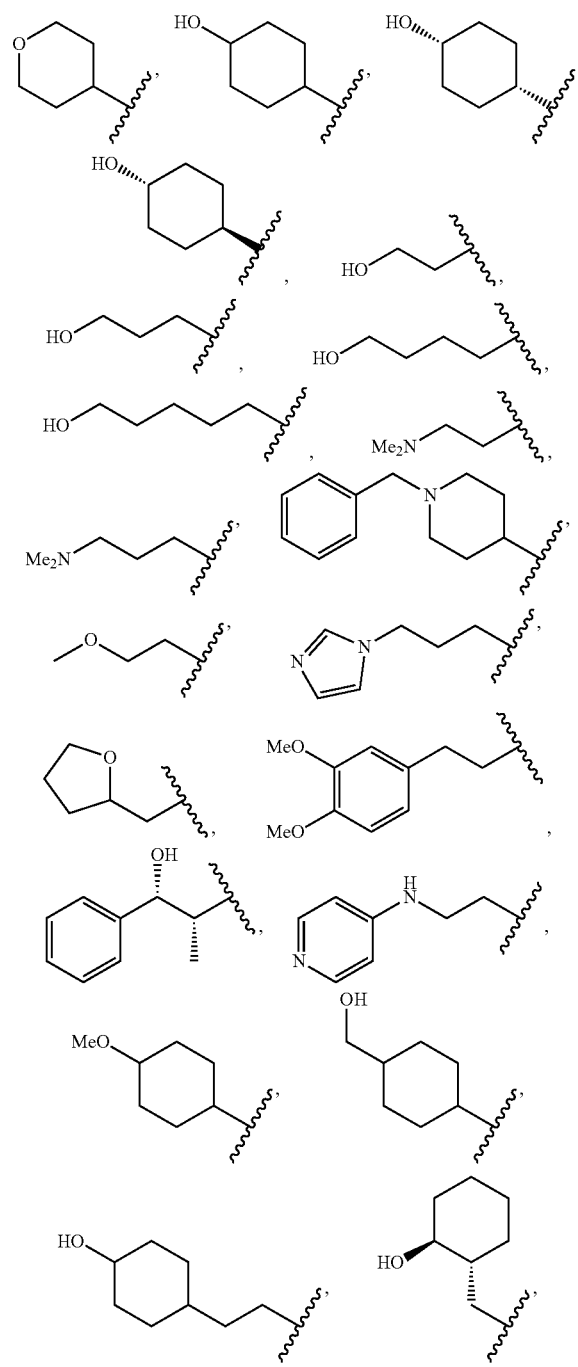

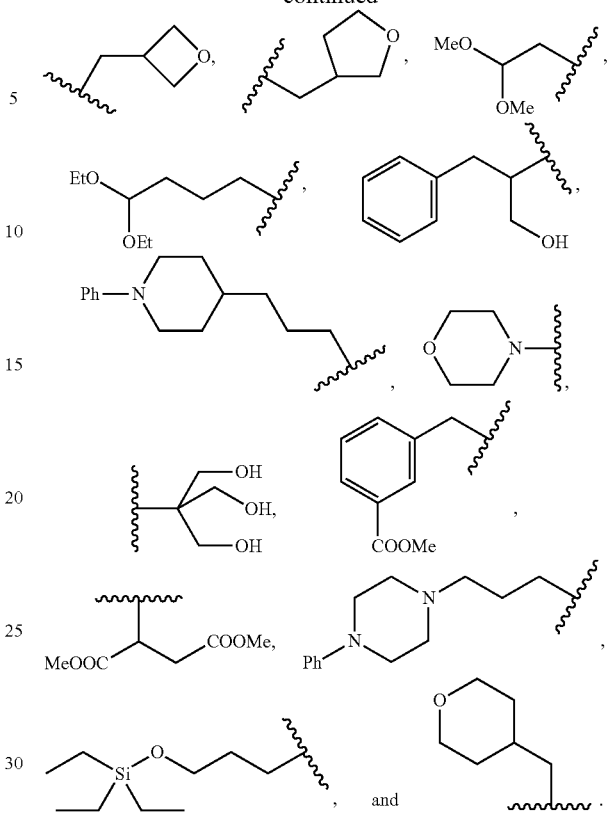

7. The compound or salt for use according to any one of embodiments 1-6, wherein $R^2$ is phenyl, $R^3$ is phenyl, $R^4$ is benzyl, and $R^1$ is selected from the group consisting of the following:

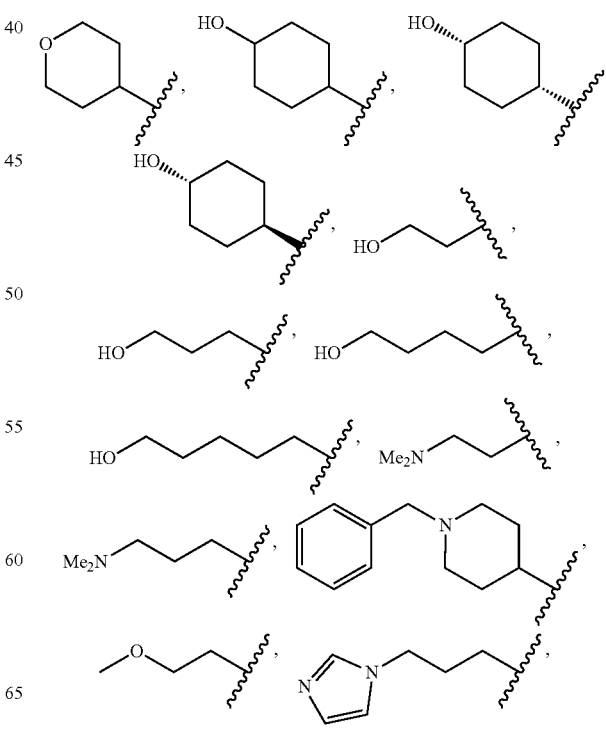

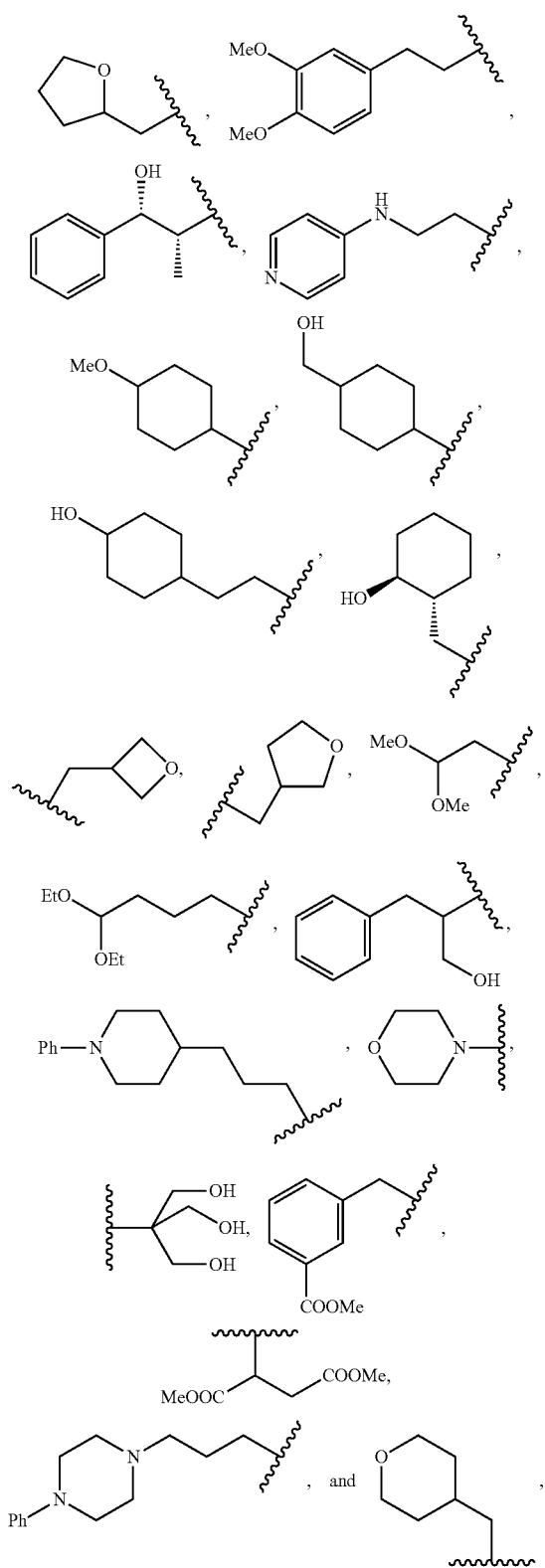

8. The compound or salt for use according to embodiment 1, wherein $R^4$ is 4-methoxybenzyl, $R^2$ is phenyl, $R^3$ is phenyl, and $R^1$ is selected from the group consisting of the following:

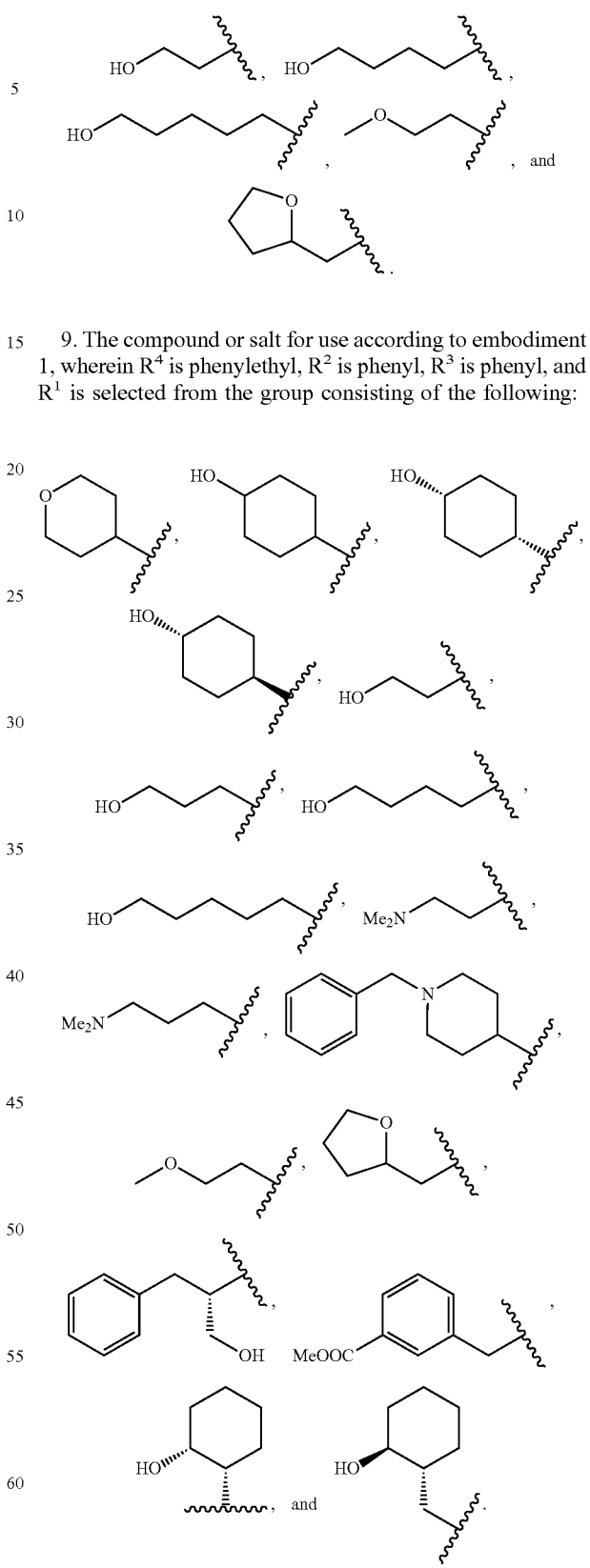

9. The compound or salt for use according to embodiment 1, wherein $R^4$ is phenylethyl, $R^2$ is phenyl, $R^3$ is phenyl, and $R^1$ is selected from the group consisting of the following:

10. The compound or salt for use according to embodiment 1, wherein $R^2$ is phenyl, $R^3$ is phenyl, $R^4$ is

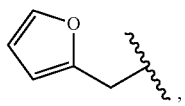

and R¹ is selected from the group consisting of the following:

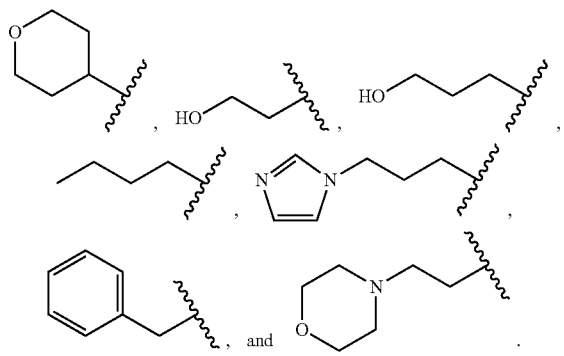

11. The compound or salt for use according to embodiment 1, wherein R⁴ is selected from 4-aminosulfonylbenzyl, 4-trifluoromethoxybenzyl, 4-methoxybenzyl, and cyclopropylmethyl, and wherein R¹ is selected from the following:

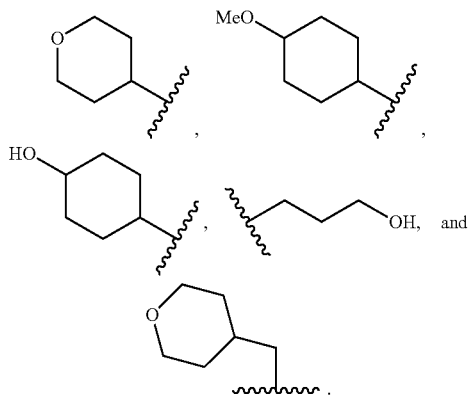

12. The compound or salt for use according to embodiment 1, wherein the compound is of formula (II).

13. The compound or salt for use according to any one of embodiments 1-12, wherein the condition is a decrease in levels or activity of cannabinoid receptor 1 (CB1R).

14. The compound or salt for use according to embodiment 13, wherein the decrease in the levels or activity of CB1R results from repeated administration of at least one CB1R receptor agonist to the mammal.

15. The compound or salt for use according to embodiment 14, wherein the CB1R receptor agonist is a cannabinoid.

16. The compound or salt for use according to any one of embodiments 13-15, wherein the method results in reduction of cannabinoid tolerance and enhancement of the analgesic effects of cannabinoids.

17. The compound or salt for use according to any one of embodiments 13-16, wherein the induction of autophagy results in sequestration of Beclin 2 from binding with GASP1.

18. The compound or salt for use according to any one of embodiments 13-17, wherein the CBR1 receptor agonist is tetrahydrocannabinol.

19. The compound or salt for use according to any one of embodiments 1-12, wherein the condition is a neurodegenerative disease.

20. The compound or salt for use according to embodiments 19, wherein the neurodegenerative disease is Alzheimer's disease or Huntington's disease.

21. The compound or salt for use according to embodiments 19 or 20, wherein the induction of autophagy results in reduction of amyloid β (Aβ) peptides.

22. The compound or salt for use according to embodiments 21, wherein the Aβ peptides comprise Aβ342 peptide.

23. The compound or salt for use according to embodiments 19, wherein the induction of autophagy results in reduction of huntingtin.

24. The compound or salt for use according to embodiments 19, wherein the induction of autophagy prevents memory loss in neurodegeneration.

The following examples further illustrate the invention but, of course, should not be construed as in any way limiting its scope.

Materials and Methods

Mice. All animal experiments have been approved by the Northwestern University Institutional Animal Care and Use Committee (IACUC) (Protocol number: IS00004749). All mice were housed on a 12-h light/dark cycle, and male mice were used for behavioral analyses. All mice were in the C57BL/6 background except PDAPP mice. The PDAPP mice were generated in a C57BL/6 and DBA2 mixed genetic background and have been backcrossed with C57BL/6 mice for 8 generations prior to analyses. GFP-LC3 transgenic, Becn1$^{+/-}$ KO, Bcl2$^{AAA}$, PDAPP and 5XFAD mice have been previously described.

For the construction of a mouse strain with the F 121A knock-in allele in Becn1, BAC clones (Incyte) were screened for the presence of Becn1. The Becn1 BAC clone was subcloned into the pVB vector and the F121 (TTT) in exon 6 of Becn1 was replaced by A (GCT). A neomycin resistance marker flanked by LoxP sites was inserted between exons 7 and 8. The resulting targeting construct, pVBKI-Becn1, was linearized by I-CeuI digestion and into 129 Sv/JxC57BL/6J hybrid ES cells, and 36 h later, clones were selected with neomycin, and screened by Southern blot analysis with the probes indicated in FIG. S1. DNA was digested with HindIII, and electrophoretically separated on a 0.8% agarose gel. After transfer to a nylon membrane, the digested DNA was hybridized with a probe targeted against the 5' region (Probe 1).

The positive clones were further confirmed by Southern blot analyses using a 3' probe. DNA was digested with HindIII, and electrophoretically separated on a 0.8% agarose gel. After transfer to a nylon membrane, the digested DNA was hybridized with a probe targeted against the 3' region (Probe 2).

The positive knock-in clones were tested for normal karyotype and used to inject blastocysts from C57BL/6J donors. Mice with germline transmission were bred to mice expressing Cre the CAG promoter (gift of Eric Olson, UT Southwestern Medical Center) to remove the neomycin cassette. Offspring were genotyped for the presence of the knock-in allele by PCR with the following primers: 5' primer; knock-in 3' primer; wild-type 3' primer. Using this scheme, the knock-in Becn1$^{F121A}$ allele was identified by a PCR product of 650 bp, and the wild-type allele was identified by a PCR fragment of 320 bp. Becn1$^{F121A}$ mice were backcrossed for more than 10 generations to C57BL/6J mice (Jackson Laboratories).

For the generation of 5XFAD; Becn 1FA/FA mice, heterozygous 5XFAD transgenic mice were bred to homozygous Becn1 knock-in (Becn 1FA/FA) mice to obtain SXFAD; Becn1$^{FA/+}$ mice, which were bred to the Becn1$^{FA/FA}$ or Becn1$^{-/+}$ littermate mice to produce the 5XFAD; Becn1$^{FA/FA}$ and 5XFAD; Becn1$^{-/+}$ offspring. For the generation of PDAPP; Becn1$^{FA/FA}$ mice, heterozygous PDAPP transgenic mice were bred to homozygous Becn1 knock-in (Becn1$^{FA/FA}$) mice, and the offspring were bred to the Becn1$^{FA/FA}$ or Becn1$^{+/+}$ littermate mice to produce the PDAPP; Becn1$^{FA/FA}$ and PDAPP; Becn1$^{+/+}$ mice. Similarly, PDAPP transgenic mice were crossed with homozygous Bcl2$^{AAA}$ mice to produce the PDAPP; Bcl2$^{AAA}$ mice.

Cell lines. HeLa cell lines were obtained from ATCC, and HeLa cells conditionally expressing CFP-tagged Huntingtin with polyQ repeats were from A Yamamoto (Columbia University). The HEK293 cell line stably expressing APP (APP-HEK293 cells) was generated by recombinant adenovirus encoding WT human APP under the control of the CMV promoter. Cells were cultured in DMEM medium (Gibco, 11995073) supplemented with 10% FBS. Tetracycline-free FBS was used for HeLa cells stably expressing Huntingtin Takara Bio USA, 631 107), and regular FBS was used for all other cells (HyClone, SH30070.03HI).

Isolation and culture of primary cortical neurons. Cortical neurons were isolated from e16.5 mouse embryos via dissociation in 0.25% trypsin at 37° C. Neurons from each single were separately plated at the density of 105 cells per well on culture slides (4 well-culture slide) coated with 100 µg/ml poly-L-lysine in borate buffer (50 mM boric acid, 12.5 mM borax). Neurons were plated in neurobasal media (Gibco 21103-049) supplemented with 2% B-27 (Gibco 17504-044), 500 µM glutamine (Invitrogen), 10% horse serum and 2.5 µM glutamate. After 2 h, media was replaced with growth media (neurobasal media with 2% B-and 500 µM glutamine).

Co-immunoprecipitation from muscle and brain tissue. Mouse tissues (muscle and brain) were homogenized in lysis buffer containing 50 mM Tris (pH 7.5), 150 mM NaCl, 1 mM EDTA, 1% Triton X-100, halt proteinase inhibitor cocktail (TheimoFisher Scientific), and phosphatase inhibitor cocktail (ThermoFisher Scientific), and subjected to immunoprecipitation with anti-BCL2 monoclonal antibody conjugated agarose beads (Santa Cruz Biotechnology 7382 AC). Eluates were separated by SDS-PAGE and detected by anti-BCL2-HRP antibody (C2 Santa Cruz Biotechnology, 1:500) and anti-BECN1 antibody (Santa Cruz Biotechnology, 1:200) using the ONE-HOUR Western Detection Kit (GenScript) following the manufacturer's instruction.

Autophagosome immunoisolation. Cortex samples from 12-week old 5XFAD; Been 1FNF,\GFP-LC3 mice were dissected and homogenized in 1 ml cold lysis buffer pH 7.4 containing 250 mM sucrose, 1 mM EDTA, 10 mM HEPES, halt proteinase inhibitor cocktail (ThermoFisher Scientific), and halt phosphatase inhibitor cocktail (ThermoFisher Scientific), using a Dounce tissue grinder (Wheaton). The lysate was then passed 15 times through 27-gauge needle. GFP-based immunoisolation was performed using Dynabeads Protein G (ThermoFisher Scientific). The lysate was centrifuged at 1,000×g for 10 min at 4° C. The post-nuclear supernatant fraction was centrifuged at 20,000×g for 20 min and the supernatant fraction was discarded to remove residual cytosolic GFP-LC3. The pellet fraction was resuspended in 250 µl lysis buffer and was incubated for 2 hours at 4° C. with 40 µl of Dynabeads, preincubated O/N with GFP-antibody (Sigma, G1 544). The beads were then washed 4 times with wash buffer (150 mM NaCl, 250 mM sucrose, 1 mM EDTA, 10 mM HEPES) using the magnetic Separator DynaMag1M-2 (ThermoFisher Scientific). Immunoprecipitates were eluted with lysis buffer containing IX sample buffer and analyzed by SDS-PAGE.

Drug treatment. For in vivo use, ML246 was dissolved in a solvent containing 5% of NMP, 20% of PEG400 and 75% of 10% HP-CD in water, and injected intraperitoneally at the dosage of 5 mg/kg body weight for 5 weeks, 5 days per week. To measure the autophagy flux in vivo, chloroquine was dissolved in PBS and injected intraperitoneally at the dosage of 50 mg/kg, To inhibit autophagy in vivo, SBI-0206965 (Adooq Bioscience; Al 5795) was dissolved in PBS containing 50% DMSO, and injected intraperitoneally into mice at the of 2 mg/kg body weight once per day for 7 days. Mice were sacrificed and tissues were collected 4 h after the last drug injection. For cell culture use, ML246 was dissolved in 100% DMSO and used at the concentration of 0.5 µM.

Mouse exercise studies. For acute exercise studies, 8-week old mice (wild-type and Becn 1 FA/FA mice crossed to GFP-LC3 transgenic mice) were acclimated and trained on a 10° uphill Exer 3/6 open treadmill (Columbus Instruments) for 2 days. On day 1 mice ran for 5 mM at 8 m/min and on day 2 mice ran for 5 mM at 8 m/min followed by another 5 min at 10 m/min. On day 3, mice were subjected to a single bout of running starting at the speed of 10 m/min. Forty minutes later, the treadmill speed was increased at a rate of 1 m/min every 10 min for 30 min, and then increased at rate of 1 m/min every 5 mM for 20 min, so that the mice ran for a total of 90 minutes of exercise and 1070 meters of running distance. For long-term exercise, 2-month old 5XFAD mice were single-housed in a cage containing a running wheel (11.4 cm diameter) for a total of 4 months. The running capacity of mice was monitored by an odometer connected to the wheel.

Morris water maze testing. For animal behavior, 6-month old mice were tested. The Morris water maze test consists of two sections: the visible platform testing and hidden platform testing. During the tests, mice were placed in the water tank filled with opaque water (maintained at 25° C.), with their heads facing toward the tank wall. In the visible platform section, a black platform extending 2 cm above the water level was used for these trials. For each trial, the platform was randomly positioned, and the mouse was placed in the tank at different start positions. The trial was stopped after the mouse found and climbed onto the platform, and the escape latency was recorded. The trial was stopped if the mouse did not climb onto the platform in 60 s, and the experimenter guided it to the platform. Mice were tested for 4 days with eight trials per day. In the hidden platform section, a transparent platform underneath the water level was used instead of the black one during all trials, mice were tested with a fixed platform location over 5 days period with six trials per day, and they were allowed to search the platform in 60 s. In the tests, two parameters were evaluated: the trail duration (s) and distance to the platform (m).

Dot blot assay. Snap frozen hemi-brain were homogenized in 800 µl phosphate-buffered saline (PBS; Sigma-Aldrich, D8537) with 1% Triton X-100 supplemented with halt proteinase inhibitor cocktail (ThermoFisher Scientific), and halt phosphatase inhibitor cocktail (ThermoFisher Scientific). Protein concentration was quantified using BCA Assay (Pierce). For Aβ342 dot blots, 10 mg/ml brain homogenates were extracted in guanidine buffer (5 M guanidine-HCl [GuHCl], 50 mM Tris HCl pH 8.0) overnight at room temperature. One µl of sample was spotted in triplicate on 0.2 µm nitrocellulose membrane, and dried for 1 h at 37° C. The membrane was stained with Ponceau S, and the dot blot signal on the membrane was detected by immunostaining with Aβ42 antibody (Invitrogen, 700254, 1:1000) and HRP-conjugated secondary antibody (Santa Cruz Biotechnology, sc2004, 1:2000). Aβ42 signals were normalized to the Ponceau S staining. To separate soluble and insoluble Aβ fractions, 10 mg/ml of the total homogenated brains were centrifuged at 14000 rpm, 4° C. for 30 min. The supernatant (soluble fraction) was used directly for dot blot assays. The pellet (insoluble fraction) was extracted in guanidine buffer overnight at room temperature, and used in dot blot analyses. To measure Aj3 levels in conditioned media of APP-HEK293 cells, media of 72-h cell culture was collected, mixed with 4× sample buffer (50 mM Tris-HCl pH6.8, 2% SDS, 10% glycerol, 1%13-mercaptoethanol, 12.5 mM EDTA, 0.02% bromophenol blue), and boiled at 95° C. for 10 min. One µl of each sample was spotted on nitrocellulose membrane for dot blot analysis.

ELISA. GuHCl extracted brain samples prepared in the same way as dot blot assays were diluted 1:1000, and ELISA analyses of Aβ42 were performed according to manufacturer's instructions (Thermo Fisher Scientific, KHB3441).

Immunofluorescence microscopy. Paraformaldehyde-fixed brain tissues were sectioned at 30 µm thickness. Free-floating sagittal sections were immunostained with 1% thioflavin S (Sigma-Aldrich, 230456) for 20 minutes. Additional sections were immunostained with Aβ (Invitrogen, 700254, 1:500) and Alexa Fluro 594 goat anti rabbit (ThermoFisher Scientific, Al 1012). Sections were mounted on slides with mounting medium containing DAPI (Vectashield) and then analyzed by fluorescence microscopy under the 10× objective.

Confocal Microscopy. Cortical neurons derived from PDAPP Becnr 1 and PDAPP BecnlFAJF A embryos were grown on poly-L-lysine coated culture slides. Cells (9 DIV) were then fixed in 4% paraformaldehyde and permeabilized with 0.3% Triton X-100. Slides were blocked for 1 h in PBS containing 1% BSA and 2% normal goat serum and then incubated overnight at 4° C. with primary antibodies: anti-APP (Biolegend; 803001) and anti-Rab5 (Cell Signaling Technology; 3547) or anti-Rab7 (Cell Signaling Technology; 9367). After washing, slides were incubated with species-specific Alexa-dye conjugated secondary antibodies for 1 h at room temperature. Slides were sealed with coverslip using mounting medium containing DAPI (Vectashield) and then analyzed by confocal microscopy. Confocal images were collected on Nikon A1 microscope using a 60× oil immersion objective lens and NIS Elements software. The lander's colocalization coefficient and the fluorescence intensity profile were generated using the NIS Element software.

Autophagy analyses. For assessment of autophagy in vivo, 8-week old male WT and Becn 1FA/FA mice crossed to GFP-LC3 mice were exercised for 90 minutes, or starved for 48 h, and then anaesthetized by isoflurane and perfused with 4% PFA Brain and muscle samples were fixed in 4% PFA overnight, 15% sucrose for 4 h and 30% sucrose overnight before frozen sections were prepared. The number of GFP-LC3 puncta per unit area of tissue was quantified by fluorescence microscopy. Autophagy in vivo was also analyzed by western blot analysis of brain tissue extracts with antibodies against LC3 and p62/SQSTM1 (see below for details).

Western blot analyses. Cell or mouse muscle and brain extracts were prepared in lysis buffer containing 50 mM Tris (pH 7.4), 150 mM NaCl, 1 mM EDTA, 1% Triton X-100, halt proteinase inhibitor cocktail (ThermoFisher Scientific) and halt phosphatase inhibitor cocktail (ThermoFisher Scientific), and subjected to western blot analysis with anti-LC3 (Novus Biologicals, NB100-2220), anti-SQSTM 1 (Abnova, H00008878-M01), anti-Af342 (Invitrogen; 700254), anti-APP (Biolegend; 803001), HRP-conjugated GFP antibody (Santa Cruz Biotechnology, sc9996), anti-HA (Cell Signaling Technology, C29F4), anti-ATG7 (Sigma Aldrich; A2856), anti-LDLR (Abeam, ab52818), anti-LRP 1 (Abeam, ab92544), and anti-ACTB/f3-actin-HRP (Santa Cruz Biotechnology, sc47778 HRP) antibodies. The band intensity was analyzed using the ImageJ software.

Filter trap assay. HeLa cells stably expressing CFP-HTT25Q, CFP-HTT65Q and CFP-HTT103Q were treated with 100 ng/ml tetracycline (IBI Scientific, IB02200) for 48 h, or 0.5 µM ML246 for 24 h with control or ATG7 siRNA (GE Dharmacon ON-TARGETplus control or ATG7 SMARTpool siRNA) for 48 h. Cells were then collected and lysed in lysis buffer containing 0.5% NP-40 for 30 min at 4° C. After centrifugation, the pellet was digested with 0.5 mg/ml DNaseI (in 20 mM Tris-Cl, pH 8.0) for 1 h at 37° C., and dissolved into lysates containing insoluble aggregates by 2% SDS, 50 mM DTT and 20 mM EDTA. The lysates were then added onto 0.2 µm nitrocellulose membrane that was pre-equilibrated with 2% SDS/TBS for 30 min, and were filtered through the membrane by gentle vacuum using the Bio-Dot SF microfiltration apparatus (Bio-Rad). The signal was detected by immunostaining with the HRP-conjugated GFP antibody (Santa Cruz Biotechnology, sc9996, 1:1000).

TUNEL assays. APP-HEK293 cells were cultured in 6-well dishes for 24 h and then the media was replaced with neuronal culture media. After 48 h, conditioned media was collected and used to treat primary cortical neurons (12 DIV) cultured on poly-L-lysine coated slides for another 24 h. Apoptotic neurons were detected by the In Situ Cell Death Detection Kit, TMR red (Roche, cat. #12156792910) according to the manufacturer's instructions. Nuclei were stained using the mounting medium containing DAPI (Vectashield). Quantification of red TUNEL-positive neurons was done using the NIS Elements software.

Generation of BECN1 knock out cells by CRISPR/Cas9. The gRNA sequence against human BECN I genome in exon 1 was designed using the CRISPR Design tool (http://crispr.mit.edu:8079), which contained a Sau3AI restriction enzyme site at the Cas9 cutting position on its gRNA sequence. Annealed oligonucleotides were inserted into the pSpCas9(BB)-2A-puro (PX459) V2.0 vector (Addgene, #62988). The plasmid was transfected into APP-HEK293 cells using lipofectamine 3000 (Thermo Fisher Scientific), and cells were selected for 72 h using DMEM supplemented with 2 µg/ml puromycin. Genome editing efficiency and protein expression levels were confirmed by Sau3AI enzymatic digestion and western blotting, respectively.

Generation of Becn1F121A-expressing stable cells. Mouse wild-type (WT) Becn1 or Becn1F121A mutant cDNA was sub-cloned into the pCDH-CMV-MCS-EF 1-GreenPuro vector (System Biosciences, Palo Alto, Calif., USA) using XbaI and BamHI restriction sites.

Lentivirus encoding Becn1 or Becn1F121A was produced by co-transfection of packing plasmids, pCMV-VSV-G (Addgene, #8454) and psPAX2 (Addgene, #12260) into HEK293 FT cells. The resulting lentivirus encoding Becn1 or Becn1F121A was used to infect BECNJ KO cells at the multiplicity of infection of 1 for 24 h in the presence of 10 μg/ml pol ybrene (Santa Cruz Biotechnology). Infected cells were selected and maintained in DMENI supplemented with 2 μg/ml puromycin (Thermo Fisher Scientific).

Biotin protection assay on cell-surface APP trafficking. The biotinylation procedure was modified from a previously reported protocol. HEK293 cells stably expressing APP were grown to 90% confluency on gelatin-coated 6 cm2 dish, washed with ice-cold PBS, and incubated in 0.3 mg/ml disulfide-cleavable biotin (EZlink Sulfa-NHS-SS-Biotin, Thermo Scientific) in PBS at 4° C. for 30 min. Cells were then washed with cold PBS and returned to warm medium at 37° C., and incubated for 5 or 15 min. Cells labeled "Total" were left on ice in PBS. Cells labeled "Stripping" were also left on ice in PBS and then stripped as described below. The remaining cell-surface biotinylated APP was stripped in 50 mM glutathione, 0.3 M NaCl, 75 mM NaOH, 10% FBS at 4° C. for 40 min. Glutathione was then quenched with 50 mM iodoacetamide and 1% bovine serum albumin in PBS at 4° C. for 15 min. Proteins were extracted in lysis buffer containing 0.1% sodium dodecyl sulfate (SDS), 0.5% sodium deoxycholate, 1% Triton X-100, 100 mM NaCl, 2 mM EDTA and 50 mM Tris-HCI 7.4 supplemented with protease and phosphatase inhibitor cocktail (Thermo Scientific), and supernatant was collected by centrifugation at 10,000×g for 10 min at 4° C. Biotinylated APP were isolated using streptavidin-agarose (Millipore) at 4° C. for 2 h. Precipitates were washed four times with wash buffer containing 0.1% SDS, 1% Triton X-100, 100 mM NaCl, 2 mM EDTA and 50 mM Tris-HCI 7.4, and proteins were eluted in SDS sample buffer by boiling.

Statistical analyses. P:S 0.05 was considered statistically significant in two-tailed, unpaired Student's t-tests for detection of differences between two experimental groups; Two-way ANOVA approach was used for comparison among multiple groups. Statistics on the survival study was done by the log-rank test. Figures are depicted as mean±SEM.

Example 1

This example demonstrates autophagy activation by ML246 and Rg2.

To determine autophagy activation by the 2 compounds ML246 and Rg2, several markers of autophagy induction were analyzed, including formation of autophagosomes in cells and transgenic mice expressing GFP-tagged MAP1LC3/LC3 (microtubule-associated protein 1 light chain 3; an autophagosome marker), degradation of SQSTM1/p62 (sequestosome 1; an autophagy receptor and substrate protein), and conversion of LC3 from the non-lipidated form (LC3-I) to the phagophore- and autophagosome-associated lipidated form (LC3-II). Both compounds markedly increased numbers of GFP-LC3 puncta (representing autophagosomes) and decreased levels of SQSTM1 in HeLa cells and in mouse brain, as potently as starvation (FIG. 3C-E, FIG. S3A-C), although we did not detect significant changes in LC3-II conversion in brain. In addition, when cotreated with the lysosomal inhibitor bafilomycin A1, ML246 or Rg2 led to more accumulation of GFP-LC3 puncta, LC3-II and SQSTM1 compared to normal conditions (FIG. 3C-D, FIG. S3D), suggesting an increased level of autophagic flux induced by either compound. Therefore, both agents are effective autophagy inducers in vitro and in vivo.

Example 2

This example demonstrates that ML246 and Rg2 autophagy inducers prevent WT mice from analgesic tolerance after chronic cannabinoid usage.

The efficacy of ML246 and Rg2 in the maintenance of cannabinoid analgesia in WT mice were tested. It was found that compared with vehicle injection, cotreatment of either ML246 or Rg2 with WIN potently rescued the pain-relieving effect of WIN in WT mice on day 14 to a day 1-like level (i.e., before repeated dosage) (FIG. 5A, Video S10-S12), suggesting that the autophagy-inducing compounds prevent analgesic tolerance induced by chronic WIN administration. The co-treatment regimen did not alter body weight of the mice (FIG. S4A). To confirm the findings with pharmacological inducers, it was further asked whether autophagy induction by physiological methods also rescues cannabinoid tolerance. Two methods that activate autophagy in mouse brain were adopted: the first is daily voluntary exercise by use of running wheels, which allows mice to run for approximately 1 km/night; and the second is a "2-day on/1-day off" periodic starvation protocol, in which mice were subjected to cycles of 48-h fasting followed by 24-h feeding that allowed them to return to normal weight in each cycle (FIG. 5B, FIG. S4B).

Although the increase in autophagosome formation was not significant in the brain (frontal cortex) of GFP-LC3 mice after a single bout of 48-h fasting as previously reported using fluorescence microscopy (FIG. S4C), a cumulative effect on autophagy induction in the same brain region after multiple rounds of alternating fasting and feeding was observed, demonstrated by a significant induction of GFP-LC3 puncta in the frontal cortex after 4 cycles of "2-day on/1-day off" starvation (FIG. S4C). Although the exact mechanism of this additive effect is currently unclear, it may be due to a relatively stable glucose supply and low metabolism in the brain (compared to muscle and liver), leading to slow formation/turnover of autophagosomes that can be detected after repeated induction. This hypothesis is supported by the observation that skeletal muscle, which has high metabolic activity, does not show much cumulative effect with regard to autophagy induction by periodic starvation cycles (FIG. S4C). At the end of chronic WIN treatment, similar to mice treated with autophagy-inducing compounds, mice undergoing daily running or intermittent fasting showed significantly higher sensitivity to the analgesic effects of WIN (FIG. 5C, Video S13-S15), suggesting that physiological autophagy inducers, such as exercise and starvation, prevent analgesic tolerance as well. Altogether, these data suggest that both pharmacological and physiological autophagy inducers prevent cannabinoid tolerance to repeated dosage.

Example 3

This example demonstrates that autophagy induction preserves brain CNR1 level and activity in response to chronic cannabinoids.

To investigate whether restoration of CNR1 signaling underlies the behavioral regulation by autophagy activation, the level and functionality of CNR1 in mouse brain after co-administration of chronic cannabinoids and autophagy inducers was analyzed. Consistent with behavioral sensitization to WIN, after chronic WIN treatment higher levels of CNR1 in the brain of mice concurrently treated with ML246 or Rg2 (FIG. 6A), or fasted or exercised (FIG. 6B) were detected, which were comparable to the brain CNR1 level prior to chronic cannabinoid exposure (FIG. 1A). To determine whether the increased level of CNR1 represents CNR1 resensitization in the brain, the agonist-induced phosphorylation of signaling kinases downstream of CNR1 after chronic WIN exposure was analyzed. It was found that repeated WIN treatment decreased activation of CNR1 signaling induced by agonists (FIG. 6C), whereas autophagy induction, either pharmacologically by ML246 or Rg2, or physiologically by starvation or exercise, rescued the CNR1 signaling in spite of repeated WIN dosage, demonstrated by increased phosphorylation of MAP2K and MAPK8/9 (FIG. 6D-E). Thus, these findings suggest that activating autophagy pharmacologically or physiologically effectively improves CNR1 signaling after chronic cannabinoid exposure.

Example 4

This example demonstrates the autophagy flux exhibited by compounds in accordance with an embodiment of the invention.

The Promega Augophagy Assay System uses LC3 to monitor the autophagy process. LC3 is tagged with HiBiT, an 11 amino acid peptide which has high affinity for LgBiT. LgBiT is a small recombinant protein derived from Nano-Luc. When HiBiT associates with LgBiT, a strong luciferase activity is reconstituted. An increase in autophagy will accelerate the degradation of LC3 reporter which decreases the assay signal. In contrast, inhibition of autophagy causes the accumulation of LC3 which will increase the reporter levels and assay signal. The results are set forth in Table 1.

TABLE 1

| Compound | AC50 (uM) | CC-v2 | Efficacy |
|---|---|---|---|
| (structure) | null | 4 | −33.349 |
| (structure) | null | 4 | −41.872 |
| (structure) | null | 4 | −35.13 |
| (structure) | null | 4 | −31.327 |

TABLE 1-continued

| Compound | AC50 (uM) | CC-v2 | Efficacy |
|---|---|---|---|
| (structure) | null | 4 | −22.429 |
| (structure) | null | 4 | −16.857 |
| (structure) | null | 4 | −26.203 |
| (structure) | null | 4 | −16.14 |
| (structure) | null | 4 | −18.912 |

TABLE 1-continued
| Compound | AC50 (uM) | CC-v2 | Efficacy |
|---|---|---|---|
| 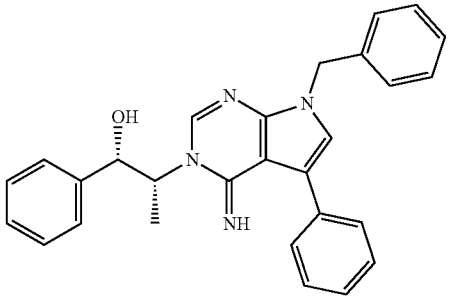 [SMILES: C[C@H]([C@@H](O)c1ccccc1)n1cnc2c(c(-c3ccccc3)cn2Cc2ccccc2)c1=N] | null | 4 | −14.285 |
| 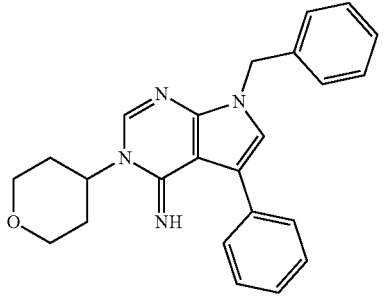 [SMILES: N=c1c2c(-c3ccccc3)cn(Cc3ccccc3)c2ncn1C1CCOCC1] | null | 4 | −21.666 |
| 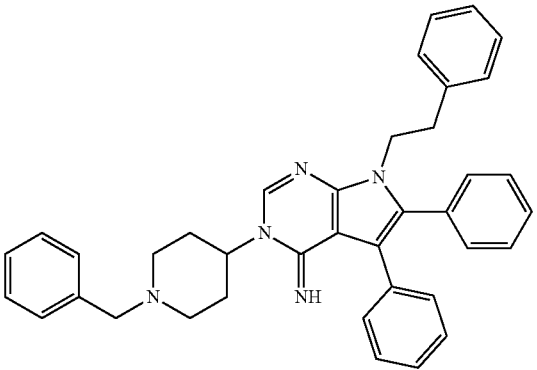 [SMILES: N=c1c2c(-c3ccccc3)c(-c3ccccc3)n(CCc3ccccc3)c2ncn1C1CCN(Cc2ccccc2)CC1] | null | 4 | 33.237 |
| 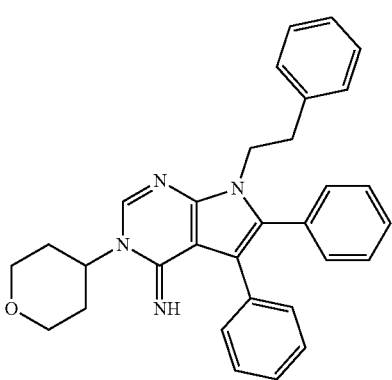 [SMILES: N=c1c2c(-c3ccccc3)c(-c3ccccc3)n(CCc3ccccc3)c2ncn1C1CCOCC1] | null | 4 | 29.216 |

TABLE 1-continued

| Compound | AC50 (uM) | CC-v2 | Efficacy |
|---|---|---|---|
| *structure* | null | 4 | −19.963 |
| *structure* | null | 4 | −24.167 |
| *structure* | null | 4 | −27.792 |
| *structure* | null | 4 | −21.187 |

TABLE 1-continued
| Compound | AC50 (uM) | CC-v2 | Efficacy |
|---|---|---|---|
| 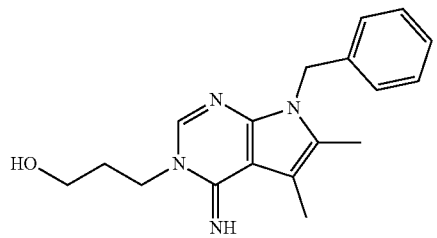 [SMILES: Cc1c(C)n(Cc2ccccc2)c2ncn(CCCO)c(=N)c12] | null | 4 | −16.424 |
| 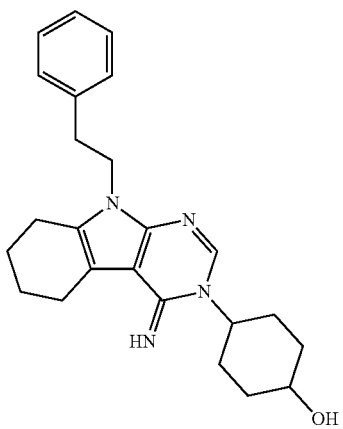 [SMILES: N=c1c2c3c(n(CCc4ccccc4)c2ncn1C1CCC(O)CC1)CCCC3] | null | 4 | −14.978 |
| 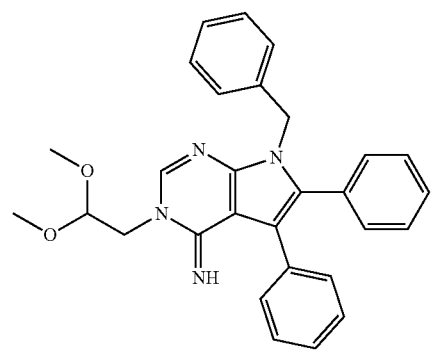 [SMILES: COC(Cn1cnc2c(c(-c3ccccc3)c(-c3ccccc3)n2Cc2ccccc2)c1=N)OC] | 0.231028 | −1.2 | −68.016 |
| 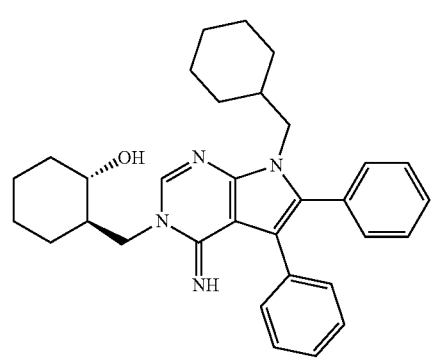 [SMILES: N=c1c2c(-c3ccccc3)c(-c3ccccc3)n(CC3CCCCC3)c2ncn1C[C@H]1CCCC[C@@H]1O] | 0.366154 | −1.2 | −46.977 |

TABLE 1-continued

| Compound | AC50 (uM) | CC-v2 | Efficacy |
|---|---|---|---|
| | 1.157882 | −1.2 | −42.81 |
| | 1.635552 | −2.2 | −55.273 |
| | 1.835119 | −1.2 | −34.836 |
| | 2.310278 | −1.2 | −47.061 |

TABLE 1-continued

| Compound | AC50 (uM) | CC-v2 | Efficacy |
|---|---|---|---|
| (structure) | 2.592175 | −1.2 | −26.722 |
| (structure) | 2.592175 | −2.2 | −57.764 |
| (structure) | 2.592175 | −1.2 | −40.689 |
| (structure) | 2.592175 | −1.2 | −29.158 |

TABLE 1-continued
| Compound | AC50 (uM) | CC-v2 | Efficacy |
|---|---|---|---|
| 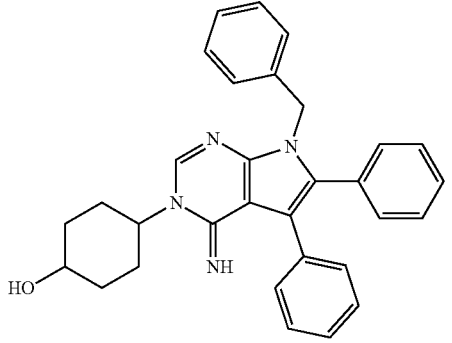 [SMILES: N=c1c2c(-c3ccccc3)c(-c3ccccc3)n(Cc3ccccc3)c2ncn1C1CCC(O)CC1] | 2.908468 | −2.2 | −60.226 |
| 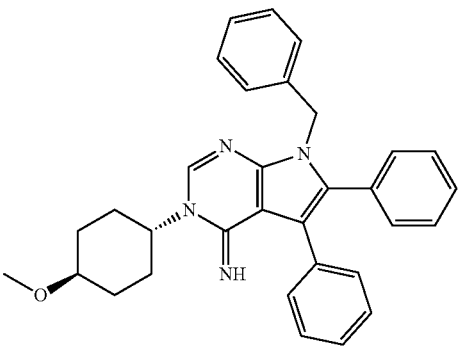 [SMILES: CO[C@H]1CC[C@H](n2cnc3c(c(-c4ccccc4)c(-c4ccccc4)n3Cc3ccccc3)c2=N)CC1] | 2.908468 | −2.2 | −67.701 |
| 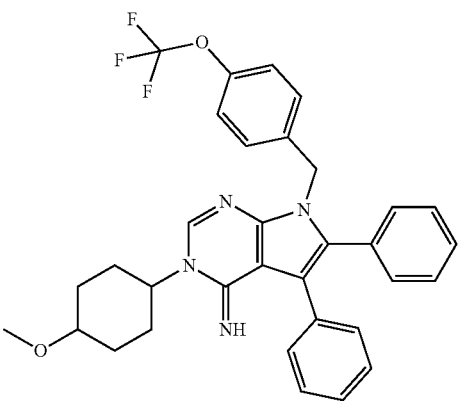 [SMILES: COC1CCC(n2cnc3c(c(-c4ccccc4)c(-c4ccccc4)n3Cc3ccc(OC(F)(F)F)cc3)c2=N)CC1] | 2.908468 | −1.2 | −40.359 |
| 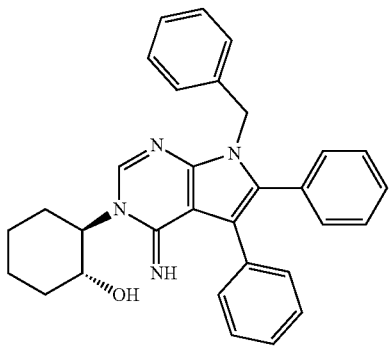 [SMILES: N=c1c2c(-c3ccccc3)c(-c3ccccc3)n(Cc3ccccc3)c2ncn1[C@@H]1CCCC[C@H]1O] | 3.263355 | −2.2 | −62.315 |

TABLE 1-continued
| Compound | AC50 (uM) | CC-v2 | Efficacy |
|---|---|---|---|
| 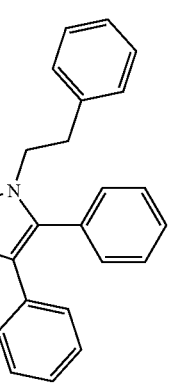 | 3.661544 | −1.2 | −43.723 |
| 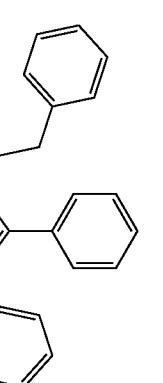 | 3.661544 | −1.2 | −38.734 |
| 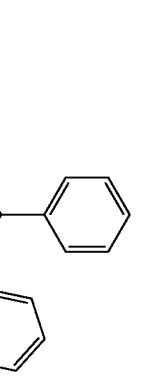 | 3.661544 | −1.2 | −39.625 |
| 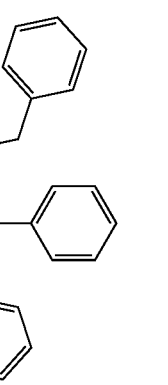 | 4.609611 | −2.2 | −55.8 |

TABLE 1-continued

| Compound | AC50 (uM) | CC-v2 | Efficacy |
|---|---|---|---|
|  | 4.609611 | −2.2 | −56.199 |
|  | 5.172069 | −2.2 | −43.066 |
|  | 5.172069 | −2.2 | −44.226 |
|  | 5.172069 | −2.2 | −43.45 |

TABLE 1-continued
| Compound | AC50 (uM) | CC-v2 | Efficacy |
|---|---|---|---|
| 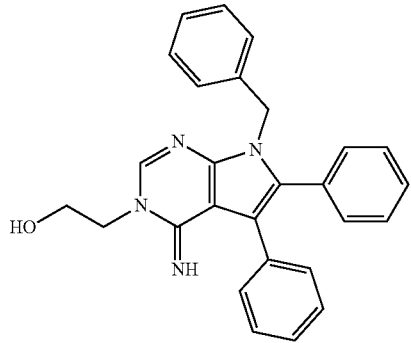 [SMILES: N=c1c2c(-c3ccccc3)c(-c3ccccc3)n(Cc3ccccc3)c2ncn1CCO] | 5.803157 | −2.2 | −50.936 |
| 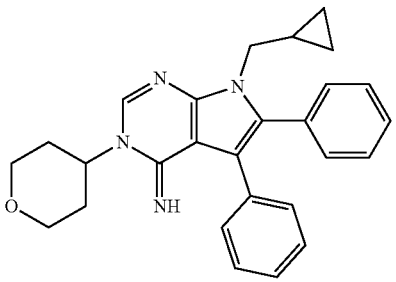 [SMILES: N=c1c2c(-c3ccccc3)c(-c3ccccc3)n(CC3CC3)c2ncn1C1CCOCC1] | 7.305741 | −2.2 | −56.524 |
| 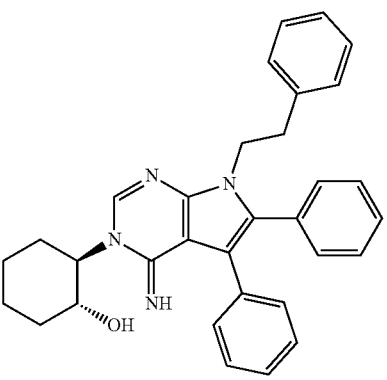 [SMILES: N=c1c2c(-c3ccccc3)c(-c3ccccc3)n(CCc3ccccc3)c2ncn1[C@@H]1CCCC[C@H]1O] | 7.305741 | −2.2 | −74.961 |
| 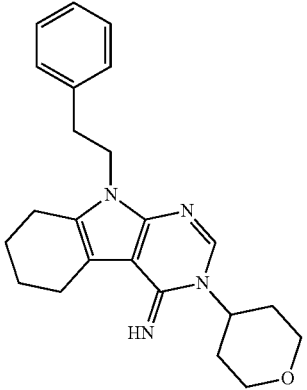 [SMILES: N=c1c2c3c(n(CCc4ccccc4)c2ncn1C1CCOCC1)CCCC3] | 7.305741 | −2.4 | −46.895 |

TABLE 1-continued

| Compound | AC50 (uM) | CC-v2 | Efficacy |
|---|---|---|---|
| (structure) | 8.197177 | −2.4 | −23.111 |
| (structure) | 9.197383 | −2.2 | −42.103 |
| (structure) | 9.197383 | −2.4 | −72.114 |
| (structure) | 9.197383 | −2.2 | −59.647 |

TABLE 1-continued
| Compound | AC50 (uM) | CC-v2 | Efficacy |
|---|---|---|---|
| 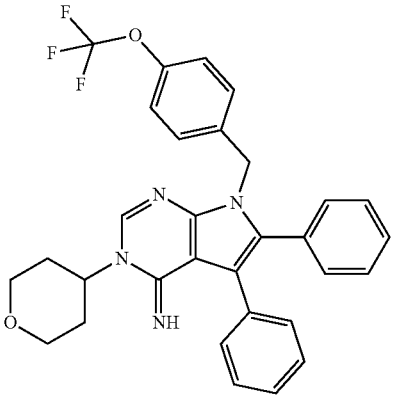 [SMILES: N=c1c2c(-c3ccccc3)c(-c3ccccc3)n(Cc3ccc(OC(F)(F)F)cc3)c2ncn1C1CCOCC1] | 9.197383 | −2.2 | −56.61 |
| 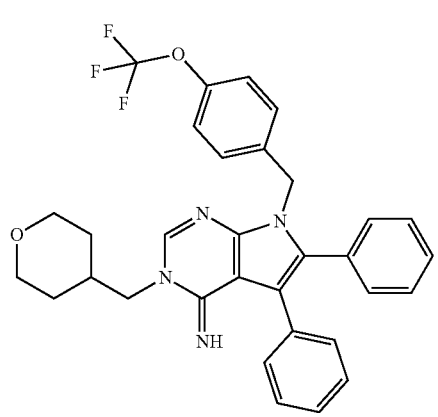 [SMILES: N=c1c2c(-c3ccccc3)c(-c3ccccc3)n(Cc3ccc(OC(F)(F)F)cc3)c2ncn1CC1CCOCC1] | 9.197383 | −2.2 | −45.302 |
| 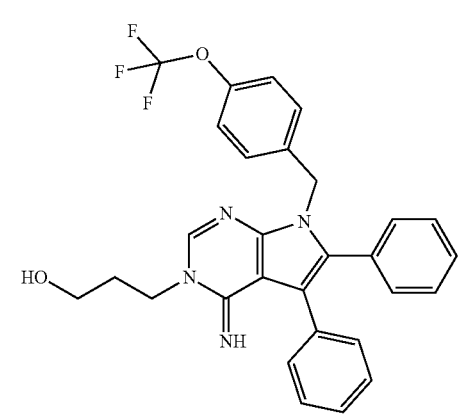 [SMILES: N=c1c2c(-c3ccccc3)c(-c3ccccc3)n(Cc3ccc(OC(F)(F)F)cc3)c2ncn1CCCO] | 9.197383 | −2.2 | −42.207 |
| 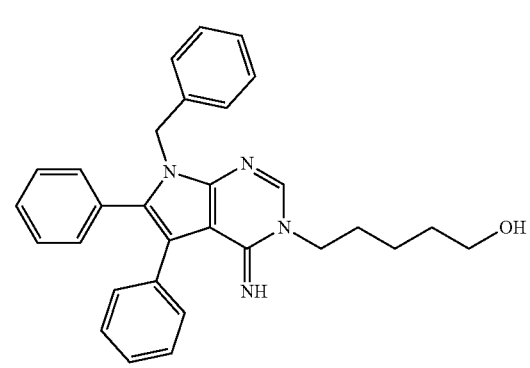 [SMILES: N=c1c2c(-c3ccccc3)c(-c3ccccc3)n(Cc3ccccc3)c2ncn1CCCCCO] | 10.31963 | −2.2 | −48.501 |

TABLE 1-continued

| Compound | AC50 (uM) | CC-v2 | Efficacy |
|---|---|---|---|
| (structure) | 10.31963 | −2.2 | −45.869 |
| (structure) | 10.31963 | −2.2 | −65.338 |
| (structure) | 10.31963 | −2.2 | −54.266 |
| (structure) | 10.31963 | −2.2 | −66.806 |

TABLE 1-continued

| Compound | AC50 (uM) | CC-v2 | Efficacy |
|---|---|---|---|
| (structure) | 10.31963 | −2.2 | −61.258 |
| (structure) | 10.31963 | −2.2 | −58.819 |
| (structure) | 10.31963 | −2.2 | −72.099 |
| (structure) | 11.57882 | −2.2 | −47.609 |

TABLE 1-continued

| Compound | AC50 (uM) | CC-v2 | Efficacy |
|---|---|---|---|
| (structure) | 11.57882 | −2.2 | −47.778 |
| (structure) | 12.99165 | −2.2 | −51.084 |
| (structure) | 12.99165 | −2.2 | −54.232 |
| (structure) | 12.99165 | −2.4 | −28.13 |

TABLE 1-continued
| Compound | AC50 (uM) | CC-v2 | Efficacy |
|---|---|---|---|
| 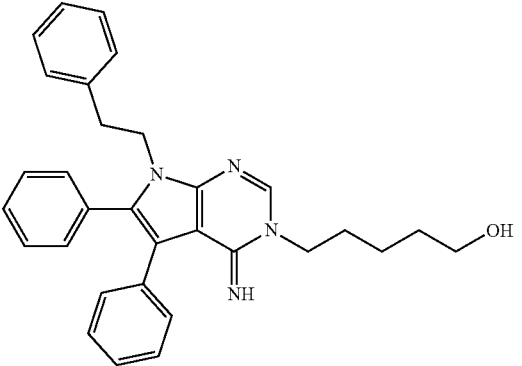 [SMILES: N=c1c2c(-c3ccccc3)c(-c3ccccc3)n(CCc3ccccc3)c2ncn1CCCCCO] | 12.99165 | −2.2 | −46.997 |
| 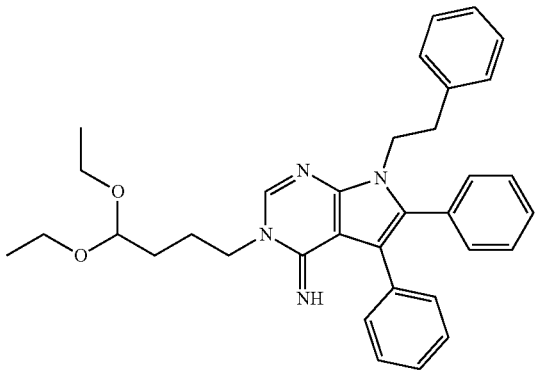 [SMILES: CCOC(CCCn1cnc2c(c(-c3ccccc3)c(-c3ccccc3)n2CCc2ccccc2)c1=N)OCC] | 12.99165 | −2.2 | −61.253 |
| 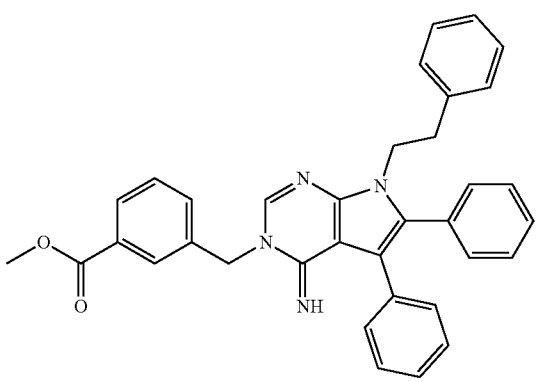 [SMILES: COC(=O)c1cccc(Cn2cnc3c(c(-c4ccccc4)c(-c4ccccc4)n3CCc3ccccc3)c2=N)c1] | 12.99165 | −2.2 | −57.077 |
| 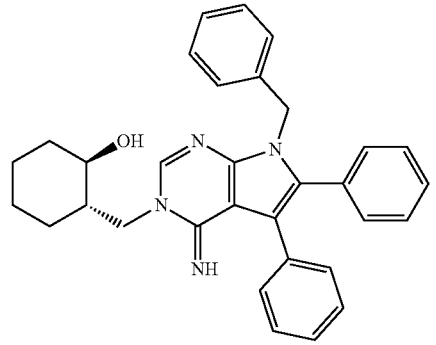 [SMILES: N=c1c2c(-c3ccccc3)c(-c3ccccc3)n(Cc3ccccc3)c2ncn1C[C@@H]1CCCC[C@H]1O] | 12.99165 | −2.2 | −87.743 |

TABLE 1-continued
| Compound | AC50 (uM) | CC-v2 | Efficacy |
|---|---|---|---|
| 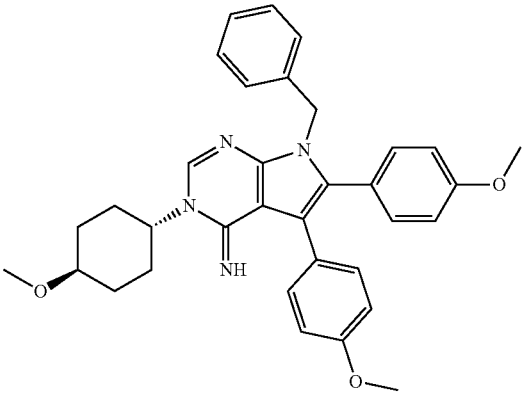 | 12.99165 | −2.2 | −40.491 |
| 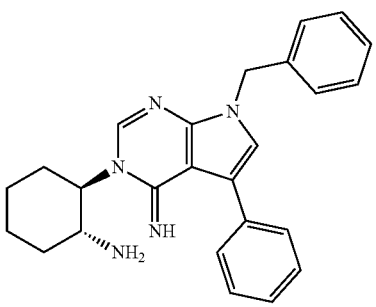 [SMILES: N=c1c2c(-c3ccccc3)cn(Cc3ccccc3)c2ncn1[C@@H]1CCCC[C@H]1N] | 14.57687 | −2.2 | −33.48 |
| 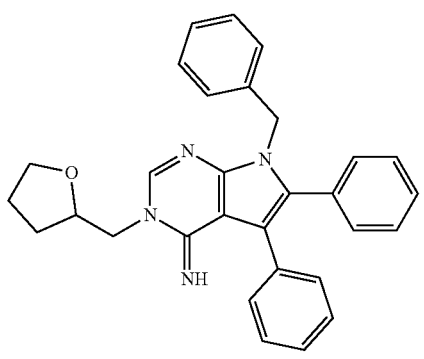 [SMILES: N=c1c2c(-c3ccccc3)c(-c3ccccc3)n(Cc3ccccc3)c2ncn1CC1CCCO1] | 14.57687 | −2.2 | −69.813 |
| 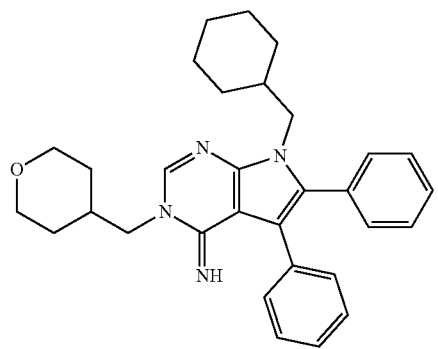 [SMILES: N=c1c2c(-c3ccccc3)c(-c3ccccc3)n(CC3CCCCC3)c2ncn1CC1CCOCC1] | 14.57687 | −2.2 | −62.519 |

TABLE 1-continued

| Compound | AC50 (uM) | CC-v2 | Efficacy |
|---|---|---|---|
|  | 14.57687 | −2.2 | −32.481 |
|  | 16.35552 | −2.2 | −41.294 |
|  | 16.35552 | −3 | −36.96 |
|  | 16.35552 | −2.2 | −70.38 |

TABLE 1-continued

| Compound | AC50 (uM) | CC-v2 | Efficacy |
|---|---|---|---|
| | 16.35552 | −2.2 | −41.871 |
| | 16.35552 | −2.2 | −65.79 |
| | 16.35552 | −2.2 | −53.785 |
| | 16.35552 | −3 | −47.531 |

TABLE 1-continued

| Compound | AC50 (uM) | CC-v2 | Efficacy |
|---|---|---|---|
| | 18.35119 | −2.2 | −46.236 |
| | 18.35119 | −2.2 | −89.583 |
| | 18.35119 | −2.4 | −29.548 |
| | 20.59038 | −2.4 | −31.388 |

TABLE 1-continued

| Compound | AC50 (uM) | CC-v2 | Efficacy |
|---|---|---|---|
| | 20.59038 | −2.2 | −95.847 |
| | 20.59038 | −2.2 | −74.202 |
| | 20.59038 | −2.2 | −82.619 |
| | 20.59038 | −2.2 | −82.254 |

TABLE 1-continued

| Compound | AC50 (uM) | CC-v2 | Efficacy |
|---|---|---|---|
| (structure) | 20.59038 | −2.2 | −52.964 |
| (structure) | 20.59038 | −2.2 | −73.624 |
| (structure) | 20.59038 | −2.2 | −64.213 |
| (structure) | 20.59038 | −2.2 | −52.721 |

TABLE 1-continued

| Compound | AC50 (uM) | CC-v2 | Efficacy |
|---|---|---|---|
| (structure) | 20.59038 | −2.4 | −37.729 |
| (structure) | 20.59038 | −2.2 | −44.936 |
| (structure) | 20.59038 | −2.2 | −49.787 |
| (structure) | 20.59038 | −2.2 | −34.898 |

TABLE 1-continued
| Compound | AC50 (uM) | CC-v2 | Efficacy |
|---|---|---|---|
| 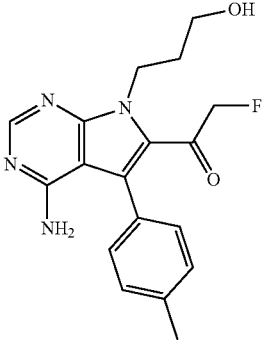 [SMILES: Cc1ccc(-c2c(C(=O)CF)n(CCCO)c3ncnc(N)c23)cc1] | 20.59038 | −3 | −44.672 |
| 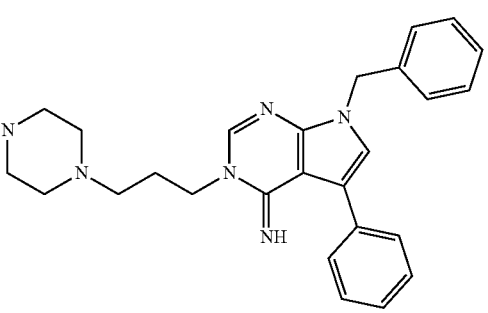 | 23.10278 | −3 | −49.304 |
| 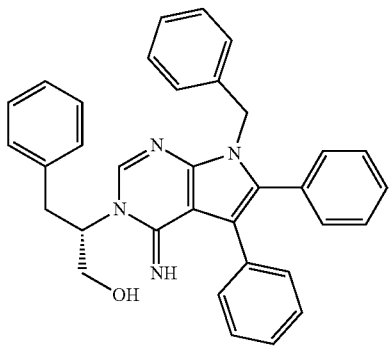 [SMILES: N=c1c2c(-c3ccccc3)c(-c3ccccc3)n(Cc3ccccc3)c2ncn1[C@H](CO)Cc1ccccc1] | 23.10278 | −3 | −45.451 |
| 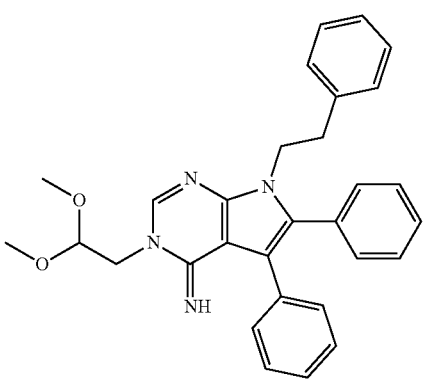 [SMILES: COC(Cn1cnc2c(c(-c3ccccc3)c(-c3ccccc3)n2CCc2ccccc2)c1=N)OC] | 23.10278 | −2.2 | −79.87 |

TABLE 1-continued
| Compound | AC50 (uM) | CC-v2 | Efficacy |
|---|---|---|---|
| 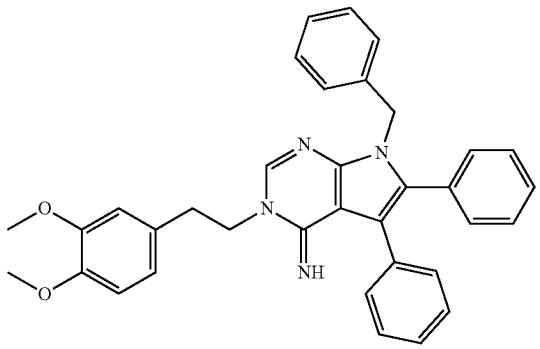 [SMILES: COc1ccc(CCn2cnc3c(c(-c4ccccc4)c(-c4ccccc4)n3Cc3ccccc3)c2=N)cc1OC] | 23.10278 | −3 | −60.207 |
| 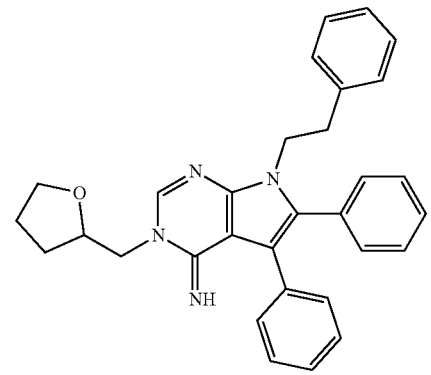 [SMILES: N=c1c2c(-c3ccccc3)c(-c3ccccc3)n(CCc3ccccc3)c2ncn1CC1CCCO1] | 23.10278 | −2.2 | −72.154 |
| 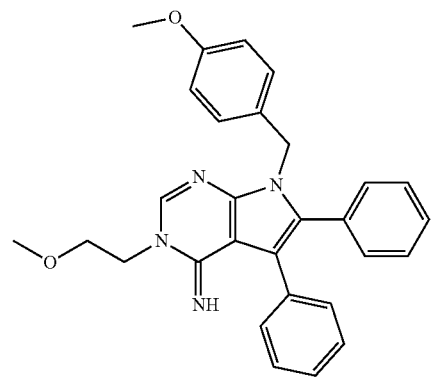 [SMILES: COCCn1cnc2c(c(-c3ccccc3)c(-c3ccccc3)n2Cc2ccc(OC)cc2)c1=N] | 23.10278 | −2.2 | −47.908 |
| 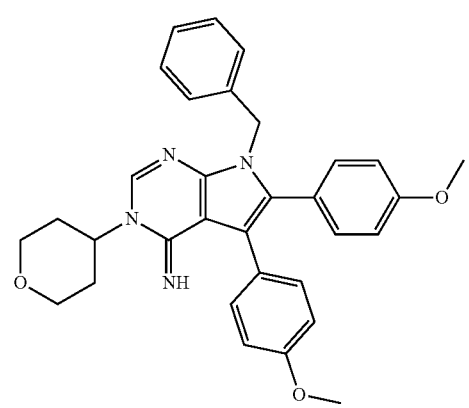 [SMILES: COc1ccc(-c2c(-c3ccc(OC)cc3)n(Cc3ccccc3)c3ncn(C4CCOCC4)c(=N)c23)cc1] | 23.10278 | −3 | −38.755 |

TABLE 1-continued
| Compound | AC50 (uM) | CC-v2 | Efficacy |
|---|---|---|---|
| 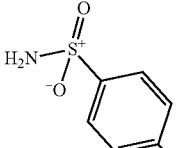 | 23.10278 | −2.2 | −45.848 |
| 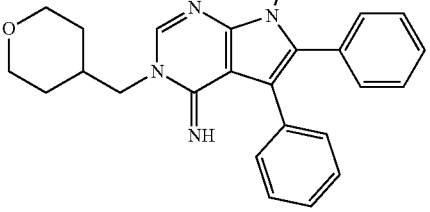 | 23.10278 | −2.4 | −20.347 |
| 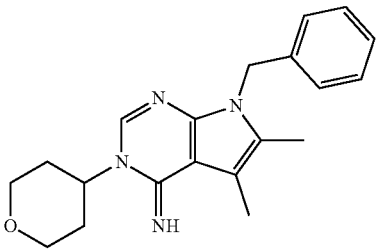 [SMILES: Cc1c(C)n(Cc2ccccc2)c2ncn(C3CCOCC3)c(=N)c12] | 23.10278 | −3 | −53.745 |
| 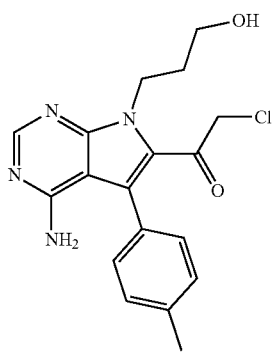 [SMILES: Cc1ccc(-c2c(C(=O)CCl)n(CCCO)c3ncnc(N)c23)cc1] | 25.92175 | −2.2 | −49.25 |

TABLE 1-continued
| Compound | AC50 (uM) | CC-v2 | Efficacy |
|---|---|---|---|
| 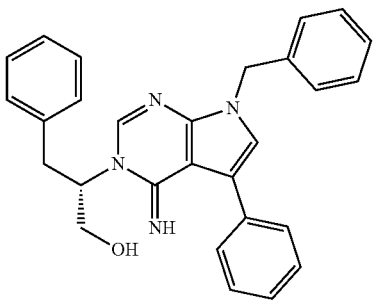 [SMILES: N=c1c2c(-c3ccccc3)cn(Cc3ccccc3)c2ncn1[C@H](CO)Cc1ccccc1] | 25.92175 | −2.4 | −30.912 |
| 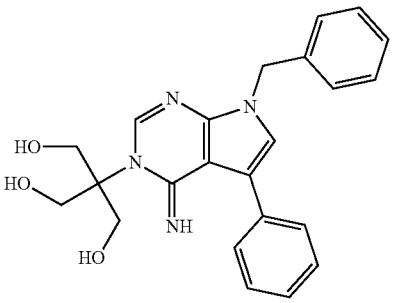 [SMILES: N=c1c2c(-c3ccccc3)cn(Cc3ccccc3)c2ncn1C(CO)(CO)CO] | 29.08468 | −2.4 | −30.83 |
| 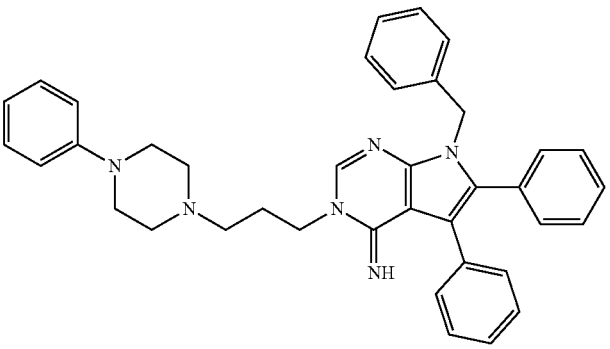 [SMILES: N=c1c2c(-c3ccccc3)c(-c3ccccc3)n(Cc3ccccc3)c2ncn1CCCN1CCN(c2ccccc2)CC1] | 29.08468 | −3 | −39.866 |
| 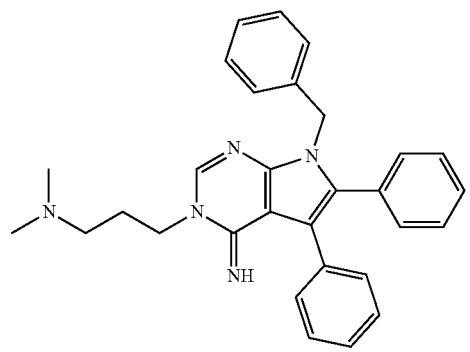 [SMILES: CN(C)CCCn1cnc2c(c(-c3ccccc3)c(-c3ccccc3)n2Cc2ccccc2)c1=N] | 29.08468 | −3 | −49.625 |

TABLE 1-continued

| Compound | AC50 (uM) | CC-v2 | Efficacy |
|---|---|---|---|
| (structure) | 29.08468 | −3 | −82.813 |
| (structure) | 29.08468 | −3 | −27.648 |
| (structure) | 32.63355 | −3 | −45.326 |
| (structure) | null | 4 | −33.349 |

All references, including publications, patent applications, and patents, cited herein are hereby incorporated by reference to the same extent as if each reference were individually and specifically indicated to be incorporated by reference and were set forth in its entirety herein.

The use of the teams "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating a condition responsive to induction of autophagy in a brain of a mammal in need thereof, comprising administering to the mammal an effective amount of a compound of formula (I):

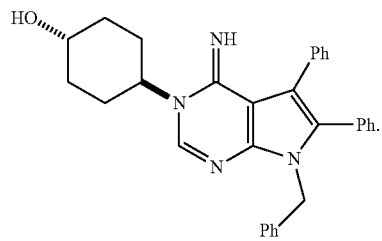

wherein $R^1$ is selected from the group consisting of thioalkyl, alkoxyalkyl, alkylthioalkyl, cycloalkyl, hydroxycycloalkyl, hydroxycycloalkylalkyl, thiocycloalkyl, alkoxycycloalkyl, alkylthiocycloalkyl, dialkylaminoalkyl, heterocyclyl, heterocyclylalkyl, heteroaryl, arylalkyl, arylalkylpiperidin-4-yl, arylpiperazinylalkyl, and heteroarylalkyl, $R^2$ is phenyl, optionally substituted with one or more substituents selected from the group consisting of halo, alkyl, hydroxyalkyl, thioalkyl, alkoxy, alkylthioalkyl, alkoxycarbonyl, alkylthiocarbonyl, amino, alkylamino, dialkylamino, and alkylcarbonyl, $R^3$ is phenyl, optionally substituted with one or more substituents selected from the group consisting of halo, alkyl, hydroxyalkyl, thioalkyl, alkoxy, alkylthioalkyl, alkoxycarbonyl, alkylthiocarbonyl, amino, alkylamino, dialkylamino, and alkylcarbonyl, and $R^4$ is selected from the group consisting of alkyl, cycloalkyl, cycloalkylalkyl, aryl, heteroaryl, and arylalkyl, or a pharmaceutically acceptable salt thereof, wherein $R^1$, $R^2$, $R^3$, and $R^4$, other than H, are optionally substituted on the aryl and/or alkyl portion with one or more substituents selected from the group consisting of halo, alkyl, hydroxyalkyl, thioalkyl, alkylthioalkyl, alkoxycarbonyl, alkylthiocarbonyl, amino, alkylamino, dialkylamino, aminosulfonyl, hydroxyl, perfluoroalkoxy, alkylenedioxy, and alkylcarbonyl, wherein the condition is a decrease in a level or activity of cannabinoid receptor 1 (CB1R) wherein the decrease in the levels or activity of CB1R results from repeated administration of at least one CB1R receptor agonist to the mammal.

2. The method of claim 1, wherein the compound is:

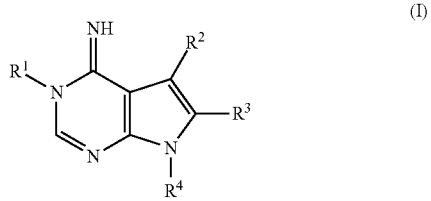

3. The method of claim 1, wherein the method results in reduction of cannabinoid tolerance and enhancement of the analgesic effects of cannabinoids.

4. The method of claim 1, wherein the condition is Alzheimer's disease.

5. The method of claim 4, wherein the induction of autophagy results in reduction of amyloid β (Aβ) peptides, wherein the Aβ peptides comprise Aβ42 peptide.

6. The method according to claim 1, wherein the CB1R receptor agonist is a cannabinoid.

7. The method according to claim 6, wherein the method results in reduction of cannabinoid tolerance and enhancement of the analgesic effects of cannabinoids.

8. The method according to claim 1, wherein the CBR1 receptor agonist is tetrahydrocannabinol.

9. The method according to claim 1, wherein the heterocyclylalkyl is (tetrahydrofuran 3 yl)methyl, (tetrahydrofuran 2 yl)methyl, or (tetrahydro 2H pyran 4yl)methyl.

* * * * *